United States Patent
Chang et al.

(10) Patent No.: US 11,884,732 B2
(45) Date of Patent: *Jan. 30, 2024

(54) PROTEINS BINDING HER2, NKG2D AND CD16

(71) Applicant: Dragonfly Therapeutics, Inc., Waltham, MA (US)

(72) Inventors: Gregory P. Chang, Medford, MA (US); Ann F. Cheung, Lincoln, MA (US); William Haney, Wayland, MA (US); Bradley M. Lunde, Lebanon, NH (US); Bianka Prinz, Lebanon, NH (US)

(73) Assignee: Dragonfly Therapeutics, Inc., Waltham, MA (US)

( * ) Notice: Subject to any disclaimer, the term of this patent is extended or adjusted under 35 U.S.C. 154(b) by 432 days.

This patent is subject to a terminal disclaimer.

(21) Appl. No.: 16/486,569

(22) PCT Filed: Feb. 20, 2018

(86) PCT No.: PCT/US2018/018771
§ 371 (c)(1),
(2) Date: Aug. 16, 2019

(87) PCT Pub. No.: WO2018/152518
PCT Pub. Date: Aug. 23, 2018

(65) Prior Publication Data
US 2020/0231678 A1 Jul. 23, 2020

Related U.S. Application Data

(60) Provisional application No. 62/461,146, filed on Feb. 20, 2017.

(51) Int. Cl.
C07K 16/28 (2006.01)
A61P 35/00 (2006.01)
C07K 16/32 (2006.01)

(52) U.S. Cl.
CPC .......... *C07K 16/2851* (2013.01); *A61P 35/00* (2018.01); *C07K 16/283* (2013.01); *C07K 16/32* (2013.01); *C07K 2317/31* (2013.01); *C07K 2317/33* (2013.01); *C07K 2317/524* (2013.01); *C07K 2317/53* (2013.01); *C07K 2317/565* (2013.01); *C07K 2317/569* (2013.01); *C07K 2317/732* (2013.01); *C07K 2317/94* (2013.01)

(58) Field of Classification Search
CPC .. C07K 16/2851; C07K 16/283; C07K 16/32; C07K 2317/31; C07K 2317/33; C07K 2317/524; C07K 2317/53; C07K 2317/565; C07K 2317/569; C07K 2317/732; C07K 2317/94; C07K 2317/52; C07K 2317/64; C07K 2317/71; A61P 35/00

See application file for complete search history.

(56) References Cited

U.S. PATENT DOCUMENTS

| | | |
|---|---|---|
| 5,776,427 A | 7/1998 | Thorpe et al. |
| 5,807,706 A | 9/1998 | Carter et al. |
| 5,863,538 A | 1/1999 | Thorpe et al. |
| 5,959,084 A | 9/1999 | Ring et al. |
| 6,036,955 A | 3/2000 | Thorpe et al. |
| 6,054,297 A | 4/2000 | Carter et al. |
| 6,129,914 A | 10/2000 | Weiner et al. |
| 6,165,464 A | 12/2000 | Hudziak et al. |
| 6,294,167 B1 | 9/2001 | Lindhofer et al. |
| 6,387,371 B1 | 5/2002 | Hudziak et al. |
| 6,399,063 B1 | 6/2002 | Hudziak et al. |
| 6,407,213 B1 | 6/2002 | Carter et al. |
| 6,572,856 B1 | 6/2003 | Taylor et al. |
| 7,112,324 B1 | 9/2006 | Dorken et al. |
| 7,235,641 B2 | 6/2007 | Kufer et al. |
| 7,575,923 B2 | 8/2009 | Dorken et al. |
| 7,635,472 B2 | 12/2009 | Kufer et al. |
| 7,820,166 B2 | 10/2010 | Lanzavecchia |
| 7,879,985 B2 | 2/2011 | Urso et al. |
| 7,951,917 B1 | 5/2011 | Arathoon et al. |
| 8,007,796 B2 | 8/2011 | Baeuerle et al. |
| 8,076,459 B2 | 12/2011 | Hofmeister et al. |
| 8,101,722 B2 | 1/2012 | Kufer et al. |
| 8,236,308 B2 | 8/2012 | Kischel et al. |
| 8,409,577 B2 | 4/2013 | Thompson et al. |
| 8,518,403 B2 | 8/2013 | Hoffmann et al. |
| 8,591,897 B2 | 11/2013 | Bryant |
| 8,658,765 B2 | 2/2014 | Martin, Jr. et al. |
| 8,784,821 B1 | 7/2014 | Kufer et al. |
| 8,796,420 B2 | 8/2014 | Martin, Jr. et al. |
| 8,840,888 B2 | 9/2014 | Nagorsen et al. |

(Continued)

FOREIGN PATENT DOCUMENTS

| | | |
|---|---|---|
| CA | 2990511 A1 | 12/2016 |
| CN | 102378768 A | 3/2012 |

(Continued)

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79): 18294-18302, 2011).*
Shum et al. (J Immunol, 168: 240-252, 2002).*
Kijanka et al. (Eur J Nucl Med Mol Imaging, 40: 1718-1729, 2013).*
Kjellev et al. (Eur. J. Immunol., 37: 1397-1406, 2007).*
Bruhns et al. (Blood, 113(16): 3716-3724, 2009).*

(Continued)

*Primary Examiner* — Nelson B Moseley, II
(74) *Attorney, Agent, or Firm* — Goodwin Procter LLP

(57) ABSTRACT

Multi-specific binding proteins that bind HER2, the NKG2D receptor, and CD 16 are described, as well as pharmaceutical compositions and therapeutic methods useful for the treatment of cancer.

15 Claims, 34 Drawing Sheets

Specification includes a Sequence Listing.

(56) References Cited

U.S. PATENT DOCUMENTS

| | | |
|---|---|---|
| 9,079,969 B2 | 7/2015 | Martin, Jr. et al. |
| 9,102,736 B2 | 8/2015 | Hofmeister et al. |
| 9,127,064 B2 | 9/2015 | Urso et al. |
| 9,150,656 B2 | 10/2015 | Johnson et al. |
| 9,150,663 B2 | 10/2015 | Labrijn et al. |
| 9,200,078 B2 | 12/2015 | Bachmann |
| 9,248,181 B2 | 2/2016 | De Kruif et al. |
| 9,248,182 B2 | 2/2016 | De Kruif et al. |
| 9,273,136 B2 | 3/2016 | Rader et al. |
| 9,587,036 B2 | 3/2017 | Kufer et al. |
| 9,683,053 B2 | 6/2017 | Blein et al. |
| 9,718,893 B2 | 8/2017 | Jung et al. |
| 9,951,145 B2 | 4/2018 | Kim et al. |
| 9,963,513 B2 | 5/2018 | Vu et al. |
| 10,040,853 B2 | 8/2018 | Spies et al. |
| 10,059,765 B2 | 8/2018 | Velardi et al. |
| 10,377,827 B2 | 8/2019 | Swanson et al. |
| 10,526,409 B2 | 1/2020 | Urso et al. |
| 11,124,582 B2 | 9/2021 | Ambrogelly et al. |
| 2002/0103345 A1 | 8/2002 | Zhu |
| 2002/0193569 A1 | 12/2002 | Hanna |
| 2004/0038339 A1 | 2/2004 | Kufer et al. |
| 2004/0052783 A1 | 3/2004 | Weiner et al. |
| 2004/0115198 A1 | 6/2004 | Spies et al. |
| 2005/0037002 A1 | 2/2005 | Velardi et al. |
| 2005/0054019 A1 | 3/2005 | Michaud et al. |
| 2005/0058639 A1 | 3/2005 | Gudas et al. |
| 2005/0158307 A1 | 7/2005 | Spies et al. |
| 2005/0244416 A1 | 11/2005 | Jung |
| 2006/0018899 A1* | 1/2006 | Kao ............... C07K 16/32 424/133.1 |
| 2006/0235201 A1 | 10/2006 | Kischel |
| 2006/0246004 A1 | 11/2006 | Adams et al. |
| 2007/0004909 A1 | 1/2007 | Johnson et al. |
| 2007/0071759 A1 | 3/2007 | Shin et al. |
| 2007/0179086 A1 | 8/2007 | Gliniak et al. |
| 2007/0190063 A1 | 8/2007 | Bahjat et al. |
| 2008/0025975 A1 | 1/2008 | Weiner et al. |
| 2008/0299137 A1 | 12/2008 | Svendsen et al. |
| 2008/0305105 A1 | 12/2008 | Kufer et al. |
| 2009/0142352 A1 | 6/2009 | Jackson et al. |
| 2009/0175867 A1 | 7/2009 | Thompson et al. |
| 2009/0226442 A1 | 9/2009 | Huet et al. |
| 2009/0226466 A1 | 9/2009 | Fong et al. |
| 2009/0252729 A1 | 10/2009 | Farrington et al. |
| 2009/0304693 A1* | 12/2009 | Ghayur ............... A61P 19/04 424/133.1 |
| 2009/0304696 A1 | 12/2009 | Lawson et al. |
| 2010/0009866 A1 | 1/2010 | Prinz et al. |
| 2010/0055034 A1 | 3/2010 | Martin et al. |
| 2010/0056764 A1 | 3/2010 | Urso et al. |
| 2010/0124764 A1 | 5/2010 | Hufton et al. |
| 2010/0174053 A1 | 7/2010 | Johnson et al. |
| 2010/0178298 A1 | 7/2010 | Lindhofer |
| 2010/0260765 A1 | 10/2010 | Barry et al. |
| 2010/0272718 A1 | 10/2010 | Urso et al. |
| 2010/0286374 A1 | 11/2010 | Kannan et al. |
| 2010/0291112 A1 | 11/2010 | Kellner et al. |
| 2011/0008335 A1 | 1/2011 | Velardi et al. |
| 2011/0020273 A1 | 1/2011 | Chang et al. |
| 2011/0044980 A1 | 2/2011 | Ghayur et al. |
| 2011/0054151 A1 | 3/2011 | Lazar et al. |
| 2011/0150870 A1* | 6/2011 | Rader ............... A61P 31/10 424/133.1 |
| 2011/0311535 A1 | 12/2011 | Dranoff et al. |
| 2012/0014957 A1 | 1/2012 | Ghayur et al. |
| 2012/0058082 A1 | 3/2012 | Kaplan et al. |
| 2012/0058906 A1 | 3/2012 | Smider et al. |
| 2012/0093823 A1 | 4/2012 | Van Den Brink et al. |
| 2012/0149876 A1 | 6/2012 | Von Kreudenstein et al. |
| 2012/0171173 A1 | 7/2012 | Ideno et al. |
| 2012/0195900 A1 | 8/2012 | Ghayur et al. |
| 2012/0263722 A1 | 10/2012 | Ghayur et al. |
| 2012/0269723 A1 | 10/2012 | Brinkmann et al. |
| 2012/0294796 A1 | 11/2012 | Johnson et al. |
| 2012/0294857 A1 | 11/2012 | Sentman et al. |
| 2012/0321626 A1 | 12/2012 | Zhou |
| 2012/0328619 A1 | 12/2012 | Fey et al. |
| 2013/0115208 A1 | 5/2013 | Ho et al. |
| 2013/0177555 A1 | 7/2013 | Wilkinson et al. |
| 2013/0209514 A1 | 8/2013 | Gilboa et al. |
| 2013/0216528 A1 | 8/2013 | Cheung et al. |
| 2013/0216544 A1 | 8/2013 | Bachmann |
| 2013/0230525 A1 | 9/2013 | Li et al. |
| 2013/0336977 A1 | 12/2013 | Thompson et al. |
| 2014/0044739 A1 | 2/2014 | Teng et al. |
| 2014/0072579 A1 | 3/2014 | De Kruif et al. |
| 2014/0072581 A1 | 3/2014 | Dixit et al. |
| 2014/0105889 A1 | 4/2014 | Igawa et al. |
| 2014/0112926 A1 | 4/2014 | Liu et al. |
| 2014/0120096 A1 | 5/2014 | Bakker et al. |
| 2014/0127203 A1 | 5/2014 | Thompson et al. |
| 2014/0140999 A1 | 5/2014 | De Kruif et al. |
| 2014/0141022 A1 | 5/2014 | Thompson et al. |
| 2014/0154250 A1 | 6/2014 | Thompson et al. |
| 2014/0154252 A1 | 6/2014 | Thompson et al. |
| 2014/0199294 A1 | 7/2014 | Mimoto et al. |
| 2014/0234342 A1 | 8/2014 | Narni-Mancinelli et al. |
| 2014/0242077 A1 | 8/2014 | Choi et al. |
| 2014/0271617 A1 | 9/2014 | Igawa et al. |
| 2014/0294827 A1 | 10/2014 | Gastwirt et al. |
| 2014/0302064 A1 | 10/2014 | Moore |
| 2014/0363426 A1* | 12/2014 | Moore ............... C07K 16/2803 424/133.1 |
| 2014/0364340 A1 | 12/2014 | Vasquez et al. |
| 2015/0050269 A1 | 2/2015 | Igawa et al. |
| 2015/0056206 A1 | 2/2015 | Zhou |
| 2015/0079088 A1 | 3/2015 | Lowman et al. |
| 2015/0119555 A1 | 4/2015 | Jung et al. |
| 2015/0166636 A1 | 6/2015 | Igawa et al. |
| 2015/0166654 A1 | 6/2015 | Igawa et al. |
| 2015/0175697 A1 | 6/2015 | Bonvini et al. |
| 2015/0175700 A1 | 6/2015 | Lum et al. |
| 2015/0203591 A1 | 7/2015 | Yancopoulos et al. |
| 2015/0210765 A1 | 7/2015 | Roschke et al. |
| 2015/0259431 A1 | 9/2015 | Stemmer et al. |
| 2015/0259434 A1 | 9/2015 | Johnson et al. |
| 2015/0274838 A1 | 10/2015 | Johnson et al. |
| 2015/0299319 A1 | 10/2015 | Velardi et al. |
| 2015/0307617 A1 | 10/2015 | Du et al. |
| 2015/0307628 A1 | 10/2015 | Kim et al. |
| 2015/0329637 A1 | 11/2015 | Urech et al. |
| 2015/0353636 A1* | 12/2015 | Parren ............... C07K 16/40 424/1.53 |
| 2016/0024214 A1 | 1/2016 | Urso et al. |
| 2016/0032009 A1 | 2/2016 | Cheung et al. |
| 2016/0039942 A1 | 2/2016 | Cobbold et al. |
| 2016/0046730 A1 | 2/2016 | Ghayur et al. |
| 2016/0077105 A1 | 3/2016 | Bobrowicz et al. |
| 2016/0090426 A1 | 3/2016 | Zhou et al. |
| 2016/0096892 A1 | 4/2016 | Brogdon et al. |
| 2016/0122432 A1 | 5/2016 | Baty et al. |
| 2016/0159882 A1 | 6/2016 | Landgraf et al. |
| 2016/0159924 A1 | 6/2016 | Padkjaer et al. |
| 2016/0176968 A1 | 6/2016 | Chang et al. |
| 2016/0289341 A1 | 10/2016 | Wu |
| 2016/0326249 A1 | 11/2016 | Ng et al. |
| 2016/0347849 A1 | 12/2016 | Cai et al. |
| 2016/0369002 A1 | 12/2016 | Gauthier et al. |
| 2017/0022291 A1 | 1/2017 | Baruah et al. |
| 2017/0029529 A1 | 2/2017 | Croasdale et al. |
| 2017/0066827 A1 | 3/2017 | Pule et al. |
| 2017/0114141 A1 | 4/2017 | Amann et al. |
| 2017/0233472 A1 | 8/2017 | Barat et al. |
| 2017/0291955 A1 | 10/2017 | Li et al. |
| 2017/0362321 A1 | 12/2017 | Campbell et al. |
| 2017/0368169 A1 | 12/2017 | Loew et al. |
| 2017/0369595 A1 | 12/2017 | Brinkmann et al. |
| 2018/0044415 A1 | 2/2018 | Escarpe et al. |
| 2018/0057608 A1 | 3/2018 | Jung et al. |
| 2018/0105594 A1 | 4/2018 | Urso et al. |
| 2018/0105599 A1 | 4/2018 | Cobbold et al. |
| 2018/0118851 A1 | 5/2018 | Comeau et al. |
| 2018/0237519 A1 | 8/2018 | Caligiuri et al. |

(56) References Cited

U.S. PATENT DOCUMENTS

| | | |
|---|---|---|
| 2018/0273633 A1 | 9/2018 | Jiang et al. |
| 2018/0312592 A1 | 11/2018 | Junutula et al. |
| 2019/0048079 A1 | 2/2019 | Spies et al. |
| 2019/0225702 A1 | 7/2019 | Baeuerle et al. |
| 2019/0359716 A1* | 11/2019 | Chang .................... A61P 13/08 |
| 2019/0375838 A1 | 12/2019 | Chang et al. |
| 2020/0002436 A1 | 1/2020 | Chang et al. |
| 2020/0024353 A1 | 1/2020 | Chang et al. |
| 2020/0048347 A1 | 2/2020 | Miao et al. |
| 2020/0055939 A1 | 2/2020 | Lombana et al. |
| 2020/0095327 A1 | 3/2020 | Chang et al. |
| 2020/0157174 A1 | 5/2020 | Chang et al. |
| 2020/0157226 A1 | 5/2020 | Chang et al. |
| 2020/0157227 A1 | 5/2020 | Chang et al. |
| 2020/0165344 A1 | 5/2020 | Chang et al. |
| 2020/0216544 A1 | 7/2020 | Chang et al. |
| 2020/0231678 A1 | 7/2020 | Chang et al. |
| 2020/0231679 A1 | 7/2020 | Chang et al. |
| 2020/0231700 A1 | 7/2020 | Cheung et al. |
| 2020/0277383 A1 | 9/2020 | Chang et al. |
| 2020/0277384 A1 | 9/2020 | Chang et al. |
| 2020/0376034 A1 | 12/2020 | Chang et al. |
| 2021/0009718 A1 | 1/2021 | Ambrogelly et al. |
| 2021/0032349 A1 | 2/2021 | Dengl et al. |
| 2021/0054082 A1 | 2/2021 | Chang et al. |
| 2021/0070887 A1 | 3/2021 | Ambrogelly et al. |
| 2021/0079102 A1 | 3/2021 | Chang et al. |
| 2021/0101976 A1 | 4/2021 | Chang et al. |
| 2021/0130471 A1 | 5/2021 | Chang et al. |
| 2021/0130474 A1 | 5/2021 | Chang et al. |
| 2021/0130496 A1 | 5/2021 | Chang et al. |
| 2021/0198369 A1 | 7/2021 | Chang et al. |
| 2021/0206859 A1 | 7/2021 | Chang et al. |
| 2021/0214436 A1 | 7/2021 | Chang et al. |
| 2021/0221894 A1 | 7/2021 | Bigelow et al. |
| 2021/0238290 A1 | 8/2021 | Chang et al. |
| 2021/0261668 A1 | 8/2021 | Chang et al. |
| 2021/0292420 A1 | 9/2021 | Chang et al. |
| 2021/0363261 A1 | 11/2021 | Chang et al. |
| 2022/0119534 A1 | 4/2022 | Baruah et al. |
| 2022/0195065 A1 | 6/2022 | Chang et al. |
| 2022/0380459 A1 | 12/2022 | Chang et al. |

FOREIGN PATENT DOCUMENTS

| | | |
|---|---|---|
| CN | 105906722 A | 8/2016 |
| DE | 102013019352 A1 | 9/2015 |
| EP | 627940 A1 | 12/1994 |
| EP | 845998 A1 | 6/1998 |
| EP | 871673 A1 | 10/1998 |
| EP | 1124568 A1 | 8/2001 |
| EP | 1769000 B1 | 4/2007 |
| EP | 2185595 A1 | 5/2010 |
| EP | 2222706 B2 | 9/2010 |
| EP | 2927321 A1 | 10/2015 |
| EP | 2930188 A1 | 10/2015 |
| EP | 2942629 A1 | 11/2015 |
| EP | 2982380 A1 | 2/2016 |
| EP | 2990416 A1 | 3/2016 |
| RU | 2588668 C2 | 7/2016 |
| RU | 2593720 C2 | 8/2016 |
| WO | WO-1988008854 A1 | 11/1988 |
| WO | WO-1989006544 A1 | 7/1989 |
| WO | WO-1996/027011 A1 | 9/1996 |
| WO | WO-2001071005 A2 | 9/2001 |
| WO | WO-2004056873 A1 | 7/2004 |
| WO | WO-2006037960 A2 | 4/2006 |
| WO | WO-2007002905 A1 | 1/2007 |
| WO | WO-2007042573 A2 | 4/2007 |
| WO | WO-2007055926 A1 | 5/2007 |
| WO | WO-2007097812 A2 | 8/2007 |
| WO | WO-2009007124 A1 | 1/2009 |
| WO | WO-2009077483 A1 | 6/2009 |
| WO | WO-2009/089004 A1 | 7/2009 |
| WO | WO-2010017103 A2 | 2/2010 |
| WO | WO-2010080124 A2 | 7/2010 |
| WO | WO-2011014659 A2 | 2/2011 |
| WO | WO-2011075636 A2 | 6/2011 |
| WO | WO-2011109400 A2 | 9/2011 |
| WO | WO-2011/131746 A2 | 10/2011 |
| WO | WO-2011143545 A1 | 11/2011 |
| WO | WO-2012006490 A2 | 1/2012 |
| WO | WO-2012/025530 A1 | 3/2012 |
| WO | WO-2012/032080 A1 | 3/2012 |
| WO | WO-2012034039 A2 | 3/2012 |
| WO | WO-2012058768 A1 | 5/2012 |
| WO | WO-2012125850 A1 | 9/2012 |
| WO | WO-2012158818 A2 | 11/2012 |
| WO | WO-2012162482 A1 | 11/2012 |
| WO | WO-2013013700 A1 | 1/2013 |
| WO | WO-2013036799 A2 | 3/2013 |
| WO | WO-2013092001 A1 | 6/2013 |
| WO | WO-2013192594 A2 | 12/2013 |
| WO | WO-2014001324 A1 | 1/2014 |
| WO | WO-2014012085 A2 | 1/2014 |
| WO | WO-2014079000 A1 | 5/2014 |
| WO | WO-2014/084607 A1 | 6/2014 |
| WO | WO-2014110601 A1 | 7/2014 |
| WO | WO-2014131712 A1 | 9/2014 |
| WO | WO-2014144763 A2 | 9/2014 |
| WO | WO-2014145806 A2 | 9/2014 |
| WO | WO-2014159940 A1 | 10/2014 |
| WO | WO-2014165818 A2 | 10/2014 |
| WO | WO-2014198748 A1 | 12/2014 |
| WO | WO-2015009856 A2 | 1/2015 |
| WO | WO-2015036582 A2 | 3/2015 |
| WO | WO-2015036606 A1 | 3/2015 |
| WO | WO-2015063187 A1 | 5/2015 |
| WO | WO-2015070061 A1 | 5/2015 |
| WO | WO-2015077891 A1 | 6/2015 |
| WO | WO-2015089344 A1 | 6/2015 |
| WO | WO-2015095412 A1 | 6/2015 |
| WO | WO-2015095539 A1 | 6/2015 |
| WO | WO-2015095972 A1 | 7/2015 |
| WO | WO-2015/150447 A1 | 10/2015 |
| WO | WO-2015153765 A1 | 10/2015 |
| WO | WO-2015153912 A1 | 10/2015 |
| WO | WO-2015158636 A1 | 10/2015 |
| WO | WO-2015169781 A1 | 11/2015 |
| WO | WO-2015181282 A1 | 12/2015 |
| WO | WO-2015184203 A1 | 12/2015 |
| WO | WO-2015184207 A1 | 12/2015 |
| WO | WO-2015197582 A1 | 12/2015 |
| WO | WO-2015197593 A1 | 12/2015 |
| WO | WO-2015197598 A2 | 12/2015 |
| WO | WO-2016011571 A1 | 1/2016 |
| WO | WO-2016023909 A1 | 2/2016 |
| WO | WO-2016025880 A1 | 2/2016 |
| WO | WO-2016028672 A1 | 2/2016 |
| WO | WO-2016032334 A1 | 3/2016 |
| WO | WO-2016070959 A1 | 5/2016 |
| WO | WO-2016090278 A2 | 6/2016 |
| WO | WO-2016097408 A1 | 6/2016 |
| WO | WO-2016100533 A2 | 6/2016 |
| WO | WO-2016109774 A1 | 7/2016 |
| WO | WO-2016115274 A1 | 7/2016 |
| WO | WO-2016122701 A1 | 8/2016 |
| WO | WO-2016134371 A2 | 8/2016 |
| WO | WO-2016135041 A1 | 9/2016 |
| WO | WO-2016135066 A1 | 9/2016 |
| WO | WO-2016142768 A1 | 9/2016 |
| WO | WO-2016146702 A1 | 9/2016 |
| WO | WO-2016161390 A1 | 10/2016 |
| WO | WO-2016164369 A2 | 10/2016 |
| WO | WO-2016164637 A1 | 10/2016 |
| WO | WO-2016166139 A1 | 10/2016 |
| WO | WO-2016184592 A1 | 11/2016 |
| WO | WO-2016187220 A2 | 11/2016 |
| WO | WO-2016191305 A1 | 12/2016 |
| WO | WO-2016196237 A1 | 12/2016 |
| WO | WO-2016201300 A1 | 12/2016 |
| WO | WO-2016201389 A2 | 12/2016 |
| WO | WO-2016207273 A2 | 12/2016 |
| WO | WO-2016207278 A1 | 12/2016 |

(56) References Cited

FOREIGN PATENT DOCUMENTS

| | | |
|---|---|---|
| WO | WO-2017005732 A1 | 1/2017 |
| WO | WO-2017008169 A1 | 1/2017 |
| WO | WO-2017011342 A1 | 1/2017 |
| WO | WO-2017021349 A1 | 2/2017 |
| WO | WO-2017048824 A1 | 3/2017 |
| WO | WO-2017075432 A2 | 5/2017 |
| WO | WO-2017079694 A2 | 5/2017 |
| WO | WO-2017081190 A1 | 5/2017 |
| WO | WO-2017083545 A1 | 5/2017 |
| WO | WO-2017114694 A1 | 7/2017 |
| WO | WO-2017124002 A1 | 7/2017 |
| WO | WO-2017125897 A1 | 7/2017 |
| WO | WO-2017143406 A1 | 8/2017 |
| WO | WO-2017165464 A1 | 9/2017 |
| WO | WO-2017165683 A1 | 9/2017 |
| WO | WO-2017177337 A1 | 10/2017 |
| WO | WO-2017180813 A1 | 10/2017 |
| WO | WO-2017211873 A1 | 12/2017 |
| WO | WO-2017218707 A2 | 12/2017 |
| WO | WO-2018045090 A1 | 3/2018 |
| WO | WO-2018098365 A2 | 5/2018 |
| WO | WO-2018119171 A1 | 6/2018 |
| WO | WO-2018148445 A1 | 8/2018 |
| WO | WO-2018148447 A1 | 8/2018 |
| WO | WO-2018148566 A1 | 8/2018 |
| WO | WO-2018148610 A1 | 8/2018 |
| WO | WO-2018152518 A1 | 8/2018 |
| WO | WO-2018157147 A1 | 8/2018 |
| WO | WO-2018201051 A1 | 11/2018 |
| WO | WO-2019051308 A1 | 3/2019 |

OTHER PUBLICATIONS

Felices et al. (2016) "Generation of BiKEs and TriKEs to Improve NK cell-Mediated Targeting of Tumor Cells," Natural Killer Cells: Methods and Protocols, Methods in Molecular Biology 1441:333-346.

Gantke et al. (2016) "Trispecific Antibodies for Selective CD16A-Directed NK-Cell Engagement in Multiple Myeloma," Blood 128(22):4513.

Gantke et al. (2017) "Trispecific antibodies for CD16A-directed NK cell engagement and dual-targeting of tumor cells," Protein Engineering, Design & Selection 38(9):673-684.

Gauthier et al. (2019) "Multifunctional Natural Killer Cell Engagers Targeting NKp46 Trigger Protective Tumor Immunity," Cell 177(7):1701-1713.

Gooden et al. (2012) "Infiltrating CTLs are bothered by HLA-E on tumors," OncoImmunology, 1(1):92-93.

Kluge et al. (2017) "EGFR/CD16A TandAbs are efficacious NK-cell engagers with favorable biological properties which potently kill EGFR(+) tumors with and without Ras mutation," Cancer Research 77(13 Suppl.):Abstract 3641.

Madlener et al. (2010) "A Bispecific Protein Targeting the NKG2D Receptor on Natural Killer Cells: In Vitro and In Vivo activity of ULBP2-CEA," Blood 116(21):2095.

McWilliams, et al. (2016) "Targeting the Tumor Evasion Interaction of NKG2A and Its Ligand HLA-E Increases Natural-Killer Cell Activity in Chronic Lymphocytic Leukemia," Blood 1289-1291.

Myers et al. (2021) "Exploring the NK cell platform for cancer immunotherapy," Nature Reviews Clinical Oncology 18(2):85-100.

Nie et al. (2020) "Biology drives the discovery of bispecific antibodies as innovative therapeutics," Antibody Therapeutics 3(1):18-62.

Rothe et al. (2013) "The Bispecific Immunoligand ULBP2-aCEA Redirects Natural Killer Cells to Tumor Cells and Reveals Potent Anti-Tumor Activity Against Colon Carcinoma," Int. J. Cancer 134(12):2829-2840.

Vyas et al. (2016) "Mono- and dual-targeting triplebodies activate natural killer cells and have anti-tumor activity in vitro and in vivo against chronic lymphocytic leukemia," Oncoimmunology 5(9):p. e1211220.

Ahmad et al. (2012) "scFv antibody: principles and clinical application," Clinical and Developmental Immunology 2012: 1-16.

Averdam et al. (2009) "A Novel System of Polymorphic and Diverse NK Cell Receptors in Primates," PLoS Genetics 5 (10): e1000688.

Busfield et al. (2014) "Targeting of acute myeloid leukemia in vitro and in vivo with an anti-CD123 mAb engineered for optimal ADCC," Leukemia 28 (11): 2213-2221.

Chu, S. et al. (2014) "Immunotherapy with Long-Lived Anti-CD123 x Anti-CD3 Bispecific Antibodies Stimulates Potent T Cell-Mediated Killing of Human AML Cell Lines and of CD123+ Cells in Monkeys: A Potential Therapy for Acute Myelogenous Leukemia 11," Blood 124(21).

Glas et al. (1997) "Analysis of rearranged immunoglobulin heavy chain variable region genes obtained from a bone marrow transplant (BMT) recipient," Clinical & Experimental Immunology 107 (2):372-380.

Gleason et al. (2012) "Bispecific and Trispecific Killer Cell Engagers Directly Activate Human NK Cells through CD16 Signaling and Induce Cytotoxicity and Cytokine Production," Molecular Cancer Therapeutics 11 (12): 2674-2684.

Gleason et al. (2014) "CD16xCD33 bispecific killer cell engager (BIKE) activates NK cells against primary MDS and MDSC CD33+ targets," Blood 123 (19):3016-3026.

Kellner et al. (2012) "Fusion proteins between ligands for NKG2D and CD20-directed single-chain variable fragments sensitize lymphoma cells for natural killer cell-mediated lysis and enhance antibody-dependent cellular cytotoxicity," Leukemia 26:830-834.

Kellner et al. (2016) "Enhancing natural killer cell-mediated lysis of lymphoma cells by combining therapeutic antibodies with CD20-specific immunoligands engaging NKG2D or NKp30," OncoImmunology 5(1):e1058459-1-e1058459-12.

Kwong et al. (2008) "Generation, affinity maturation, and characterization of a human anti-human NKG2D monoclonal antibody with dual antagonistic and agonistic activity," Journal of Molecular Biology 384 (5): 1143-1156.

Lin et al. (2013) "CD4+ NKG2D+ T cells induce NKG2D down-regulation in natural killer cells in CD86-RAE-1 E transgenic mice," Immunology 141 (3): 401-415.

Liu et al. (2017) "Fc engineering for Developing Therapeutic Bispecific Antibodies and Novel Scaffolds," Frontiers in Immunology 8, 38: 1-15.

Petricevic et al. (2013) "Trastuzumab mediates antibody-dependent cell-mediated cytotoxicity and phagocytosis to the same extent in both adjuvant and metastatic HER2/neu breast cancer patients," Journal of Translational Medicine 11 (307).

Raab et al. (2014) "Fc-Optimized NKG2D-Fc Constructs Induce NK Cell Antibody-Dependent Cellular Cytotoxicity Against Breast Cancer Cells Independently of HER2/neu Expression Status," Journal of Immunology 193(8): 4261-72.

Romee et al. (2013) "NK cell CD16 surface expression and function is regulated by a disintegrin and metalloprotease-17 (ADAM17)," Blood 121(18): 3599-608.

Smits et al. (2016) "Designing multivalent proteins based on natural killer cell receptors and their ligands as immunotherapy for cancer," Expert Opinion on Biological Therapy 16 (9):1105-1112.

Spear et al. (2013) "NKG2D ligands as therapeutic targets," Cancer Immunology 13:8.

Steigerwald et al. (2009) "Human IgG1 antibodies antagonizing activating receptor NKG2D on natural killer cells," mAbs 1(2): 115-127.

Steinbacher et al. (2015) "An Fc-optimized NKG2D-immunoglobulin G fusion protein for induction of natural killer cell reactivity against leukemia," International Journal of Cancer 136(5): 1073-1084.

Vaks et al. (2018) "Design Principles for Bispecific IgGs, Opportunities and Pitfalls of Artificial Disulfide Bonds," Antibodies 7(27): 1-28.

Wang et al. (2016) "A bispecific protein rG7S-MICA recruits natural killer cells and enhances NKG2D-mediated immunosurveillance against hepatocellular carcinoma," Cancer Letters 372:166-178.

(56) References Cited

OTHER PUBLICATIONS

Written Opinion for International Application No. PCT/US2018/018771 dated Apr. 25, 2018.
Yeap et al. (2016) "CD16 is indispensable for antibody dependent cellular cytotoxicity by human monocytes," *Scientific Reports* 6:34310.
Young et al. (1995) "Thermal stabilization of a single-chain Fv antibody fragment by introduction of a disulphide bond," *FEBS Letters* 377 (2): 135-139.
U.S. Appl. No. 16/486,722, filed Aug. 16, 2019.
PCT/US2019/030946, May 6, 2019.
PCT/US2019/032582, May 16, 2019.
PCT/US2019/034186, May 28, 2019.
PCT/US2019/045561, Aug. 7, 2019.
PCT/US2019/045632, Aug. 8, 2019.
PCT/US2019/045723, Aug. 8, 2019.
PCT/US2019/045677, Aug. 8, 2019.
Cai et al. (2014) "Autonomous Stimulation of Cancer Cell Plasticity by the Human NKG2D Lymphocyte Receptor Coexpressed with Its Ligands on Cancer Cells," *PLOS ONE* 9(10):e108942.
Cho et al. (2010) "Delivery of NKG2D Ligand Using an Anti-HER2 Antibody-NKG2D Ligand Fusion Protein Results in an Enhanced Innate and Adaptive Antitumor Response," *Cancer Research* 70(24):10121-10130.
Ding et al. (2018) "Fusion Proteins of NKG2D/NKG2DL in Cancer Immunotherapy," *International Journal of Molecular Sciences* 19(1):177.
Germain et al. (2005) "MHC Class I-Related Chain a Conjugated to Antitumor antibodies Can Sensitize Tumor Cells to Specific Lysis by Natural Killer Cell," *Clinical Cancer Research* US 11(20):7516-7522.
Hezareh et al. (2001) "Effector Function Activities of a Panel of Mutants of a Broadly Neutralizing Antibody against Human Immunodeficiency Virus Type 1," *Journal of Virology* 75(24):12161-12168.
Jachimowicz et al. (2011) "Induction of In Vitro and In Vivo NK Cell Cytotoxicity Using High-Avidity Immunoligands Targeting Prostate-Specific Membrane Antigen in Prostate Carcinoma," *Mol Cancer Thera*, 10(6):1036-1045.
Kellner et al. (2013) "Promoting natural killer cell functions by recombinant immunoligands mimicking an induced self phenotype," *Oncoimmunology* 2(6):e24481.
Morvan et al. (2016)."NK cells and cancer: you can teach innate cells new tricks" *Nat Rev Cancer* 16(1):7-19.
Nagasaki et al. (2014) "Interleukin-6 released by colon cancer-associated fibroblasts is critical for tumour angiogenesis: anti-interleukin-6 receptor antibody suppressed angiogenesis and inhibited tumour-stroma interaction," *British Journal of Cancer* 110(2):469-478.
Schuster et al. (2015) "Immunotherapy with the trifunctional anti-CD20 x anti-CD3 antibody FBTA05 (Lymphomun) in paediatric high-risk patients with recurrent CD20-positive B cell malignancies," *British Journal of Haematology* 169(1):90-102.
Strong (2002) "Asymmetric ligand recognition by the activating natural killer cell receptor NKG2D, a symmetric homodimer," *Molecular Immunology* 38(14):1029-1037.
Tay et al. (2016) "TriKEs and BiKEs join CARs on the cancer immunotherapy highway," *Human Vaccines & Immunotherapeutics* 12(11):2790-2796.
Von Strandmann et al. (2006) "A novel bispecific protein (ULBP2-BB4) targeting the NKG2D receptor on natural killer (NK) cells and CD138 activates NK cells and has potent antitumor activity against human multiple myeloma in vitro and in vivo," *Blood* 107(5):1955-1962.
Weiss-Steider et al. (2011) "Expression of MICA, MICB and NKG2D in human leukemic myelomonocytic and cervical cancer cells," *Journal of Experimental & Clinical Cancer Research* 30(1):37.
Xu et al. (2019) "A VEGFR2-MICA bispecific antibody activates tumor-infiltrating lymphocytes and exhibits potent anti-tumor efficacy in mice," *Cancer Immunology Immunotherapy* 68(9):1429-1441.
Chen X et al. (2013) "Fusion protein linkers: property, design and functionality" *Advanced drug delivery reviews*, 65(10):1357-1369.
Colman P. M. (1994) "Effects of amino acid sequence changes on antibody-antigen interactions" *Research in Immunology* 145(1):33-36.
Dickopf et al. (2020) "Format and geometries matter: Structure-based design defines the functionality of bispecific antibodies," *Computational and Structural Biotechnology Journal* 18:1221-1227.
Junttila et al. (2014) "Antitumor Efficacy of a Bispecific Antibody That Targets HER2 and Activates T Cells," *Cancer Research* 74(19):5561-5571.
Maeda Y. et al. (1997) "Engineering of Functional Chimeric Protein G-Vargula Luciferase" *Analytical biochemistry*, 249(2):147-152.
Pakula et al. (1989) "Genetic Analysis of Protein Stability and Function," *Annu. Rev. Genet.* 23:289-310.
Roda-Navarro et al. (2020) "Understanding the Spatial Topology of Artificial Immunological Synapses Assembled in T Cell-Redirecting Strategies: A Major Issue in Cancer Immunotherapy," *Frontiers in Cell and Developmental Biology* 7:1-5.
Safdari Y. et al. (2013) "Antibody humanization methods—a review and update" *Biotechnology and Genetic Engineering Reviews*, 29(2):175-186.
Shen J. et al. (2006) "Single variable domain-IgG fusion: a novel recombinant approach to Fc domain-containing bispecific antibodies" *Journal of Biological Chemistry*, 281(16):10706-10714.
Stamova et al. (2011) "Simultaneous engagement of the activatory receptors NKG2D and CD3 for retargeting of effector cells to CD33-positive malignant cells," *Leukemia* 25:1053-1056.
Teplyakov A. et al. (2014) "Antibody modeling assessment II. Structures and models" *Proteins: Structure, Function, and Bioinformatics*, 82(8):1563-1582.
Torres M. et al. (2008) "The immunoglobulin constant region contributes to affinity and specificity" *Trends in immunology*, 29(2):91-97.
Xu et al. (2014) "Production of bispecific antibodies in "knobs-into-holes" using a cell-free expression system," *mAbs* 7(1)231-242.
U.S. Appl. No. 16/615,203, filed Nov. 20, 2019.
PCT/US2020/048500, Aug. 28, 2020.
PCT/US2020/055497, Oct. 14, 2020.
Bendayan et al. (1995) "Possibilities of False Immunocytochemical Results Generated by The Use of Monoclonal Antibodies: The Example of the Anti-proinsulin Antibody," *J. Histochem. Cytochem.* 43:881-886.
Bostrom, et al. (2009) "Improving Antibody Binding Affinity and Specificity for Therapeutic Development," *Methods and Protocols* 525:353-376.
Brinkmann et al. (2017) "The making of bispecific antibodies," *MABS* 9(2)182-212.
Bryceson et al. (2006) "Synergy among receptors on resting NK cells for the activation of natural cytotoxicity and cytokine secretion," *Blood* 107(1):159-166.
Casset et al. (2003) "A peptide mimetic of an anti-CD4 monoclonal antibody by rational design," *Biochemical and Biophysical Research Communications* 307:198-205.
Chen et al. (1995) "Enhancement and destruction of antibody function by somatic mutation: unequal occurrence is controlled by V gene combinatorial associations," *The EMBO Journal* 14(12):2784-2794.
Chen et al. (1999) "Selection and Analysis of an Optimized Anti-VEGF Antibody: Crystal Structure of an Affinity-matured Fab in Complex with Antigen," *J. Mol. Biol.* 293:865-881.
Choi et al. (2013) "A Heterodimeric Fc-Based Bispecific Antibody Simultaneously Targeting VEGFR-2 and Met Exhibits Potent Antitumor Activity," *Mol Cancer Ther*, 12(12):2748-2759.
De Pascalis et al. (2002) "Grafting of "Abbreviated" Complementarity-Determining Regions Containing Specificity-Determining Residues Essential for Ligand Contact to Engineer a Less Immunogenic Humanized Monoclonal Antibody," *The Journal of Immunology* 169:3076-3084.

(56) References Cited

OTHER PUBLICATIONS

Edwards et al. (2003) "The Remarkable Flexibility of the Human Antibody Repertoire; Isolation of Over One Thousand Different Antibodies to a Single Protein, BLyS," *J. Mol. Biol.* 334:103-118.
Gonzales, et al. (2005) "Minimizing the Immunogenicity of Antibodies for Clinical Application," *Tumour Biol.* 26(1):31-43.
Henry et al. (2017) "Stability-Diversity Tradeoffs Impose Fundamental Constraints on Selection of Synthetic Human $V_H/V_L$ Single-Domain Antibodies from In Vitro Display Libraries," *Frontiers in Immunology*, 8:1-15.
Hoseini et al. (2017) "Acute myeloid leukemia targets for bispecific antibodies," *Blood Cancer Journal* 7(2):e522-e522.
Kim et al. (2014) "Mutational approaches to improve the biophysical properties of human single-domain antibodies," *Biochimica et Biophysica Acta*, 1844:1983-2001.
Koerner et al. (2015) "Induction of NK and T Cell Immune Responses Against Leukemia Cells By Bispecific NKG2D-CD16 and -CD3 Fusion Proteins," *Blood* 126(23):2558, Abstract 606.
Kranz et al. (1981) "Restricted reassociation of heavy and light chains from hapten-specific monoclonal antibodies," *Pro. Natl. Acad. Sci. USA* 78(9):5807-5811.
Krieg et al. (2005) "Functional Analysis of B and T Lymphocyte Attenuator Engagement on CD4+ and CD8+ T Cells," *The Journal of Immunology* 175(10):6420-6427.
Lamminmäki et al. (2001) "Crystal Structure of a Recombinant Anti-estradiol Fab Fragment in Complex with 17β-Estradiol," *The Journal of Biological Chemistry* 276(39):36687-36694.
Lloyd et al. (2009) "Modelling the human immune response: performance of a 1011 human antibody repertoire against a broad panel of therapeutically relevant antigens," *Protein Engineering, Design and Selection* 22(3):159-168.
Lund et al. (1996) "Multiple interactions of IgG with its core oligosaccharide can modulate recognition by complement and human Fc gamma receptor I and influence the synthesis of its oligosaccharide chains," *J. Immunol* 157:4963-4969.
MacCallum et al. (1996) "Antibody-antigen Interactions: Contact Analysis and Binding Site Topography," *J. Mol. Biol.* 262:732-745.
Maeda et al. (2015) "New antibody modification technology and its application to antibody drugs," Farumashia 51(5):424-428.
Morris "Epitope Mapping of Protein Antigens by Competition ELISA," The Protein Protocols Handbook, Totowa, NJ, Humana Press, (Jan. 1, 1996):595-600.
Padlan et al. (1989) "Structure of an antibody-antigen complex: Crystal structure of the HyHEL-10 Fab-lysozyme complex," *Pro. Natl. Acad. Sci. USA* 86:5938-5942.
Paul et al. (1993) "Fundamental Immunology," (textbook) 292-295.
Portolano et al. (1993) "Lack of promiscuity in autoantigen-specific H and L chain combinations as revealed by human H and L chain roulette," *J. Immunol.* 15(30):880-887.
Powers et al. (2016) "Abstract 1407: FPA 144, a therapeutic monoclonal antibody targeting the FGFR2b receptor, promotes antibody dependent cell-mediated cytotoxicity and stimulates sensitivity to PD-1 in the 4T1 syngeneic tumor model," *Cancer Research* 4 pages.
Rudikoff et al. (1982) "Single amino acid substitution altering antigen-binding specificity," *Pro. Natl. Acad. Sci USA* 79:1979-1983.
Schroeder et al. (2010) "Structure and Function of Immunoglobulins," *J Allergy Clin Immunol* 125:S41-S52.
Stein et al. (2012) "Natural Killer (NK)- and T-Cell Engaging Antibody-Derived Therapeutics," *Antibodies* 1:88-123.
Vajdos et al. (2002) "Comprehensive Functional Maps of the Antigen-binding Site of an Anti-ErbB2 Antibody Obtained with Shotgun Scanning Mutagenesis," *J. Mol. Biol.* 320:415-428.
Vallera et al. (2016) "IL 15 Trispecific Killer Engagers (TriKE) Make Natural Killer Cells Specific to CD33+ Targets While Also Inducing Persistence, In Vivo Expansion, and Enhanced Function," *Clin Cancer Res*, 22(14):3440-50.
Wang et al. (2018) "IgG Fc engineering to modulate antibody effector functions," *Protein Cell* 9(1):63-73.
Wu et al. (1999) "Humanization of a Murine Monoclonal Antibody by Simultaneous Optimization of Framework and CDR Residues," *J. Mol. Biol.* 294:151-162.
Yan et al. (2014) "Construction of a synthetic phage-displayed Nanobody library with CDR3 regions randomized by trinucleotide cassettes for diagnostic applications," *Journal of Translational Medicine* 12:343 (12 pages).
Zhang et al. (2021) "Bispecific antibody-mediated redirection of NKG2D-CAR natural killer cells facilitates dual targeting and enhances antitumor activity," *Journal for ImmunoTherapy of Cancer*; 9:e002980. doi:10.1136/jitc-2021-002980.
Akbar et al. (2021) "A compact vocabulary of paratope-epitope interactions enables predictability of antibody-antigen binding," *Cell Reports* 34:108856 21 pages.
Altshuler et al. (2010) "Generation of Recombinant Antibodies and Means for Increasing Their Affinity," *Biochemistry* (Moscow) 75(13):1584-1605.
Berenbaum (1977) "Synergy, additivism and antagonism in immunosuppression," Clin. Exp. Immunol. 28:1-18.
Berenbaum (1989) "What is Synergy?" Pharmacological Reviews 41:93-141.
Boltz (2011) "Bi-specific Aptamers mediating Tumour Cell Lysis," Dissertation, M.Sc. Molekulare Biotechnologie, Technische Universität Darmstadt, pp. 1-133.
Bost et al. (1988) "Antibodies Against a Peptide Within The HIV Envelope Protein Crossreacts With Human Interleukin-2," Immunological Investigations 17(6&7):577-586.
Bowen et al. (2016) "Revisiting the Immunoglobulin Intramolecular Signaling Hypothesis," *Trends Immunol.* 37(11):721-723.
Branca et al. (2018) "Nature Biotechnology's academic spinouts of 2017," *Nature Biotechnology* 36(4):297-306.
El-Amine et al. (2002) "In vivo induction of tolerance by an Ig peptide is not affected by the deletion of FcR or a mutated IgG Fc fragment," *International Immunology* 14(7):761-766.
Germain et al. (2008) "Redirecting NK cells mediated tumor cell lysis by a new recombinant bifunctional protein," *Protein Engineering, Design & Selection* 21(11):665-672.
Hasegawa et al. (2017) "Single amino acid substitution in LC-CDR1 induces Russell body phenotype that attenuates cellular protein synthesis through eIF2α phosphorylation and thereby downregulates IgG secretion despite operational secretory pathway traffic," *MABS* 9(5):854-873.
Hlavacek et al. 1999 "Steric Effects on Multivalent Ligand-Receptor Binding: Exclusion of Ligand Sites by Bound Cell Surface Receptors," *Biophysical Journal* 76:3031-3043.
Jonnalagadda et al. (2015) "Chimeric Antigen Receptors With Mutated IgG4 Fc Spacer Avoid Fc Receptor Binding and Improve T Cell Persistence and Antitumor Efficacy," *Molecular Therapy* 23(4):757-768.
Kaur et al. (2015) "Applications of In Vitro-In Vivo Correlations in Generic Drug Development: Case Studies," *The AAPS Journal* 17(4):1035-1039; doi: 10.1208/s12248-015-9765-1.
Kunik, et al. (2012) "Structural consensus among antibodies defines the antigen binding site," *PLoS Comput Biol.* 8(2):e1002388.
Lippow et al. (2007) "Computational design of antibody-affinity improvement beyond in vivo maturation," *Nature Biotechnology* 25(10):1171-1176.
Lo et al. (2021) "Conformational epitope matching and prediction based on protein surface spiral features," *BMC Genomics* 22(Suppl 2):116 16 pages.
Mandelboim et al. (1999) "Human CD16 as a lysis receptor mediating direct natural killer cell cytotoxicity," *PNAS USA* 96(10):5640-5644; doi: 10.1073/pnas.96.10.5640.
Marks et al. (2020) "How repertoire data are changing antibody science," *J. Biol. Chem.* 295(29):9823-9837.
Raulet (2003) "Roles of the NKG2D immunoreceptor and its ligands," *Nature: Reviews Immunology* 3:781-790; doi: 10.1038/nri1199.
Roell et al. (2017) "An Introduction to Terminology and Methodology of Chemical Synergy—Perspectives from Across Disciplines," *Frontiers in Pharmacology: Cancer Molecular Targets and Therapeutics* 8:1-11.

(56) References Cited

OTHER PUBLICATIONS

Rosano et al. (2014) "Recombinant protein expression in *Escherichia coli*: advances and challenges" Frontiers in Microbiology 5(172):17 pages.
Sazinsky et al. (2008) "Aglycosylated immunoglobulin $G_1$ variants productively engage activating Fc receptors," *Proceedings of the National Academy of Sciences* 105(51)20167-20172.
Singer et al. (1998) "Genes and Genomes," Moscow, "Mir" 1:63-64. Concise description of relevance attached (1 page).
Sulea et al. (2018) "Application of Assisted Design of Antibody and Protein Therapeutics (ADAPT) improves efficacy of a *Clostridium difficile* toxin A single-domain antibody," 8:2260 11 pages.
Tallarida (2000) "Drug Synergism and Dose Effect Analysis," Ed. Chapman & Hall pp. 1-71.
Thakur et al. (2018) "Bispecific antibody based therapeutics: Strengths and challenges," Blood Review 32:339-347.
Vajda et al. (2021) "Progress toward improved understanding of antibody maturation," *Current Opinion in Structural Biology* 67:226-231.
Wark et al. (2006) "Latest technologies for the enhancement of antibody affinity", *Advanced Drug Delivery Reviews* 58(5-6):657-670.
U.S. Appl. No. 16/483,572, filed Aug. 5, 2019.
U.S. Appl. No. 16/486,570, filed Aug. 16, 2019.
U.S. Appl. No. 16/488,395, filed Aug. 23, 2019.
U.S. Appl. No. 17/876,855, filed Jul. 29, 2022.
U.S. Appl. No. 16/638,559, filed Feb. 12, 2020.
U.S. Appl. No. 16/644,585, filed Mar. 5, 2020.
U.S. Appl. No. 16/971,104, filed Aug. 19, 2020.
PCT/US2021/044737, Aug. 5, 2021.
Affimed, Affimed Enters Into Collaboration With Merck to Evaluate AFM13 in Combination With . . . Retreived < U RL:https ://www.affimed.com/affi med-enters-into-collaboration-with-merck-to-evaluate-afm 13-i n-combination-with-keytruda-pembrolizumab-for-patients-with-hodgkin-lymphoma/>[retrieved on Feb. 1, 2023] Jan. 25, 2016.
Atwell et al. (1989) "Stable Heterodimers from Remodeling the Domain Interface of a Homodimer using a Phage Display Library," J Mol Biol 270:26-35.
Baek et al. (2014) "Construction of a Large Synthetic Human Fab Antibody Library on Yeast Cell Surface by Optimized Yeast Mating," J Microbial Biotechnol 24(3):408-420.
Brown et al. (1996) "Tolerance of single, but not multiple, amino acid replacements in antibody VH CDR 2: a means of minimizing B cell wastage from somatic hypermutation?," Journal of Immunology, 156: 3285-3291.
Chan et al. (2010) "Therapeutic antibodies for autoimmunity and inflammation," Nature Reviews 10:301-316.
Choi et al. (2015) "Crystal structures of immunoglobulin Fc heterodimers reveal the molecular basis for heterodimer formation," Molecular Immunology 65(2):377-83.
Choi et al. (2015) "Engineering of Immunoglobulin Fc Heterodimers Using Yeast Surface-Displayed Combinatorial Fc Library Screening," PloS One. Dec. 16, 2015; 10(12);e0145349; pp. 1-20.
Cunningham et al. (1969) "Subgroups of Amino Acid Sequences in the Variable Regions of Immunoglobulin Heavy Chains," Proc Natl Acad Sci USA 64(3):997-1003.
Dahlberg et al. (2015) "Natural Killer Cell-Based Therapies Targeting Cancer: Possible Strategies to Gain and sustain Anti-Tumor Activity" Frontiers In Immunology 6(Article 605):19 pages.
Davis et al. (2010) "SEEDbodies: Fusion Proteins Based on Strand-Exchange Engineered Domain (SEED) CH3 Heterodimers in an Fe Analogue Platform for Asymmetric Binders or Immunofusions and Bispecific Antibodies," Protein Eng Des Sel 23(4):195-202.
Elliott et al. (2014) "Antiparallel conformation of knob and hole aglycosylated half-antibody homodimers is mediated by a CH2—CH3 hydrophobic interaction", J. Mol. Biol., 426(9):1947-57.
Feng et al. (2011) "Design, Expression and Characterization of a Soluble Single-Chain Functional Human Neonatal Fc Receptor," Protein Expr Purif 79(1):66-71.
Gunasekaran et al. (2010) "Enhancing Antibody Fc Heterodimer Formation through Electrostatic Steering Effects: Applications to Bispecific Molecules and Monovalent IgG," J Biol Chem 285(25):19637-46.
Ha et al. (2016) "Immunoglobulin Fc Heterodimer Platform Technology: From Design to Applications in Therapeutic Antibodies and Proteins," Front Immunol. 7:394, 16 pages.
Herold et al. (2017) "Determinants of the assembly and function of antibody variable domains," Scientific Reports, 7:12276.
Holliger et al. (2005) "Engineered antibody fragments and the rise of single domains," Nat Biotechnol 23(9): 1126-36.
Klein et al. (2012) "Progress in overcoming the chain association issue in bispecific; heterodimeric IgG antibodies," MaBs 4(6):653-663.
Lewis et al. (2014) "Generation of bispecific IgG antibodies by structure-based design of an orthogonal Fab interface," Nat Biotechnol 32(2):191-98.
Long et al. (2013) "Controlling NK Cell Responses: Integration of Signals for Activation and Inhibition," Annu Rev Immunol. 2013 ; 31: 10.1146/annurev-immunol-020711-075005.
Maelig et al. (2016) "NK cells and cancer: you can teach innate cells new tricks", Nature Reviews Cancer, 16(1):7-19.
Merchant et al. (1998), "An efficient route to human bispecific IgG," Nature Biotechnology 16, 677-681 doi : 10.1038/nbt0798-677.
Miller et al. (2003) "Design, Construction, and in Vitro Analyses of Multivalent Antibodies," J Immunol 170(9):4854-61.
Mimoto et al. (2014) "Crystal structure of a novel asymmetrically engineered Fc variant with improved affinity for FcyRs," Mo/ Immunol 58(1):132-38.
Moore et al. (2011) "A novel bispecific antibody format enables simultaneous bivalent and monovalent co-engagement of distinct target antigens," mAbs 3:6, 546-557; Nov./Dec. 2011, Landes Bioscience, DOI: 10.4161/mabs.3.6.18123.
Muda et al. (2011) "Therapeutic assessment of SEED: a new engineered antibody platform designed to generate mono- and bispecific antibodies," Protein Eng Des Se/ 24(5):447-54.
Muller et al. (2015) "Trastuzumab emtansine (T-DM1) renders HER2+ breast cancer highly susceptible to CTLA-4/PD-1 blockade," Sci. Transl. Med. 7(315):1-14.
Muntasell et al. (2017) "Targeting NK-cell checkpoints for cancer immunotherapy," Current Opinion in Immunology 45:73-81.
Parsons et al. (2016) "NKG2D Acts as a Co-Receptor for Natural Killer Cell-Mediated Anti-HIV-1 Antibody-Dependent Cellular Cytotoxicity," AIDS Research and Human Retroviruses 32(10-11) 1089-1096.
Rabia et al. (2018) "Understanding and overcoming trade-offs between antibody affinity, specificity, stability and solubility" Biochem Eng J. 137:365-374.
Ridgway et al. (1996) "'Knobs-into-Holes' engineering of antibody Ch3 domains for heavy chain heterodimerization," Protein Engineering 9(7):617-21.
Singer et al. (1998) "Genes and Genomes," Moscow, "Mir" 1:63-64.
Sondermann et al. (2000) "The 3.2-Å crystal structure of the human IgG1 Fc fragment—Fc[gamma]RIII complex," Nature 406(6793):267-273.
Strop et al. (2012) "Generating Bispecific Human IgG1 and IgG2 Antibodies from Any Antibody Pair," J Mol Biol 420:204-19.
Trivedi et al. (2017) "Clinical pharmacology and translational aspects of bispecific antibodies," Clin. Transl. Sci., 10:147-162.
Van de Winkel et al. (1993) "Human IgG Fc receptor heterogeneity: molecular aspects and clinical implications," Immunology Today 14(5):215-221.
Vidarsson et al. (2014) "IgG subclasses and allotypes: from structure to effector functions," Front. Immunol. 5:520, 17 pages.
Von Kreudenstein et al. (2013) "Improving Biophysical Properties of a Bispecific Antibody Scaffold to Aid Developability: Quality by Molecular Design," mAbs 5(5):646-54.
Von Kreudenstein et al. (2014), "Protein Engineering and the Use of Molecular Modeling and Simulation: The Case of Heterodimeric Fc Engineering," Methods 65(1):77-94.
Ward et al. (1989) "Binding activities of a epertoire of single immunoglobulin variable domains secreted from *Escherichia coli,*" Nature 341:544-546.

(56) References Cited

OTHER PUBLICATIONS

Wikipedia: "Trifunctional antibody Jan. 2, 2018",, Jan. 2, 2018 (Jan. 2, 2018), pp. 1-4, XP093016568, Retrieved from the Internet: URL:https://en.wikipedia.org/w/index.php?title=Trifunctional antibody8 oldid=818265015.
Wranik et al. (2012) "LUZ-Y, a novel platform for the mammalian cell production of full-length IgG-bispecific antibodies," J Biol Chem 287(52):43331-9.
Xie et al. (2005) "A new format of bispecific antibody: highly efficient heterodimerization, expression and tumor cell lysis," J Immunol Methods 296(1):95-101.
Zhou et al. (1995) "Characterization of human homologue of 4-1BB and its ligand," Immunology Letters 45:67-73.
U.S. Appl. No. 16/483,330, filed Aug. 2, 2019.
U.S. Appl. No. 16/484,936, filed Aug. 9, 2019.
U.S. Appl. No. 16/483,788, filed Aug. 6, 2019.
U.S. Appl. No. 16/486,921, filed Aug. 19, 2019.
U.S. Appl. No. 18/304,652, filed Apr. 21, 2023.
U.S. Appl. No. 17/095,238, filed Nov. 11, 2020.
U.S. Appl. No. 18/107,292, filed Feb. 8, 2023.
U.S. Appl. No. 16/615,231, filed Nov. 20, 2019.
U.S. Appl. No. 16/615,261, filed Nov. 20, 2019.
U.S. Appl. No. 16/635,079, filed Jan. 29, 2020.
U.S. Appl. No. 17/188,978, filed Mar 1, 2021.
U.S. Appl. No. 16/639,150, filed Feb. 14, 2020.
U.S. Appl. No. 17/190,155, filed Mar. 2, 2021.
U.S. Appl. No. 18/108,961, filed Feb. 13, 2023.
U.S. Appl. No. 16/645,613, filed Mar. 9, 2020.
U.S. Appl. No. 16/967,216, filed Aug. 4, 2020.
U.S. Appl. No. 17/058,335, filed Nov. 24, 2020.
U.S. Appl. No. 16/971,098, filed Aug. 19, 2020.
U.S. Appl. No. 16/967,218, filed Aug. 4, 2020.
U.S. Appl. No. 18/149,965, filed Jan. 4, 2023.
U.S. Appl. No. 18/150,040, filed Jan. 4, 2023.
U.S. Appl. No. 17/045,015, filed Oct. 2, 2020.
U.S. Appl. No. 17/045,016, filed Oct. 2, 2020.
U.S. Appl. No. 17/053,558, filed Nov. 6, 2020.
U.S. Appl. No. 17/055,792, filed Nov. 16, 2020.
U.S. Appl. No. 17/265,876, filed Feb. 4, 2021.
U.S. Appl. No. 17/266,349, filed Feb. 5, 2021.
U.S. Appl. No. 17/543,628, filed Dec. 6, 2021.
U.S. Appl. No. 17/265,879, filed Feb. 4, 2021.
U.S. Appl. No. 17/266,966, filed Feb. 8, 2021.
U.S. Appl. No. 16/971,104, filed Aug. 19, 2010.
U.S. Appl. No. 17/736,031, filed May 3, 2022.
U.S. Appl. No. 17/682,367, filed Feb. 28, 2022.
U.S. Appl. No. 17/308,691, filed May 5, 2021.
U.S. Appl. No. 17/686,238, filed Mar. 3, 2022.
U.S. Appl. No. 17/769,160, filed Apr. 14, 2022.
U.S. Appl. No. 18/003,308, filed Dec. 23, 2022.
U.S. Appl. No. 18/062,453, filed Dec. 6, 2022.
U.S. Appl. No. 18/166,769, filed Feb. 9, 2023.
U.S. Appl. No. 18/177,847, filed Mar. 3, 2023.
PCT/US2022/077083, Sep. 27, 2022.

\* cited by examiner

PROTEINS BINDING HER2, NKG2D AND CD16

CROSS-REFERENCE TO RELATED APPLICATIONS

This application is a U.S. national stage application, filed under 35 U.S.C. § 371, of International Application No. PCT/US2018/018771, filed on Feb. 20, 2018, which claims the benefit of and priority to U.S. Provisional Patent Application No. 62/461,146, filed on Feb. 20, 2017, the entire contents of each of which are incorporated by reference herein for all purposes.

SEQUENCE LISTING

The instant application contains a Sequence Listing which has been submitted electronically in ASCII format and is hereby incorporated by reference in its entirety. Said ASCII copy, created on Feb. 16, 2018, is named DFY-008PC_SL.txt and is 92,807 bytes in size.

FIELD OF THE INVENTION

The invention relates to multi-specific binding proteins that bind to human epidermal growth factor receptor 2 (HER2 or ErbB2), the NKG2D receptor, and CD16.

BACKGROUND

Cancer continues to be a significant health problem despite the substantial research efforts and scientific advances reported in the literature for treating this disease. Some of the most frequently diagnosed cancers include prostate cancer, breast cancer, and lung cancer. Prostate cancer is the most common form of cancer in men. Breast cancer remains a leading cause of death in women. Current treatment options for these cancers are not effective for all patients and/or can have substantial adverse side effects. Other types of cancer also remain challenging to treat using existing therapeutic options.

Cancer immunotherapies are desirable because they are highly specific and can facilitate destruction of cancer cells using the patient's own immune system. Fusion proteins such as bi-specific T-cell engagers are cancer immunotherapies described in the literature that bind to tumor cells and T-cells to facilitate destruction of tumor cells. Antibodies that bind to certain tumor-associated antigens and to certain immune cells have been described in the literature. See, e.g., WO 2016/134371 and WO 2015/095412.

Natural killer (NK) cells are a component of the innate immune system and make up approximately 15% of circulating lymphocytes. NK cells infiltrate virtually all tissues and were originally characterized by their ability to kill tumor cells effectively without the need for prior sensitization. Activated NK cells kill target cells by means similar to cytotoxic T cells—i.e., via cytolytic granules that contain perforin and granzymes as well as via death receptor pathways. Activated NK cells also secrete inflammatory cytokines such as IFN-γ and chemokines that promote the recruitment of other leukocytes to the target tissue.

NK cells respond to signals through a variety of activating and inhibitory receptors on their surface. For example, when NK cells encounter healthy self-cells, their activity is inhibited through activation of the killer-cell immunoglobulin-like receptors (KIRs). Alternatively, when NK cells encounter foreign cells or cancer cells, they are activated via their activating receptors (e.g., NKG2D, NCRs, DNAM1). NK cells are also activated by the constant region of some immunoglobulins through CD16 receptors on their surface. The overall sensitivity of NK cells to activation depends on the sum of stimulatory and inhibitory signals.

HER2 (ErbB2) is a transmembrane glycoprotein, which belongs to the epidermal growth factor receptor family. It is a receptor tyrosine kinase and regulates cell survival, proliferation, and growth. HER2 plays an important role in human malignancies. The erbB2 gene is amplified or over-expressed in approximately 30% of human breast cancers. Patients with HER2-overexpressing breast cancer have substantially lower overall survival rates and shorter disease-free intervals than patients whose cancer does not overexpress HER2. Moreover, overexpression of HER2 leads to increased breast cancer metastasis. Over-expression of HER2 is also known to occur in many other cancer types, including breast, ovarian, esophageal, bladder and gastric cancer, salivary duct carcinoma, adenocarcinoma of the lung and aggressive forms of uterine cancer, such as uterine serous endometrial carcinoma.

SUMMARY

The invention provides multi-specific binding proteins that bind to HER2 on a cancer cell and to the NKG2D receptor and CD16 receptor on natural killer cells. Such proteins can engage more than one kind of NK activating receptor, and may block the binding of natural ligands to NKG2D. In certain embodiments, the proteins can agonize NK cells in humans, and in other species such as rodents and cynomolgus monkeys. Various aspects and embodiments of the invention are described in further detail below.

Accordingly, one aspect of the invention provides a protein that incorporates a first antigen-binding site that binds NKG2D; a second antigen-binding site that binds to HER2; and an antibody Fc domain, a portion thereof sufficient to bind CD16, or a third antigen-binding site that binds CD16. The antigen-binding sites may each incorporate an antibody heavy chain variable domain and an antibody light chain variable domain (e.g., arranged as in an antibody, or fused together to from an scFv, or one or more of the antigen-binding sites may be a single domain antibody, such as a $V_HH$ antibody like a camelid antibody or a $V_{NAR}$ antibody like those found in cartilaginous fish.

The first antigen-binding site, which binds to NKG2D, in one embodiment, can incorporate a heavy chain variable domain related to SEQ ID NO:1, such as by having an amino acid sequence at least 90% (e.g., 90%, 91%, 92%, 93%, 94%, 95%, 96%, 97%, 98%, 99%, or 100%) identical to SEQ ID NO: 1, and/or incorporating amino acid sequences identical to the CDR1 (SEQ ID NO:62), CDR2 (SEQ ID NO:63), and CDR3 (SEQ ID NO:64) sequences of SEQ ID NO: 1. Alternatively, the first antigen-binding site can incorporate a heavy chain variable domain related to SEQ ID NO:41 and a light chain variable domain related to SEQ ID NO:42. For example, the heavy chain variable domain of the first antigen binding site can be at least 90% (e.g., 90%, 91%, 92%, 93%, 94%, 95%, 96%, 97%, 98%, 99%, or 100%) identical to SEQ ID NO:41, and/or incorporate amino acid sequences identical to the CDR1 (SEQ ID NO:65), CDR2 (SEQ ID NO:66), and CDR3 (SEQ ID NO:67) sequences of SEQ ID NO:41. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:42, and/or incorporate amino acid sequences identical to the CDR1 (SEQ ID NO:68), CDR2 (SEQ ID NO:69), and CDR3 (SEQ ID NO:70) sequences of SEQ ID NO:42. In other embodiments, the first antigen-binding site can incorporate a heavy chain variable domain related to SEQ ID NO:43 and a light chain variable domain related to SEQ ID NO:44. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:43, and/or incorporate amino acid sequences identical to the CDR1 (SEQ ID NO:71), CDR2 (SEQ ID NO:72), and CDR3 (SEQ ID NO:73) sequences of SEQ ID NO:43. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:44, and/or incorporate amino acid sequences identical to the CDR1 (SEQ ID NO:74), CDR2 (SEQ ID NO:75), and CDR3 (SEQ ID NO:76) sequences of SEQ ID NO:44.

Alternatively, the first antigen-binding site can incorporate a heavy chain variable domain related to SEQ ID NO:45 and a light chain variable domain related to SEQ ID NO:46, such as by having amino acid sequences at least 90% (e.g., 90%, 91%, 92%, 93%, 94%, 95%, 96%, 97%, 98%, 99%, or 100%) identical to SEQ ID NO:45 and at least 90% (e.g., 90%, 91%, 92%, 93%, 94%, 95%, 96%, 97%, 98%, 99%, or 100%) identical to SEQ ID NO:46 respectively. In another embodiment, the first antigen-binding site can incorporate a heavy chain variable domain related to SEQ ID NO:47 and a light chain variable domain related to SEQ ID NO:48, such as by having amino acid sequences at least 90% (e.g., 90%, 91%, 92%, 93%, 94%, 95%, 96%, 97%, 98%, 99%, or 100%) identical to SEQ ID NO:47 and at least 90% (e.g., 90%, 91%, 92%, 93%, 94%, 95%, 96%, 97%, 98%, 99%, or 100%) identical to SEQ ID NO:48 respectively.

The second antigen-binding site can optionally incorporate a heavy chain variable domain related to SEQ ID NO:49 and a light chain variable domain related to SEQ ID NO:53. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:49, and/or incorporate amino acid sequences identical to the CDR1 (SEQ ID NO:50), CDR2 (SEQ ID NO:51), and CDR3 (SEQ ID NO:52) sequences of SEQ ID NO:49. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:53 and/or incorporate amino acid sequences identical to the CDR1 (SEQ ID NO:54), CDR2 (SEQ ID NO:55), and CDR3 (SEQ ID NO:56) sequences of SEQ ID NO:53.

Alternatively, the second antigen-binding site can incorporate a heavy chain variable domain related to SEQ ID NO:57 and a light chain variable domain related to SEQ ID NO:58. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:57, and/or incorporate amino acid sequences identical to the CDR1 (SEQ ID NO:77), CDR2 (SEQ ID NO:78), and CDR3 (SEQ ID NO:79) sequences of SEQ ID NO:57. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:58, and/or incorporate amino acid sequences identical to the CDR1 (SEQ ID NO:80), CDR2 (SEQ ID NO:81), and CDR3 (SEQ ID NO:82) sequences of SEQ ID NO:58.

In another embodiment, the second antigen-binding site can incorporate a heavy chain variable domain related to SEQ ID NO:59 and a light chain variable domain related to SEQ ID NO:60. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:59, and/or incorporate amino acid sequences identical to the CDR1 (SEQ ID NO:83), CDR2 (SEQ ID NO:84), and CDR3 (SEQ ID NO:85) sequences of SEQ ID NO:59. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:60, and/or incorporate amino acid sequences identical to the CDR1 (SEQ ID NO:86), CDR2 (SEQ ID NO:87), and CDR3 (SEQ ID NO:88) sequences of SEQ ID NO:60.

In some embodiments, the second antigen-binding site incorporates a light chain variable domain having an amino acid sequence identical to the amino acid sequence of the light chain variable domain present in the first antigen-binding site.

In some embodiments, the protein incorporates a portion of an antibody Fc domain sufficient to bind CD16, wherein the antibody Fc domain comprises hinge and CH2 domains, and/or amino acid sequences at least 90% identical to amino acid sequence 234-332 of a human IgG antibody.

Formulations containing one of these proteins; cells containing one or more nucleic acids expressing these proteins, and methods of enhancing tumor cell death using these proteins are also provided.

Another aspect of the invention involves a method of treating cancer in a patient. The method comprises administering to a patient in need thereof a therapeutically effective amount of the multi-specific binding protein described herein. Exemplary cancers for treatment using the multi-specific binding proteins include, for example, breast, ovarian, esophageal, bladder and gastric cancer, salivary duct carcinoma, adenocarcinoma of the lung and aggressive forms of uterine cancer, such as uterine serous endometrial carcinoma.

BRIEF DESCRIPTION OF THE DRAWINGS

FIG. 26 represents the same two NKG2D-binding domains now paired with a HER2 second targeting arm.

FIG. 28A shows that human NK cells are activated by TriNKETs when cultured with SkBr-3 cells. FIG. 28B shows that human NK cells are activated by TriNKETs when cultured with Colo201 cells. FIG. 28C shows that human NK cell are activated by TriNKETs when cultured with HCC1954 cells.

FIG. 29A shows activated human NK cell killing of HER2 high-SkBr-3 tumor cells. FIG. 29B shows human NK cell killing of HER2 low-786-O tumor cells. TriNKETs provide a greater advantage compared to trastuzumab against cancer cells with low HER2 expression.

FIG. 30A demonstrates levels of CD107a; FIG. 30B demonstrates levels of IFNγ; FIG. 30C demonstrates levels of CD107a and IFNγ. Graphs indicate the mean (n=2)±SD. Data are representative of five independent experiments using five different healthy donors.

FIG. 32A shows percent specific lysis of SkBr-3 tumor cells by rested human NK cells. FIG. 32B shows percent specific lysis of SkBr-3 tumor cells by IL-2-activated human NK cells. FIG. 32C shows percent specific lysis of NCI-H661 lung cancer cells by IL-2-activated human NK cells.

FIG. 49A is an exemplary representation of one form of a κλ-Body; FIG. 49B is an exemplary representation of another κλ-Body.

DETAILED DESCRIPTION

Figure 1:
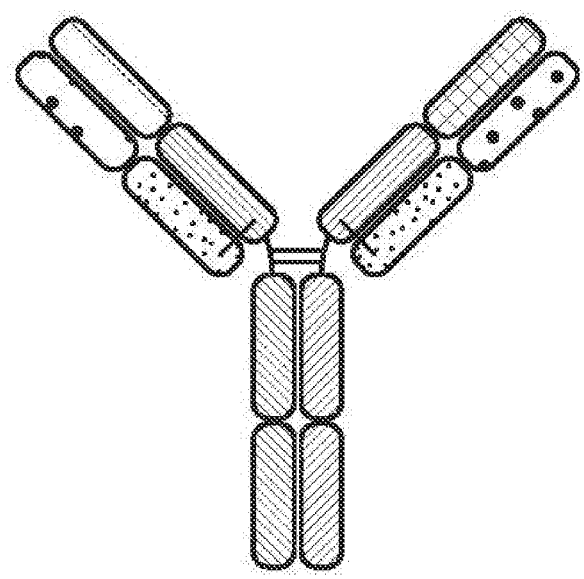
FIG. 1 is a representation of a multi-specific binding protein that contains an NKG2D-binding domain (right arm), a tumor associated antigen-binding domain (left arm) and an Fc domain or a portion thereof that binds to CD16.

The invention provides multi-specific binding proteins that bind a HER2 on a cancer cell and the NKG2D receptor and CD16 receptor on natural killer cells to activate the natural killer cell, pharmaceutical compositions comprising such multi-specific binding proteins, and therapeutic methods using such multi-specific proteins and pharmaceutical compositions, including for the treatment of cancer. Various aspects of the invention are set forth below in sections; however, aspects of the invention described in one particular section are not to be limited to any particular section.

To facilitate an understanding of the present invention, a number of terms and phrases are defined below.

The terms "a" and "an" as used herein mean "one or more" and include the plural unless the context is inappropriate. As used herein, the term "antigen-binding site" refers to the part of the immunoglobulin molecule that participates in antigen binding. In human antibodies, the antigen-binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs." Thus the term "FR" refers to amino acid sequences which are naturally found between and adjacent to hypervariable regions in immunoglobulins. In a human antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." In certain animals, such as camels and cartilaginous fish, the antigen-binding site is formed by a single antibody chain providing a "single domain antibody." Antigen-binding sites can exist in an intact antibody, in an antigen-binding fragment of an antibody that retains the antigen-binding surface, or in a recombinant polypeptide such as an scFv, using a peptide linker to connect the heavy chain variable domain to the light chain variable domain in a single polypeptide.

The term "tumor associated antigen" as used herein means any antigen including but not limited to a protein, glycoprotein, ganglioside, carbohydrate, lipid that is associated with cancer. Such antigen can be expressed on malignant cells or in the tumor microenvironment such as on tumor-associated blood vessels, extracellular matrix, mesenchymal stroma, or immune infiltrates.

As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably include humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Exemplary acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Exemplary bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Exemplary salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

I. Proteins

The invention provides multi-specific binding proteins that bind HER2 on a cancer cell and the NKG2D receptor and CD16 receptor on natural killer cells to activate the natural killer cell. The multi-specific binding proteins are useful in the pharmaceutical compositions and therapeutic methods described herein. Binding of the multi-specific binding protein to the NKG2D receptor and CD16 receptor on natural killer cell enhances the activity of the natural killer cell toward destruction of a cancer cell. Binding of the multi-specific binding protein to HER2 on a cancer cell brings the cancer cell into proximity with the natural killer cell, which facilitates direct and indirect destruction of the cancer cell by the natural killer cell. Further description of exemplary multi-specific binding proteins is provided below.

The first component of the multi-specific binding proteins binds to NKG2D receptor-expressing cells, which can include but are not limited to NK cells, γδ T cells and $CD8^+\alpha\beta$ T cells. Upon NKG2D binding, the multi-specific binding proteins may block natural ligands, such as ULBP6 and MICA, from binding to NKG2D and activating NKG2D receptors.

The second component of the multi-specific binding proteins binds to HER2-expressing cells, which can include but are limited to breast, ovarian, esophageal, bladder and gastric cancer, salivary duct carcinoma, adenocarcinoma of the lung and aggressive forms of uterine cancer, such as uterine serous endometrial carcinoma.

The third component for the multi-specific binding proteins binds to cells expressing CD16, an Fc receptor on the surface of leukocytes including natural killer cells, macrophages, neutrophils, eosinophils, mast cells, and follicular dendritic cells.

The multi-specific binding proteins described herein can take various formats. For example, one format is a heterodimeric, multi-specific antibody including a first immunoglobulin heavy chain, a first immunoglobulin light chain, a second immunoglobulin heavy chain and a second immunoglobulin light chain (FIG. 1). The first immunoglobulin heavy chain includes a first Fc (hinge-CH2-CH3) domain, a first heavy chain variable domain and optionally a first CH1 heavy chain domain. The first immunoglobulin light chain includes a first light chain variable domain and a first light chain constant domain. The first immunoglobulin light chain, together with the first immunoglobulin heavy chain, forms an antigen-binding site that binds NKG2D. The second immunoglobulin heavy chain comprises a second Fc (hinge-CH2-CH3) domain, a second heavy chain variable domain and optionally a second CH1 heavy chain domain. The second immunoglobulin light chain includes a second light chain variable domain and a second light chain constant domain. The second immunoglobulin light chain, together with the second immunoglobulin heavy chain, forms an antigen-binding site that binds HER2. The first Fc domain and second Fc domain together are able to bind to CD16 (FIG. 1). In some embodiments, the first immunoglobulin light chain can be identical to the second immunoglobulin light chain.

Figure 2:
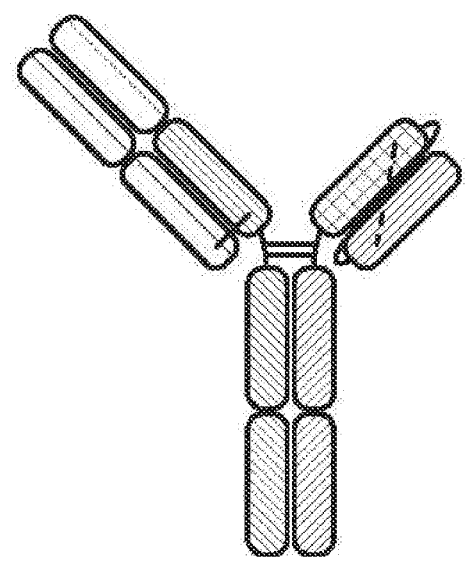
FIG. 2 is a representation of a multi-specific binding protein that contains an NKG2D-binding domain in a scFv format (right arm), a tumor associated antigen-binding domain (left arm) and an Fc domain or a portion thereof that binds to CD16.

Another exemplary format involves a heterodimeric, multi-specific antibody including a first immunoglobulin heavy chain, a second immunoglobulin heavy chain and an immunoglobulin light chain (FIG. 2). The first immunoglobulin heavy chain includes a first Fc (hinge-CH2-CH3) domain fused via either a linker or an antibody hinge to a single-chain variable fragment (scFv) composed of a heavy variable domain and light chain variable domain which pair and bind NKG2D or HER2. The second immunoglobulin heavy chain includes a second Fc (hinge-CH2-CH3) domain, a second heavy chain variable domain and optionally a CH1 heavy chain domain. The immunoglobulin light chain includes a light chain variable domain and a constant light chain domain. The second immunoglobulin heavy chain pairs with the immunoglobulin light chain and binds to NKG2D or HER2. The first Fc domain and the second Fc domain together are able to bind to CD16 (FIG. 2).

One or more additional binding motifs may be fused to the C-terminus of the constant region CH3 domain, optionally via a linker sequence. In certain embodiments, the antigen-binding site could be a single-chain or disulfide-stabilized variable region (scFv) or could form a tetravalent or trivalent molecule.

In some embodiments, the multi-specific binding protein is in the Triomab form, which is a trifunctional, bispecific antibody that maintains an IgG-like shape. This chimera consists of two half antibodies, each with one light and one heavy chain, that originate from two parental antibodies.

In some embodiments, the multi-specific binding protein is the KiH Common Light Chain (LC) form, which involves the knobs-into-holes (KIHs) technology. The KIH involves engineering $C_H3$ domains to create either a "knob" or a "hole" in each heavy chain to promote heterodimerization. The concept behind the "Knobs-into-Holes (KiH)" Fc technology was to introduce a "knob" in one CH3 domain (CH3A) by substitution of a small residue with a bulky one (e.g., $T366W_{CH3A}$ in EU numbering). To accommodate the "knob," a complementary "hole" surface was created on the other CH3 domain (CH3B) by replacing the closest neighboring residues to the knob with smaller ones (e.g., T366S/L368A/$Y407V_{CH3B}$). The "hole" mutation was optimized by structured-guided phage library screening (Atwell S, Ridgway J B, Wells J A, Carter P., Stable heterodimers from remodeling the domain interface of a homodimer using a phage display library, *J. Mol. Biol.* (1997) 270(1):26-35). X-ray crystal structures of KiH Fc variants (Elliott J M, Ultsch M, Lee J, Tong R, Takeda K, Spiess C, et al., Antiparallel conformation of knob and hole aglycosylated half-antibody homodimers is mediated by a CH2-CH3 hydrophobic interaction. *J. Mol. Biol.* (2014) 426(9):1947-57; Mimoto F, Kadono S, Katada H, Igawa T, Kamikawa T, Hattori K. Crystal structure of a novel asymmetrically engineered Fc variant with improved affinity for FcgammaRs. *Mol. Immunol.* (2014) 58(1):132-8) demonstrated that heterodimerization is thermodynamically favored by hydrophobic interactions driven by steric complementarity at the inter-CH3 domain core interface, whereas the knob-knob and the hole-hole interfaces do not favor homodimerization owing to steric hindrance and disruption of the favorable interactions, respectively.

In some embodiments, the multi-specific binding protein is in the dual-variable domain immunoglobulin (DVD-Ig™) form, which combines the target binding domains of two monoclonal antibodies via flexible naturally occurring linkers, and yields a tetravalent IgG-like molecule.

In some embodiments, the multi-specific binding protein is in the Orthogonal Fab interface (Ortho-Fab) form. In the ortho-Fab IgG approach (Lewis S M, Wu X, Pustilnik A, Sereno A, Huang F, Rick H L, et al., Generation of bispecific IgG antibodies by structure-based design of an orthogonal Fab interface. *Nat. Biotechnol.* (2014) 32(2):191-8), structure-based regional design introduces complementary mutations at the LC and $HC_{VH-CH1}$ interface in only one Fab, without any changes being made to the other Fab.

Figure 49A:
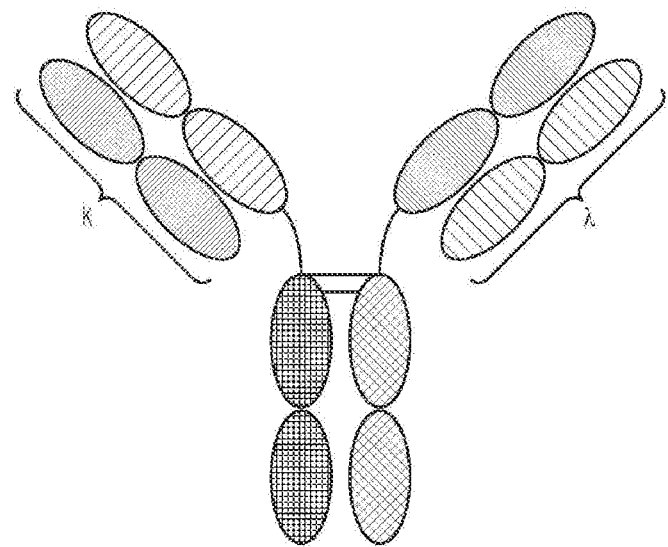
FIGS. 49A-49B are representations of TriNKETs in the κλ-Body forms, which are an heterodimeric constructs with two different Fabs fused to Fc stabilized by heterodimerization mutations: Fab1 targeting antigen 1 contains kappa LC, while second Fab targeting antigen 2 contains lambda LC.
Figure 49B:
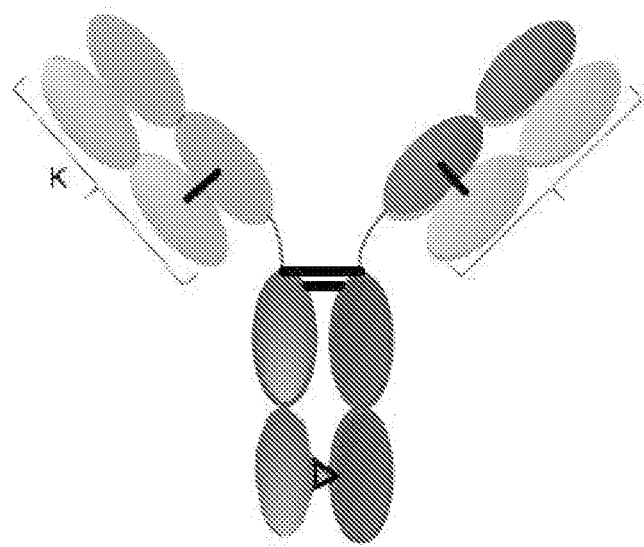
Figure 50:
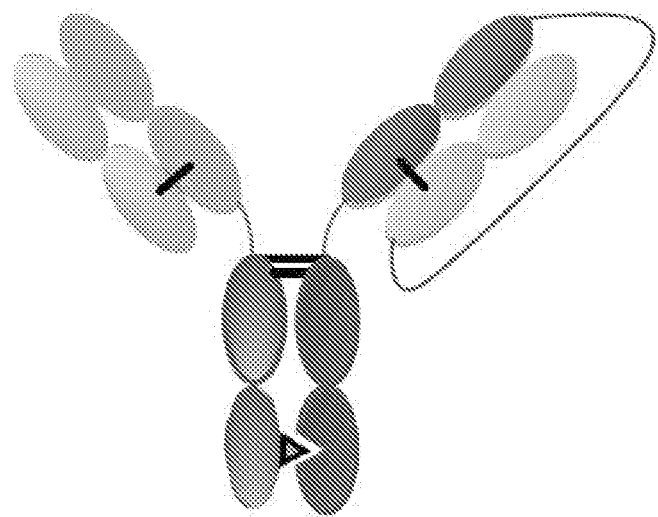
FIG. 50 is an Oasc-Fab heterodimeric construct that includes Fab binding to target 1 and scFab binding to target 2 fused to Fc. Heterodimerization is ensured by mutations in the Fc.
Figure 51:
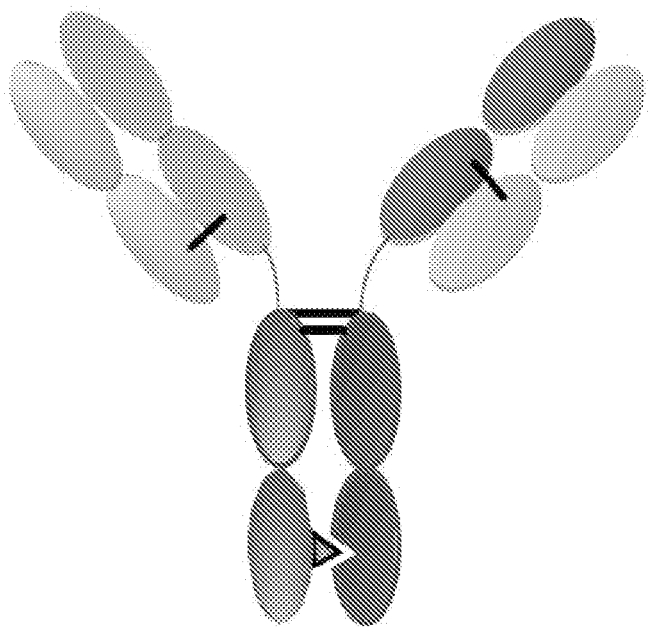
FIG. 51 is a DuetMab, which is an heterodimeric construct containing two different Fabs binding to antigens 1 and 2, and Fc stabilized by heterodimerization mutations. Fab 1 and 2 contain differential S-S bridges that ensure correct light chain (LC) and heavy chain (HC) pairing.
Figure 52:
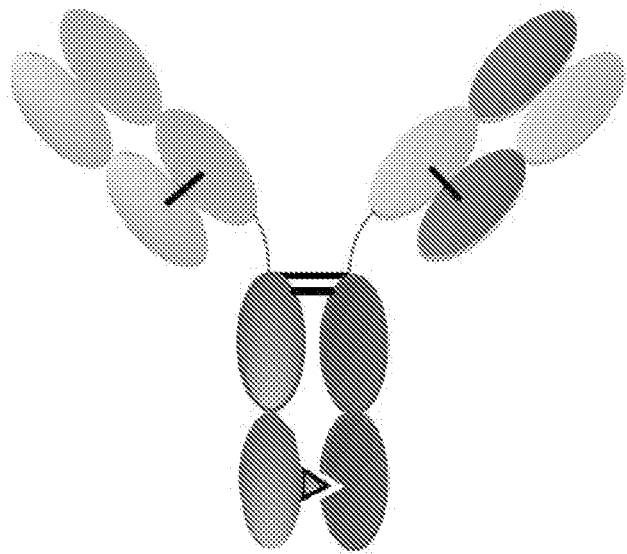
FIG. 52 is a CrossmAb, which is an heterodimeric construct with two different Fabs binding to targets 1 and 2 fused to Fc stabilized by heterodimerization. CL and CH1 domains and VH and VL domains are switched, e.g., CH1 is fused in-line with VL, while CL is fused in-line with VH.
Figure 53:
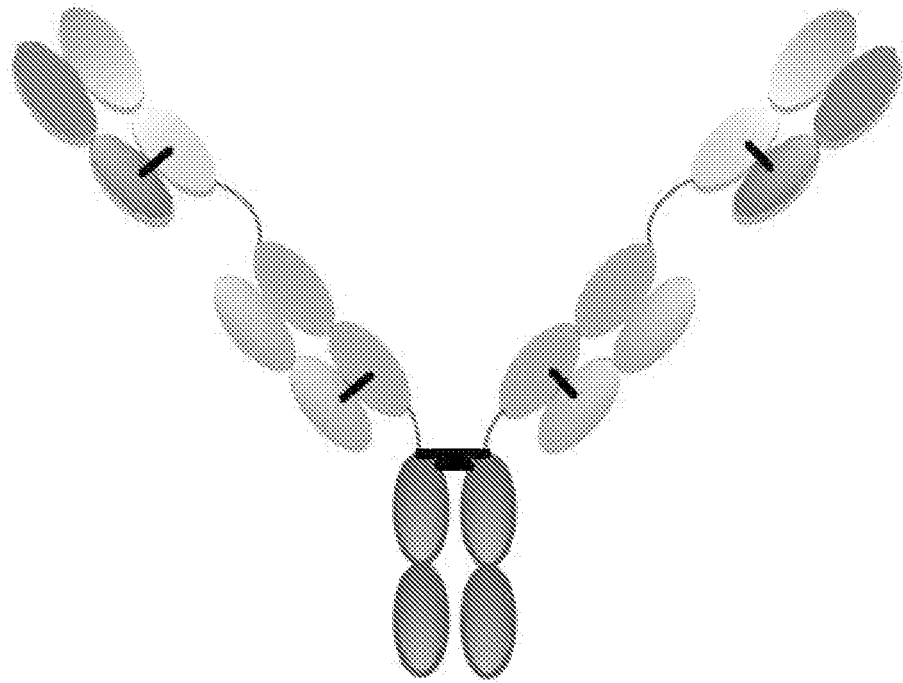
FIG. 53 is a Fit-Ig, which is an homodimeric constructs where Fab binding to antigen 2 is fused to the N terminus of HC of Fab that binds to antigen 1. The construct contains wild-type Fc.

In some embodiments, the multi-specific binding protein is in the 2-in-1 Ig format. In some embodiments, the multi-specific binding protein is in the ES form, which is a heterodimeric construct containing two different Fabs binding to targets 1 and target 2 fused to the Fc. Heterodimerization is ensured by electrostatic steering mutations in the Fc. In some embodiments, the multi-specific binding protein is in the κλ-Body form, which is an heterodimeric constructs with two different Fabs fused to Fc stabilized by heterodimerization mutations: Fab1 targeting antigen 1 contains kappa LC, while second Fab targeting antigen 2 contains lambda LC. FIG. 49A is an exemplary representation of one form of a κλ-Body; FIG. 49B is an exemplary representation of another κλ-Body.

In some embodiments, the multi-specific binding protein is in Fab Arm Exchange form (antibodies that exchange Fab arms by swapping a heavy chain and attached light chain (half-molecule) with a heavy-light chain pair from another molecule, which results in bispecific antibodies). In some embodiments, the multi-specific binding protein is in the SEED Body form. The strand-exchange engineered domain (SEED) platform was designed to generate asymmetric and bispecific antibody-like molecules, a capability that expands therapeutic applications of natural antibodies. This protein engineered platform is based on exchanging structurally related sequences of immunoglobulin within the conserved CH3 domains. The SEED design allows efficient generation of AG/GA heterodimers, while disfavoring homodimerization of AG and GA SEED CH3 domains. (Muda M. et al., *Protein Eng. Des. Sel.* (2011, 24(5):447-54)). In some embodiments, the multi-specific binding protein is in the LuZ-Y form, in which a leucine zipper is used to induce heterodimerization of two different HCs. (Wranik, B J. et al., *J. Biol. Chem.* (2012), 287:43331-9).

In some embodiments, the multi-specific binding protein is in the Cov-X-Body form. In bispecific CovX-Bodies, two different peptides are joined together using a branched azetidinone linker and fused to the scaffold antibody under mild conditions in a site-specific manner. Whereas the pharmacophores are responsible for functional activities, the antibody scaffold imparts long half-life and Ig-like distribution. The pharmacophores can be chemically optimized or replaced with other pharmacophores to generate optimized or unique bispecific antibodies. (Doppalapudi V R et al., *PNAS* (2010), 107(52); 22611-22616).

In some embodiments, the multi-specific binding protein is in an Oasc-Fab heterodimeric form that includes Fab binding to target 1, and scFab binding to target 2 fused to Fc. Heterodimerization is ensured by mutations in the Fc.

In some embodiments, the multi-specific binding protein is in a DuetMab form, which is an heterodimeric construct containing two different Fabs binding to antigens 1 and 2, and Fc stabilized by heterodimerization mutations. Fab 1 and 2 contain differential S-S bridges that ensure correct LC and HC pairing.

In some embodiments, the multi-specific binding protein is in a CrossmAb form, which is an heterodimeric construct with two different Fabs binding to targets 1 and 2, fused to Fc stabilized by heterodimerization. CL and CH1 domains and VH and VL domains are switched, e.g., CH1 is fused in-line with VL, while CL is fused in-line with VH.

In some embodiments, the multi-specific binding protein is in a Fit-Ig form, which is an homodimeric constructs where Fab binding to antigen 2 is fused to the N terminus of HC of Fab that binds to antigen 1. The construct contains wild-type Fc.

Additional formats of the multi-specific binding proteins can be devised by combining various formats of NKG2D- and HER2-binding fragments described herein.

Table 1 lists peptide sequences of heavy chain variable domains and light chain variable domains that, in combination, can bind to NKG2D.

TABLE 1

| Clones | Heavy chain variable region amino acid sequence | Light chain variable region amino acid sequence |
| --- | --- | --- |
| ADI-27705 | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 1) CDR1(SEQ ID NO: 62)-GSFSGYYWS CDR2(SEQ ID NO: 63)- EIDHSGSTNYNPSLKS CDR3(SEQ ID NO: 64)- ARARGPWSFDP | DIQMTQSPSTLSASVGDRVTITCR ASQSISSWLAWYQQKPGKAPKLL IYKASSLESGVPSRFSGSGSGTEFT LTISSLQPDDFATYYCQQYNSYPI TFGGGTKVEIK (SEQ ID NO: 2) |
| ADI-27724 | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 3) | EIVLTQSPGTLSLSPGERATLSCRA SQSVSSSYLAWYQQKPGQAPRLL IYGASSRATGIPDRFSGSGSGTDFT LTISRLEPEDFAVYYCQQYGSSPIT FGGGTKVEIK (SEQ ID NO: 4) |
| ADI-27740 (A40) | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 5) | DIQMTQSPSTLSASVGDRVTITCR ASQSIGSWLAWYQQKPGKAPKLL IYKASSLESGVPSRFSGSGSGTEFT LTISSLQPDDFATYYCQQYHSFYT FGGGTKVEIK (SEQ ID NO: 6) |
| ADI-27741 | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 7) | DIQMTQSPSTLSASVGDRVTITCR ASQSIGSWLAWYQQKPGKAPKLL IYKASSLESGVPSRFSGSGSGTEFT LTISSLQPDDFATYYCQQSNSYYT FGGGTKVEIK (SEQ ID NO: 8) |
| ADI-27743 | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 9) | DIQMTQSPSTLSASVGDRVTITCR ASQSISSWLAWYQQKPGKAPKLL IYKASSLESGVPSRFSGSGSGTEFT LTISSLQPDDFATYYCQQYNSYPT FGGGTKVEIK (SEQ ID NO: 10) |
| ADI-28153 | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW GFDPWGQGTLVTVSS (SEQ ID NO: 11) | ELQMTQSPSSLSASVGDRVTITCR TSQSISSYLNWYQQKPGQPPKLLI YWASTRESGVPDRFSGSGSGTDF TLTISSLQPEDSATYYCQQSYDIP YTFGQGTKLEIK (SEQ ID NO: 12) |
| ADI-28226 (C26) | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 13) | DIQMTQSPSTLSASVGDRVTITCR ASQSISSWLAWYQQKPGKAPKLL IYKASSLESGVPSRFSGSGSGTEFT LTISSLQPDDFATYYCQQYGSFPIT FGGGTKVEIK (SEQ ID NO: 14) |
| ADI-28154 | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 15) | DIQMTQSPSTLSASVGDRVTITCR ASQSISSWLAWYQQKPGKAPKLL IYKASSLESGVPSRFSGSGSGTDFT LTISSLQPDDFATYYCQQSKEVP WTFGQGTKVEIK (SEQ ID NO: 16) |
| ADI-29399 | QVQLQQWGAGLLKPSETLSLTCAVY GGSFSGYYWSWIRQPPGKGLEWIGEI | DIQMTQSPSTLSASVGDRVTITCR ASQSISSWLAWYQQKPGKAPKLL |

TABLE 1-continued

| Clones | Heavy chain variable region amino acid sequence | Light chain variable region amino acid sequence |
|---|---|---|
| | DHSGSTNYNPSLKSRVTISVDTSKNQ FSLKLSSVTAADTAVYYCARARGPW SFDPWGQGTLVTVSS (SEQ ID NO: 17) | IYKASSLESGVPSRFSGSGSGTEFT LTISSLQPDDFATYYCQQYNSFPT FGGGTKVEIK (SEQ ID NO: 18) |
| ADI-29401 | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 19) | DIQMTQSPSTLSASVGDRVTITCR ASQSIGSWLAWYQQKPGKAPKLL IYKASSLESGVPSRFSGSGSGTEFT LTISSLQPDDFATYYCQQYDIYPT FGGGTKVEIK (SEQ ID NO: 20) |
| ADI-29403 | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 21) | DIQMTQSPSTLSASVGDRVTITCR ASQSISSWLAWYQQKPGKAPKLL IYKASSLESGVPSRFSGSGSGTEFT LTISSLQPDDFATYYCQQYDSYPT FGGGTKVEIK (SEQ ID NO: 22) |
| ADI-29405 | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 23) | DIQMTQSPSTLSASVGDRVTITCR ASQSISSWLAWYQQKPGKAPKLL IYKASSLESGVPSRFSGSGSGTEFT LTISSLQPDDFATYYCQQYGSFPT FGGGTKVEIK (SEQ ID NO: 24) |
| ADI-29407 | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 25) | DIQMTQSPSTLSASVGDRVTITCR ASQSISSWLAWYQQKPGKAPKLL IYKASSLESGVPSRFSGSGSGTEFT LTISSLQPDDFATYYCQQYQSFPT FGGGTKVEIK (SEQ ID NO: 26) |
| ADI-29419 | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 27) | DIQMTQSPSTLSASVGDRVTITCR ASQSISSWLAWYQQKPGKAPKLL IYKASSLESGVPSRFSGSGSGTEFT LTISSLQPDDFATYYCQQYSSFST FGGGTKVEIK (SEQ ID NO: 28) |
| ADI-29421 | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 29) | DIQMTQSPSTLSASVGDRVTITCR ASQSISSWLAWYQQKPGKAPKLL IYKASSLESGVPSRFSGSGSGTEFT LTISSLQPDDFATYYCQQYESYST FGGGTKVEIK (SEQ ID NO: 30) |
| ADI-29424 | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 31) | DIQMTQSPSTLSASVGDRVTITCR ASQSISSWLAWYQQKPGKAPKLL IYKASSLESGVPSRFSGSGSGTEFT LTISSLQPDDFATYYCQQYDSFITF GGGTKVEIK (SEQ ID NO: 32) |
| ADI-29425 | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 33) | DIQMTQSPSTLSASVGDRVTITCR ASQSISSWLAWYQQKPGKAPKLL IYKASSLESGVPSRFSGSGSGTEFT LTISSLQPDDFATYYCQQYQSYPT FGGGTKVEIK (SEQ ID NO: 34) |
| ADI-29426 | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 35) | DIQMTQSPSTLSASVGDRVTITCR ASQSIGSWLAWYQQKPGKAPKLL IYKASSLESGVPSRFSGSGSGTEFT LTISSLQPDDFATYYCQQYHSFPT FGGGTKVEIK (SEQ ID NO: 36) |
| ADI-29429 | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 37) | DIQMTQSPSTLSASVGDRVTITCR ASQSIGSWLAWYQQKPGKAPKLL IYKASSLESGVPSRFSGSGSGTEFT LTISSLQPDDFATYYCQQYELYSY TFGGGTKVEIK (SEQ ID NO: 38) |
| ADI-29447 (F47) | QVQLQQWGAGLLKPSETLSLTCAVY GGSFSGYYWSWIRQPPGKGLEWIGEI | DIQMTQSPSTLSASVGDRVTITCR ASQSISSWLAWYQQKPGKAPKLL |

TABLE 1-continued

| Clones | Heavy chain variable region amino acid sequence | Light chain variable region amino acid sequence |
| --- | --- | --- |
| | DHSGSTNYNPSLKSRVTISVDTSKNQ FSLKLSSVTAADTAVYYCARARGPW SFDPWGQGTLVTVSS (SEQ ID NO: 39) | IYKASSLESGVPSRFSGSGSGTEFT LTISSLQPDDFATYYCQQYDTFIT FGGGTKVEIK (SEQ ID NO: 40) |
| ADI-27727 | QVQLVQSGAEVKKPGSSVKVSCKAS GGTFSSYAISWVRQAPGQGLEWMGG IIPIFGTANYAQKFQGRVTITADESTS TAYMELSSLRSEDTAVYYCARGDSSI RHAYYYYGMDVWGQGTTVTVSS (SEQ ID NO: 41) CDR1(SEQ ID NO: 65)- GTFSSYAIS CDR2(SEQ ID NO: 66)- GIIPIFGTANYAQKFQG CDR3(SEQ ID NO: 67)- ARGDSSIRHAYYYYGMDV | DIVMTQSPDSLAVSLGERATINCK SSQSVLYSSNNKNYLAWYQQKP GQPPKLLIYWASTRESGVPDRFSG SGSGTDFTLTISSLQAEDVAVYYC QQYYSTPITFGGGTKVEIK (SEQ ID NO: 42) CDR1(SEQ ID NO: 68)- KSSQSVLYSSNNKNYLA CDR2(SEQ ID NO: 69)- WASTRES CDR3(SEQ ID NO: 70)- QQYYSTPIT |
| ADI-29443 (F43) | QLQLQESGPGLVKPSETLSLTCTVSG GSISSSSYYWGWIRQPPGKGLEWIGSI YYSGSTYYNPSLKSRVTISVDTSKNQ FSLKLSSVTAADTAVYYCARGSDRF HPYFDYWGQGTLVTVSS (SEQ ID NO: 43) CDR1(SEQ ID NO: 71)- GSISSSSYYWG CDR2(SEQ ID NO: 72)- SIYYSGSTYYNPSLKS CDR3(SEQ ID NO: 73)- ARGSDRFHPYFDY | EIVLTQSPATLSLSPGERATLSCRA SQSVSRYLAWYQQKPGQAPRLLI YDASNRATGIPARFSGSGSGTDFT LTISSLEPEDFAVYYCQQFDTWPP TFGGGTKVEIK (SEQ ID NO: 44) CDR1(SEQ ID NO: 74)- RASQSVSRYLA CDR2(SEQ ID NO: 75)- DASNRAT CDR3(SEQ ID NO: 76)- QQFDTWPPT |
| ADI-29404 (F04) | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 89) | DIQMTQSPSTLSASVGDRVTITCR ASQSISSWLAWYQQKPGKAPKLL IYKASSLESGVPSRFSGSGSGTEFT LTISSLQPDDFATYYCEQYDSYPT FGGGTKVEIK (SEQ ID NO: 90) |
| ADI-28200 | QVQLVQSGAEVKKPGSSVKVSCKAS GGTFSSYAISWVRQAPGQGLEWMGG IIPIFGTANYAQKFQGRVTITADESTS TAYMELSSLRSEDTAVYYCARRGRK ASGSFYYYGMDVWGQGTTVTVSS (SEQ ID NO: 91) | DIVMTQSPDSLAVSLGERATINCE SSQSLLNSGNQKNYLTWYQQKP GQPPKPLIYWASTRESGVPDRFSG SGSGTDFTLTISSLQAEDVAVYYC QNDYSYPYTFGQGTKLEIK (SEQ ID NO: 92) |
| ADI-29379 (E79) | QVQLVQSGAEVKKPGASVKVSCKAS GYTFTSYYMHWVRQAPGQGLEWM GIINPSGGSTSYAQKFQGRVTMTRDT STSTVYMELSSLRSEDTAVYYCARG APNYGDTTHDYYYMDVWGKGTTVT VSS (SEQ ID NO: 94) CDR1(SEQ ID NO: 96)-YTFTSYYMH CDR2(SEQ ID NO: 97)- IINPSGGSTSYAQKFQG CDR3(SEQ ID NO: 98)- ARGAPNYGDTTHDYYYMDV | EIVMTQSPATLSVSPGERATLSCR ASQSVSSNLAWYQQKPGQAPRLL IYGASTRATGIPARFSGSGSGTEFT LTISSLQSEDFAVYYCQQYDDWP FTFGGGTKVEIK (SEQ ID NO: 95) CDR1(SEQ ID NO: 99)- RASQSVSSNLA CDR2(SEQ ID NO: 100)- GASTRAT CDR3(SEQ ID NO: 101)- QQYDDWPFT |
| ADI-27749 (A49) | EVQLVESGGGLVKPGGSLRLSCAAS GFTFSSYSMNWVRQAPGKGLEWVSS ISSSSSYIYYADSVKGRFTISRDNAKN SLYLQMNSLRAEDTAVYYCARGAP MGAAAGWFDPWGQGTLVTVSS (SEQ ID NO: 102) CDR1(SEQ ID NO: 104)-FTFSSYSMN CDR2(SEQ ID NO: 105)- SISSSSSYIYYADSVKG CDR3(SEQ ID NO: 106)- ARGAPMGAAAGWFDP | DIQMTQSPSSVSASVGDRVTITCR ASQGISSWLAWYQQKPGKAPKLL IYAASSLQSGVPSRFSGSGSGTDF TLTISSLQPEDFATYYCQQGVSFP RTFGGGTKVEIK (SEQ ID NO: 103) CDR1(SEQ ID NO: 107)- RASQGISSWLA CDR2(SEQ ID NO: 108)-AASSLQS CDR3(SEQ ID NO: 109)- QQGVSFPRT |

Alternatively, a heavy chain variable domain defined by SEQ ID NO:45 can be paired with a light chain variable domain defined by SEQ ID NO:46 to form an antigen-binding site that can bind to NKG2D, as illustrated in U.S. Pat. No. 9,273,136.

(SEQ ID NO: 45)
QVQLVESGGGLVKPGGSLRLSCAASGFTFSSYGMHWVRQAPGKGLEW

VAFIRYDGSNKYYADSVKGRFTISRDNSKNTLYLQMNSLRAEDTAVY

YCAKDRGLGDGTYFDYWGQGTTVTVSS (SEQ ID NO: 46)
QSALTQPASVSGSPGQSITISCSGSSSNIGNNAVNWYQQLPGKAPKL

LIYYDDLLPSGVSDRFSGSKSGTSAFLAISGLQSEDEADYYCAAWDD

SLNGPVFGGGTKLTVL

Alternatively, a heavy chain variable domain defined by SEQ ID NO:47 can be paired with a light chain variable domain defined by SEQ ID NO:48 to form an antigen-binding site that can bind to NKG2D, as illustrated in U.S. Pat. No. 7,879,985.

(SEQ ID NO: 47)
QVHLQESGPGLVKPSETLSLTCTVSDDSISSYYWSWIRQPPGKGLEW

IGHISYSGSANYNPSLKSRVTISVDTSKNQFSLKLSSVTAADTAVYY

CANWDDAFNIWGQGTMVTVSS (SEQ ID NO: 48)
EIVLTQSPGTLSLSPGERATLSCRASQSVSSSYLAWYQQKPGQAPRL

LIYGASSRATGIPDRFSGSGSGTDFTLTISRLEPEDFAVYYCQQYGS

SPWTFGQGTKVEIK

Table 2 lists peptide sequences of heavy chain variable domains and light chain variable domains that, in combination, can bind to HER2.

TABLE 2

| Clones | Heavy chain variable domain amino acid sequence | Light chain variable domain amino acid sequence |
| --- | --- | --- |
| Trastuzumab | EVQLVESGGGLVQPGGS LRLSCAASGFNIKDTYI HWVRQAPGKGLEWVARI YPTNGYTRYADSVKGRF TISADTSKNTAYLQMNS LRAEDTAVYYCSRWGGD GFYAMDYWGQGTLVTVS S(SEQ ID NO: 49) CDR1(SEQ ID NO: 50)-GFNIKDT CDR2(SEQ ID NO: 51)-YPTNGY CDR3(SEQ ID NO: 52)-WGGDGFYAMDY | DIQMTQSPSSLSASVGDR VTITCRASQDVNTAVAWY QQKPGKAPKLLIYSASFL YSGVPSRFSGSRSGTDFT LTISSLQPEDFATYYCQQ HYTTPPTFGQGTKVEIK (SEQ ID NO: 53) CDR1(SEQ ID NO: 54)-QDVNTAVA CDR2(SEQ ID NO: 55)-SASFLYS CDR3(SEQ ID NO: 56)-QQHYTTPPT |
| Pertuzumab | EVQLVESGGGLVQPGGS LRLSCAASGFTFTDYTM DWVRQAPGKGLEWVADV NPNSGGSIYNQRFKGRF TLSVDRSKNTLYLQMNS LRAEDTAVYYCARNLGP SFYFDYWGQGTLVTVSS A(SEQ ID NO: 57) CDR1(SEQ ID NO: 77)-GFTFTDY CDR2(SEQ ID NO: 78)-NPNSGG CDR3(SEQ ID NO: 79)-NLGPSFYFDY | DIQMTQSPSSLSASVGDR VTITCKASQDVSIGVAWY QQKPGKAPKLLIYSASYR YTGVPSRFSGSGSGTDFT LTISSLQPEDFATYYCQQ YYIYPYTFGQGTKVEIKR (SEQ ID NO: 58) CDR1(SEQ ID NO: 80)-QDVSIGVA CDR2(SEQ ID NO: 81)-SASYRYT CDR3(SEQ ID NO: 82)-QQYYIYPYT |
| MGAH22 (US 8,802,093) | QVQLQQSGPELVKPGAS LKLSCTASGFNIKDTYI HWVKQRPEQGLEWIGRI YPTNGYTRYDPKFQDKA TITADTSSNTAYLQVSR LTSEDTAVYYCSRWGGD GFYAMDYWGQGASVTVS SA (SEQ ID NO: 59) CDR1(SEQ ID NO: 83)-GFNIKDT CDR2(SEQ ID NO: 84)-YPTNGY CDR3(SEQ ID NO: 85)-WGGDGFYAMDY | DIVMTQSHKFMSTSVGDR VSITCKASQDVNTAVAWY QQKPGHSPKLLIYSASFR YTGVPDRFTGSRSGTDFT FTISSVQAEDLAVYYCQQ HYTTPPTFGGGTKVEIKR (SEQ ID NO: 60) CDR1(SEQ ID NO: 86)-QDVNTAVA CDR2(SEQ ID NO: 87)-SASFRYT CDR3(SEQ ID NO: 88)-QQHYTTPPT |

Alternatively, novel antigen-binding sites that can bind to HER2 can be identified by screening for binding to the amino acid sequence defined by SEQ ID NO:61.

(SEQ ID NO: 61)
MELAALCRWGLLLALLPPGAASTQVCTGTDMKLRLPASPETHLDMLR

HLYQGCQVVQGNLELTYLPTNASLSFLQDIQEVQGYVLIAHNQVRQV

PLQRLRIVRGTQLFEDNYALAVLDNGDPLNNTTPVTGASPGGLRELQ

LRSLTEILKGGVLIQRNPQLCYQDTILWKDIFHKNNQLALTLIDTNR

SRACHPCSPMCKGSRCWGESSEDCQSLTRTVCAGGCARCKGPLPTDC

CHEQCAAGCTGPKHSDCLACLHFNHSGICELHCPALVTYNTDTFESM

PNPEGRYTFGASCVTACPYNYLSTDVGSCTLVCPLHNQEVTAEDGTQ

RCEKCSKPCARVCYGLGMEHLREVRAVTSANIQEFAGCKKIFGSLAF

LPESFDGDPASNTAPLQPEQLQVFETLEEITGYLYISAWPDSLPDLS

VFQNLQVIRGRILHNGAYSLTLQGLGISWLGRSLRELGSGLALIHH

NTHLCFVHTVPWDQLFRNPHQALLHTANRPEDECVGEGLACHQLCAR

GHCWGPGPTQCVNCSQFLRGQECVEECRVLQGLPREYVNARHCLPCH

PECQPQNGSVTCFGPEADQCVACAHYKDPPFCVARCPSGVKPDLSYM

PIWKFPDEEGACQPCPINCTHSCVDLDDKGCPAEQRASPLTSIISAV

VGILLVVVLGVVFGILIKRRQQKIRKYTMRRLLQETELVEPLTPSGA

MPNQAQMRILKETELRKVKVLGSGAFGTVYKGIWIPDGENVKIPVAI

KVLRENTSPKANKEILDEAYVMAGVGSPYVSRLLGICLTSTVQLVTQ

LMPYGCLLDHVRENRGRLGSQDLLNWCMQIAKGMSYLEDVRLVHRDL

AARNVLVKSPNHVKITDFGLARLLDIDETEYHADGGKVPIKWMALES

ILRRRFTHQSDVWSYGVTVWELMTFGAKPYDGIPAREIPDLLEKGER

LPQPPICTIDVYMIMVKCWMIDSECRPRFRELVSEFSRMARDPQRFV

VIQNEDLGPASPLDSTFYRSLLEDDDMGDLVDAEEYLVPQQGFFCPD

PAPGAGGMVHHRRSSSTRSGGGDLTLGLEPSEEEAPRSPLAPSEGA

GSDVFDGDLGMGAAKGLQSLPTHDPSPLQRYSEDPTVPLPSETDGYV

-continued

APLTCSPQPEYVNQPDVRPQPPSPREGPLPAARPAGATLERPKTLSP

GKNGVVKDVFAFGGAVENPEYLTPQGGAAPQPHPPPAFSPAFDNLYY

WDQDPPERGAPPSTFKGTPTAENPEYLGLDVPV.

Within the Fc domain, CD16 binding is mediated by the hinge region and the CH2 domain. For example, within human IgG1, the interaction with CD16 is primarily focused on amino acid residues Asp 265-Glu 269, Asn 297-Thr 299, Ala 327-Ile 332, Leu 234-Ser 239, and carbohydrate residue N-acetyl-D-glucosamine in the CH2 domain (see, Sondermann et al, Nature, 406 (6793):267-273). Based on the known domains, mutations can be selected to enhance or reduce the binding affinity to CD16, such as by using phage-displayed libraries or yeast surface-displayed cDNA libraries, or can be designed based on the known three-dimensional structure of the interaction.

The assembly of heterodimeric antibody heavy chains can be accomplished by expressing two different antibody heavy chain sequences in the same cell, which may lead to the assembly of homodimers of each antibody heavy chain as well as assembly of heterodimers. Promoting the preferential assembly of heterodimers can be accomplished by incorporating different mutations in the CH3 domain of each antibody heavy chain constant region as shown in U.S. Ser. No. 13/494,870, U.S. Ser. No. 16/028,850, U.S. Ser. No. 11/533,709, U.S. Ser. No. 12/875,015, U.S. Ser. No. 13/289,934, U.S. Ser. No. 14/773,418, U.S. Ser. No. 12/811,207, U.S. Ser. No. 13/866,756, U.S. Ser. No. 14/647,480, and U.S. Ser. No. 14/830,336. For example, mutations can be made in the CH3 domain based on human IgG1 and incorporating distinct pairs of amino acid substitutions within a first polypeptide and a second polypeptide that allow these two chains to selectively heterodimerize with each other. The positions of amino acid substitutions illustrated below are all numbered according to the EU index as in Kabat.

In one scenario, an amino acid substitution in the first polypeptide replaces the original amino acid with a larger amino acid, selected from arginine (R), phenylalanine (F), tyrosine (Y) or tryptophan (W), and at least one amino acid substitution in the second polypeptide replaces the original amino acid(s) with a smaller amino acid(s), chosen from alanine (A), serine (S), threonine (T), or valine (V), such that the larger amino acid substitution (a protuberance) fits into the surface of the smaller amino acid substitutions (a cavity). For example, one polypeptide can incorporate a T366W substitution, and the other can incorporate three substitutions including T366S, L368A, and Y407V.

An antibody heavy chain variable domain of the invention can optionally be coupled to an amino acid sequence at least 90% identical to an antibody constant region, such as an IgG constant region including hinge, CH2 and CH3 domains with or without CH1 domain. In some embodiments, the amino acid sequence of the constant region is at least 90% identical to a human antibody constant region, such as an human IgG1 constant region, an IgG2 constant region, IgG3 constant region, or IgG4 constant region. In some other embodiments, the amino acid sequence of the constant region is at least 90% identical to an antibody constant region from another mammal, such as rabbit, dog, cat, mouse, or horse. One or more mutations can be incorporated into the constant region as compared to human IgG1 constant region, for example at Q347, Y349, L351, S354, E356, E357, K360, Q362, S364, T366, L368, K370, N390, K392, T394, D399, S400, D401, F405, Y407, K409, T411 and/or K439. Exemplary substitutions include, for example, Q347E, Q347R, Y349S, Y349K, Y349T, Y349D, Y349E, Y349C, T350V, L351K, L351D, L351Y, S354C, E356K, E357Q, E357L, E357W, K360E, K360W, Q362E, S364K, S364E, S364H, S364D, T366V, T366I, T366L, T366M, T366K, T366W, T366S, L368E, L368A, L368D, K370S, N390D, N390E, K392L, K392M, K392V, K392F, K392D, K392E, T394F, T394W, D399R, D399K, D399V, S400K, S400R, D401K, F405A, F405T, Y407A, Y407I, Y407V, K409F, K409W, K409D, T411D, T411E, K439D, and K439E.

In certain embodiments, mutations that can be incorporated into the CH1 of a human IgG1 constant region may be at amino acid V125, F126, P127, T135, T139, A140, F170, P171, and/or V173. In certain embodiments, mutations that can be incorporated into the Cκ of a human IgG1 constant region may be at amino acid E123, F116, S176, V163, S174, and/or T164.

Amino acid substitutions could be selected from the following sets of substitutions shown in Table 3.

TABLE 3

|  | First Polypeptide | Second Polypeptide |
| --- | --- | --- |
| Set 1 | S364E/F405A | Y349K/T394F |
| Set 2 | S364H/D401K | Y349T/T411E |
| Set 3 | S364H/T394F | Y349T/F405A |
| Set 4 | S364E/T394F | Y349K/F405A |
| Set 5 | S364E/T411E | Y349K/D401K |
| Set 6 | S364D/T394F | Y349K/F405A |
| Set 7 | S364H/F405A | Y349T/T394F |
| Set 8 | S364K/E357Q | L368D/K370S |
| Set 9 | L368D/K370S | S364K |
| Set 10 | L368E/K370S | S364K |
| Set 11 | K360E/Q362E | D401K |
| Set 12 | L368D/K370S | S364K/E357L |
| Set 13 | K370S | S364K/E357Q |
| Set 14 | F405L | K409R |
| Set 15 | K409R | F405L |

Alternatively, amino acid substitutions could be selected from the following sets of substitutions shown in Table 4.

TABLE 4

|  | First Polypeptide | Second Polypeptide |
| --- | --- | --- |
| Set 1 | K409W | D399V/F405T |
| Set 2 | Y349S | E357W |
| Set 3 | K360E | Q347R |
| Set 4 | K360E/K409W | Q347R/D399V/F405T |
| Set 5 | Q347E/K360E/K409W | Q347R/D399V/F405T |
| Set 6 | Y349S/K409W | E357W/D399V/F405T |

Alternatively, amino acid substitutions could be selected from the following set of substitutions shown in Table 5.

TABLE 5

|  | First Polypeptide | Second Polypeptide |
| --- | --- | --- |
| Set 1 | T366K/L351K | L351D/L368E |
| Set 2 | T366K/L351K | L351D/Y349E |
| Set 3 | T366K/L351K | L351D/Y349D |
| Set 4 | T366K/L351K | L351D/Y349E/L368E |
| Set 5 | T366K/L351K | L351D/Y349D/L368E |
| Set 6 | E356K/D399K | K392D/K409D |

Alternatively, at least one amino acid substitution in each polypeptide chain could be selected from Table 6.

TABLE 6

| First Polypeptide | Second Polypeptide |
|---|---|
| L351Y, D399R, D399K, S400K, S400R, Y407A, Y407I, Y407V | T366V, T366I, T366L, T366M, N390D, N390E, K392L, K392M, K392V, K392F, K392D, K392E, K409F, K409W, T411D and T411E |

Alternatively, at least one amino acid substitutions could be selected from the following set of substitutions in Table 7, where the position(s) indicated in the First Polypeptide column is replaced by any known negatively-charged amino acid, and the position(s) indicated in the Second Polypeptide Column is replaced by any known positively-charged amino acid.

TABLE 7

| First Polypeptide | Second Polypeptide |
|---|---|
| K392, K370, K409, or K439 | D399, E356, or E357 |

Alternatively, at least one amino acid substitutions could be selected from the following set of in Table 8, where the position(s) indicated in the First Polypeptide column is replaced by any known positively-charged amino acid, and the position(s) indicated in the Second Polypeptide Column is replaced by any known negatively-charged amino acid.

TABLE 8

| First Polypeptide | Second Polypeptide |
|---|---|
| D399, E356, or E357 | K409, K439, K370, or K392 |

Alternatively, amino acid substitutions could be selected from the following set in Table 9.

TABLE 9

| First Polypeptide | Second Polypeptide |
|---|---|
| T350V, L351Y, F405A, and Y407V | T350V, T366L, K392L, and T394W |

Alternatively, or in addition, the structural stability of a heteromultimer protein may be increased by introducing S354C on either of the first or second polypeptide chain, and Y349C on the opposing polypeptide chain, which forms an artificial disulfide bridge within the interface of the two polypeptides.

The multi-specific proteins described above can be made using recombinant DNA technology well known to a skilled person in the art. For example, a first nucleic acid sequence encoding the first immunoglobulin heavy chain can be cloned into a first expression vector; a second nucleic acid sequence encoding the second immunoglobulin heavy chain can be cloned into a second expression vector; a third nucleic acid sequence encoding the immunoglobulin light chain can be cloned into a third expression vector; the first, second, and third expression vectors can be stably transfected together into host cells to produce the multimeric proteins.

To achieve the highest yield of the multi-specific protein, different ratios of the first, second, and third expression vector can be explored to determine the optimal ratio for transfection into the host cells. After transfection, single clones can be isolated for cell bank generation using methods known in the art, such as limited dilution, ELISA, FACS, microscopy, or Clonepix.

Clones can be cultured under conditions suitable for bio-reactor scale-up and maintained expression of the multi-specific protein. The multi-specific proteins can be isolated and purified using methods known in the art including centrifugation, depth filtration, cell lysis, homogenization, freeze-thawing, affinity purification, gel filtration, ion exchange chromatography, hydrophobic interaction exchange chromatography, and mixed-mode chromatography.

II. Characteristics of the Multi-Specific Proteins

In certain embodiments, the multi-specific binding proteins described herein, which include an NKG2D-binding domain and a HER2-binding domain, bind to cells expressing human NKG2D. In certain embodiments, the multi-specific binding proteins which include an NKG2D-binding domain and a HER2-binding domain, bind to HER2 at a comparable level to that of a monoclonal antibody having the same HER2-binding domain. For example, the multi-specific binding proteins that include an NKG2D-binding domain and a HER2-binding domain from Trastuzumab can bind to HER2 expressed on cells at a level comparable to that of Trastuzumab.

Figure 36:
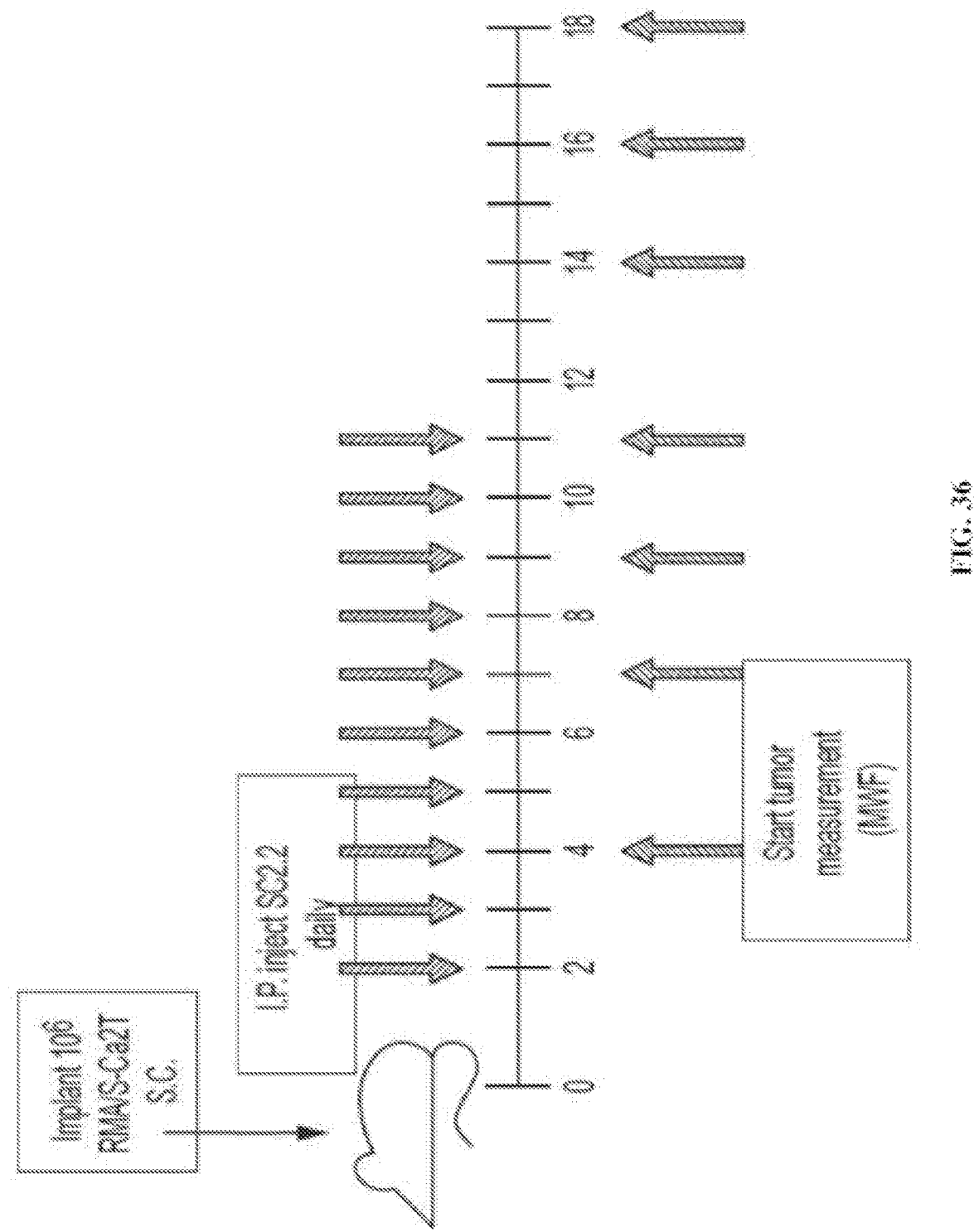
FIG. 36 is a flowchart of study design of RMA/S-HER2 subcutaneous SC2.2 efficacy.
Figure 37:
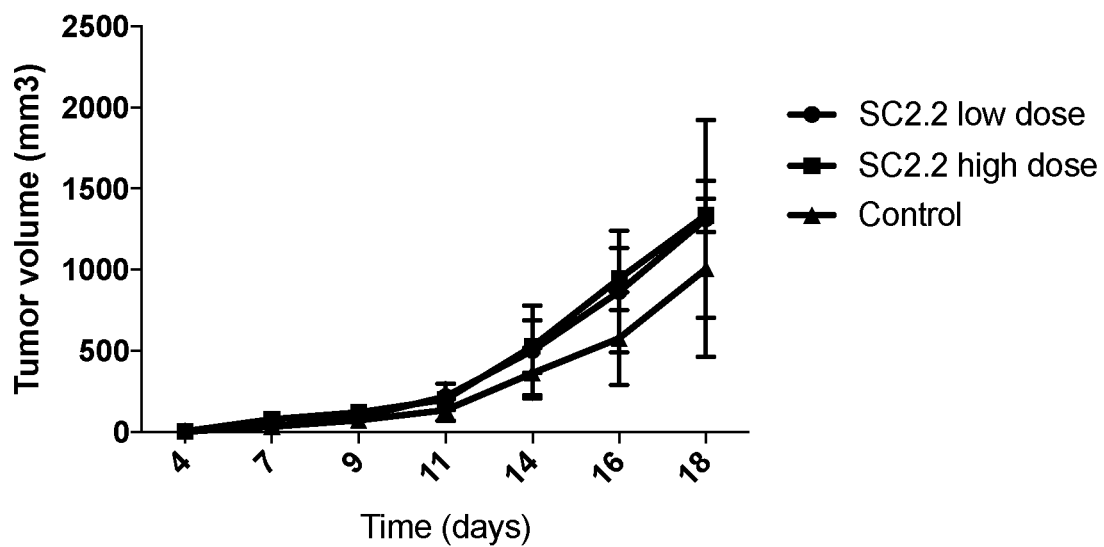
FIG. 37 are line graphs showing that SC2.2 has no effect on subcutaneous RMA/S-HER2 tumor growth.

However, the multi-specific binding proteins described herein are more effective in reducing tumor growth and killing cancer cells. For example, a multi-specific binding protein of the present disclosure that targets HER2-expressing tumor/cancer cells is more effective than SC2.2—a single chain bispecific molecule built from an scFv derived from trastuzumab linked to ULBP-6, a ligand for NKG2D. SC2.2 binds HER2+ cancer cells and NKG2D+ NK cells simultaneously. Therefore, effectiveness of SC2.2 in reducing HER2+ cancer cell number was investigated. In vitro activation and cytotoxity assays demonstrated that SC2.2 was effective in activating and killing NK cells. However, SC2.2 failed to demonstrate efficacy in the RMA/S-HER2 subcutaneous tumor model. The efficacy of SC2.2 was also tested in vivo using an RMA/S-HER2 overexpressing syngeneic mouse model (FIG. 36). In this mouse model, SC2.2 failed to demonstrate control of tumor growth compared to vehicle control (FIG. 37). Thus, although SC2.2 was able to activate and kill NK cells, and binds to HER2+ cancer cells, these properties were insufficient to effectively control HER2+ tumor growth.

In certain embodiments, the multi-specific binding proteins described herein, which include an NKG2D-binding domain and a binding domain for tumor associated antigen, activate primary human NK cells when culturing with tumor cells expressing the antigen. NK cell activation is marked by the increase in CD107a degranulation and IFNγ cytokine production. Furthermore, compared to a monoclonal antibody that includes the tumor associated antigen-binding domain, the multi-specific binding proteins show superior activation of human NK cells in the presence of tumor cells expressing the antigen. For example, compared to the monoclonal antibody trastuzumab, the multi-specific binding proteins of the present disclosure having a HER2-binding domain, have a superior activation of human NK cells in the presence of HER2-expressing cancer cells.

In certain embodiments, the multi-specific binding proteins described herein, which include an NKG2D-binding domain and a binding domain for a tumor associated antigen, enhance the activity of rested and IL-2-activated human NK cells in the presence of tumor cells expressing the antigen. Rested NK cells showed less background IFNγ production and CD107a degranulation than IL-2-activated NK cells. In certain embodiments, rested NK cells show a greater change in IFNγ production and CD107a degranulation compared to IL-2-activated NK cells. In certain embodiments, IL-2-activated NK cells show a greater percentage of cells becoming IFNγ+; CD107a+ after stimulation with TriNKETs.

In certain embodiments, the multi-specific binding proteins described herein, which include an NKG2D-binding domain and a binding domain for a tumor associated antigen (non-limiting examples of tumor associated antigens including CD20, BCMA, and HER2), enhance the cytotoxic activity of rested and IL-2-activated human NK cells in the presence of tumor cells expressing the antigen. Furthermore, the multi-specific binding proteins (e.g., A40-multi-specific binding protein, A49-multi-specific binding protein, C26-multi-specific binding protein, F04-multi-specific binding protein, F43-multi-specific binding protein, F47-multi-specific binding protein, and E79-multi-specific binding protein), which include a binding domain for HER2, more potently direct, activated and rested NK cell responses against the tumor cells, compared to a monoclonal antibody that includes HER2-binding site. In certain embodiments, the multi-specific binding proteins offer advantage against tumor cells expressing medium and low HER2, compared to monoclonal antibodies that HER2-binding site. Therefore, a therapy including multi-specific binding proteins can be superior to a monoclonal antibody therapy.

In certain embodiments, compared to monoclonal antibodies, the multi-specific binding proteins described herein (e.g., A40-multi-specific binding protein, A49-multi-specific binding protein, C26-multi-specific binding protein, F04-multi-specific binding protein, F43-multi-specific binding protein, F47-multi-specific binding protein, and E79-multi-specific binding protein), which include a binding domain for HER2 are advantageous in treating cancers with high expression of Fc receptor (FcR), or cancers residing in a tumor microenvironment with high levels of FcR. Monoclonal antibodies exert their effects on tumor growth through multiple mechanisms including ADCC, CDC, phagocytosis, and signal blockade amongst others. Amongst FcγRs, CD16 has the lowest affinity for IgG Fc; FcγRI (CD64) is the high-affinity FcR, which binds about 1000 times more strongly to IgG Fc than CD16. CD64 is normally expressed on many hematopoietic lineages such as the myeloid lineage, and can be expressed on tumors derived from these cell types, such as acute myeloid leukemia (AML). Immune cells infiltrating into the tumor, such as MDSCs and monocytes, also express CD64 and are known to infiltrate the tumor microenvironment. Expression of CD64 by the tumor or in the tumor microenvironment can have a detrimental effect on monoclonal antibody therapy. Expression of CD64 in the tumor microenvironment makes it difficult for these antibodies to engage CD16 on the surface of NK cells, as the antibodies prefer to bind the high-affinity receptor. The multi-specific binding proteins, through targeting two activating receptors on the surface of NK cells, can overcome the detrimental effect of CD64 expression (either on tumor or tumor microenvironment) on monoclonal antibody therapy. Regardless of CD64 expression on the tumor cells, the multi-specific binding proteins are able to mediate human NK cell responses against all tumor cells, because dual targeting of two activating receptors on NK cells provides stronger specific binding to NK cells.

In some embodiments, the multi-specific binding proteins described herein (e.g., A40-multi-specific binding protein, A49-multi-specific binding protein, C26-multi-specific binding protein, F04-multi-specific binding protein, F43-multi-specific binding protein, F47-multi-specific binding protein, and E79-multi-specific binding protein), which include a binding domain for HER2 provide a better safety profile through reduced on-target off-tumor side effects. Natural killer cells and CD8 T cells are both able to directly lyse tumor cells, although the mechanisms through which NK cells and CD8 T cell recognize normal self from tumor cells differ. The activity of NK cells is regulated by the balance of signals from activating (NCRs, NKG2D, CD16, etc.) and inhibitory (KIRs, NKG2A, etc.) receptors. The balance of these activating and inhibitory signals allow NK cells to determine healthy self-cells from stressed, virally infected, or transformed self-cells. This "built-in" mechanism of self-tolerance will help protect normal healthy tissue from NK cell responses. To extend this principle, the self-tolerance of NK cells will allow the multi-specific binding proteins to target antigens expressed both on self and tumor without off tumor side effects, or with an increased therapeutic window. Unlike natural killer cells, T cells require recognition of a specific peptide presented by MHC molecules for activation and effector functions. T cells have been the primary target of immunotherapy, and many strategies have been developed to redirect T cell responses against the tumor. T cell bispecifics, checkpoint inhibitors, and CAR-T cells have all been approved by the FDA, but often suffer from dose-limiting toxicities. T cell bispecifics and CAR-T cells work around the TCR-MHC recognition system by using binding domains to target antigens on the surface of tumor cells, and using engineered signaling domains to transduce the activation signals into the effector cell. Although effective at eliciting an anti-tumor immune response these therapies are often coupled with cytokine release syndrome (CRS), and on-target off-tumor side effects. The multi-specific binding proteins are unique in this context as they will not "override" the natural systems of NK cell activation and inhibition. Instead, the multi-specific binding proteins are designed to sway the balance, and provide additional activation signals to the NK cells, while maintaining NK tolerance to healthy self.

In some embodiments, the multi-specific binding proteins described herein including an NKG2D-binding domain (e.g., A40-multi-specific binding protein, A49-multi-specific binding protein, C26-multi-specific binding protein, F04-multi-specific binding protein, F43-multi-specific binding protein, F47-multi-specific binding protein, and E79-multi-specific binding protein), which include a binding domain for HER2 delay progression of the tumor more effectively than monoclonal antibodies that include the same tumor antigen-binding domain. In some embodiments, the multi-specific binding proteins including an NKG2D-binding domain and a tumor antigen-binding domain are more effective against cancer metastases than monoclonal antibodies that include the same tumor antigen-binding domain.

III. Therapeutic Applications

The invention provides methods for treating cancer using a multi-specific binding protein described herein and/or a pharmaceutical composition described herein. The methods may be used to treat a variety of cancers which express HER2 by administering to a patient in need thereof a therapeutically effective amount of a multi-specific binding protein described herein.

The therapeutic method can be characterized according to the cancer to be treated. For example, in certain embodiments, the cancer is breast, ovarian, esophageal, bladder or gastric cancer, salivary duct carcinoma, salivary duct carcinomas, adenocarcinoma of the lung or aggressive forms of uterine cancer, such as uterine serous endometrial carcinoma.

In certain other embodiments, the cancer is brain cancer, breast cancer, cervical cancer, colon cancer, colorectal cancer, endometrial cancer, esophageal cancer, leukemia, lung cancer, liver cancer, melanoma, ovarian cancer, pancreatic cancer, rectal cancer, renal cancer, stomach cancer, testicular cancer, or uterine cancer. In yet other embodiments, the cancer is a squamous cell carcinoma, adenocarcinoma, small cell carcinoma, melanoma, neuroblastoma, sarcoma (e.g., an angiosarcoma or chondrosarcoma), larynx cancer, parotid cancer, bilary tract cancer, thyroid cancer, acral lentiginous melanoma, actinic keratoses, acute lymphocytic leukemia, acute myeloid leukemia, adenoid cystic carcinoma, adenomas, adenosarcoma, adenosquamous carcinoma, anal canal cancer, anal cancer, anorectum cancer, astrocytic tumor, bartholin gland carcinoma, basal cell carcinoma, biliary cancer, bone cancer, bone marrow cancer, bronchial cancer, bronchial gland cancer, carcinoid, cholangiocarcinoma, chondosarcoma, choriod plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangiblastomas, hemangioendothelioma, hemangiomas, hepatic adenoma, hepatic adenomatosis, hepatobiliary cancer, hepatocellular carcinoma, Hodgkin's disease, ileum cancer, insulinoma, intaepithelial neoplasia, interepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancer, well differentiated carcinoma, or Wilms tumor.

In certain other embodiments, the cancer is non-Hodgkin's lymphoma, such as a B-cell lymphoma or a T-cell lymphoma. In certain embodiments, the non-Hodgkin's lymphoma is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, or primary central nervous system (CNS) lymphoma. In certain other embodiments, the non-Hodgkin's lymphoma is a T-cell lymphoma, such as a precursor T-lymphoblastic lymphoma, peripheral T-cell lymphoma, cutaneous T-cell lymphoma, angioimmunoblastic T-cell lymphoma, extranodal natural killer/T-cell lymphoma, enteropathy type T-cell lymphoma, subcutaneous panniculitis-like T-cell lymphoma, anaplastic large cell lymphoma, or peripheral T-cell lymphoma.

The cancer to be treated can be characterized according to the presence of a particular antigen expressed on the surface of the cancer cell. In certain embodiments, the cancer cell can express one or more of the following in addition to HER2: CD2, CD19, CD20, CD30, CD38, CD40, CD52, CD70, EGFR/ERBB1, IGF1R, HER3/ERBB3, HER4/ERBB4, MUC1, cMET, SLAMF7, PSCA, MICA, MICB, TRAILR1, TRAILR2, MAGE-A3, B7.1, B7.2, CTLA4, and PD1.

IV. Combination Therapy

Another aspect of the invention provides for combination therapy. Multi-specific binding proteins described herein be used in combination with additional therapeutic agents to treat the cancer.

Exemplary therapeutic agents that may be used as part of a combination therapy in treating cancer, include, for example, radiation, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, luteinizing hormone releasing factor and variations of the aforementioned agents that may exhibit differential binding to its cognate receptor, and increased or decreased serum half-life.

An additional class of agents that may be used as part of a combination therapy in treating cancer is immune checkpoint inhibitors. Exemplary immune checkpoint inhibitors include agents that inhibit one or more of (i) cytotoxic T-lymphocyte-associated antigen 4 (CTLA4), (ii) programmed cell death protein 1 (PD1), (iii) PDL1, (iv) LAG3, (v) B7-H3, (vi) B7-H4, and (vii) TIM3. The CTLA4 inhibitor ipilimumab has been approved by the United States Food and Drug Administration for treating melanoma.

Yet other agents that may be used as part of a combination therapy in treating cancer are monoclonal antibody agents that target non-checkpoint targets (e.g., herceptin) and non-cytotoxic agents (e.g., tyrosine-kinase inhibitors).

Yet other categories of anti-cancer agents include, for example: (i) an inhibitor selected from an ALK Inhibitor, an ATR Inhibitor, an A2A Antagonist, a Base Excision Repair Inhibitor, a Bcr-Abl Tyrosine Kinase Inhibitor, a Bruton's Tyrosine Kinase Inhibitor, a CDC7 Inhibitor, a CHK1 Inhibitor, a Cyclin-Dependent Kinase Inhibitor, a DNA-PK Inhibitor, an Inhibitor of both DNA-PK and mTOR, a DNMT1 Inhibitor, a DNMT1 Inhibitor plus 2-chloro-deoxy-adenosine, an HDAC Inhibitor, a Hedgehog Signaling Pathway Inhibitor, an IDO Inhibitor, a JAK Inhibitor, a mTOR Inhibitor, a MEK Inhibitor, a MELK Inhibitor, a MTH1 Inhibitor, a PARP Inhibitor, a Phosphoinositide 3-Kinase Inhibitor, an Inhibitor of both PARP1 and DHODH, a Proteasome Inhibitor, a Topoisomerase-II Inhibitor, a Tyrosine Kinase Inhibitor, a VEGFR Inhibitor, and a WEE1 Inhibitor; (ii) an agonist of OX40, CD137, CD40, GITR, CD27, HVEM, TNFRSF25, or ICOS; and (iii) a cytokine selected from IL-12, IL-15, GM-CSF, and G-CSF.

Proteins of the invention can also be used as an adjunct to surgical removal of the primary lesion.

The amount of multi-specific binding protein and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a multi-specific binding protein may be administered during a time when the additional therapeutic agent(s) exerts its prophylactic or therapeutic effect, or vice versa.

V. Pharmaceutical Compositions

The present disclosure also features pharmaceutical compositions that contain a therapeutically effective amount of a protein described herein. The composition can be formulated for use in a variety of drug delivery systems. One or more physiologically acceptable excipients or carriers can also be included in the composition for proper formulation. Suitable formulations for use in the present disclosure are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

The intravenous drug delivery formulation of the present disclosure may be contained in a bag, a pen, or a syringe. In certain embodiments, the bag may be connected to a channel comprising a tube and/or a needle. In certain embodiments, the formulation may be a lyophilized formulation or a liquid formulation. In certain embodiments, the formulation may freeze-dried (lyophilized) and contained in about 12-60 vials. In certain embodiments, the formulation may be freeze-dried and 45 mg of the freeze-dried formulation may be contained in one vial. In certain embodiments, the about 40 mg-about 100 mg of freeze-dried formulation may be contained in one vial. In certain embodiments, freeze dried formulation from 12, 27, or 45 vials are combined to obtained a therapeutic dose of the protein in the intravenous drug formulation. In certain embodiments, the formulation may be a liquid formulation and stored as about 250 mg/vial to about 1000 mg/vial. In certain embodiments, the formulation may be a liquid formulation and stored as about 600 mg/vial. In certain embodiments, the formulation may be a liquid formulation and stored as about 250 mg/vial.

This present disclosure could exist in a liquid aqueous pharmaceutical formulation including a therapeutically effective amount of the protein in a buffered solution forming a formulation.

These compositions may be sterilized by conventional sterilization techniques, or may be sterile filtered. The resulting aqueous solutions may be packaged for use as-is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents. The composition in solid form can also be packaged in a container for a flexible quantity.

In certain embodiments, the present disclosure provides a formulation with an extended shelf life including the protein of the present disclosure, in combination with mannitol, citric acid monohydrate, sodium citrate, disodium phosphate dihydrate, sodium dihydrogen phosphate dihydrate, sodium chloride, polysorbate 80, water, and sodium hydroxide.

In certain embodiments, an aqueous formulation is prepared including the protein of the present disclosure in a pH-buffered solution. The buffer of this invention may have a pH ranging from about 4 to about 8, e.g., from about 4.5 to about 6.0, or from about 4.8 to about 5.5, or may have a pH of about 5.0 to about 5.2. Ranges intermediate to the above recited pH's are also intended to be part of this disclosure. For example, ranges of values using a combination of any of the above recited values as upper and/or lower limits are intended to be included. Examples of buffers that will control the pH within this range include acetate (e.g. sodium acetate), succinate (such as sodium succinate), gluconate, histidine, citrate and other organic acid buffers.

In certain embodiments, the formulation includes a buffer system which contains citrate and phosphate to maintain the pH in a range of about 4 to about 8. In certain embodiments the pH range may be from about 4.5 to about 6.0, or from about pH 4.8 to about 5.5, or in a pH range of about 5.0 to about 5.2. In certain embodiments, the buffer system includes citric acid monohydrate, sodium citrate, disodium phosphate dihydrate, and/or sodium dihydrogen phosphate dihydrate. In certain embodiments, the buffer system includes about 1.3 mg/ml of citric acid (e.g., 1.305 mg/ml), about 0.3 mg/ml of sodium citrate (e.g., 0.305 mg/ml), about 1.5 mg/ml of disodium phosphate dihydrate (e.g., 1.53 mg/ml), about 0.9 mg/ml of sodium dihydrogen phosphate dihydrate (e.g., 0.86), and about 6.2 mg/ml of sodium chloride (e.g., 6.165 mg/ml). In certain embodiments, the buffer system includes 1-1.5 mg/ml of citric acid, 0.25 to 0.5 mg/ml of sodium citrate, 1.25 to 1.75 mg/ml of disodium phosphate dihydrate, 0.7 to 1.1 mg/ml of sodium dihydrogen phosphate dihydrate, and 6.0 to 6.4 mg/ml of sodium chloride. In certain embodiments, the pH of the formulation is adjusted with sodium hydroxide.

A polyol, which acts as a tonicifier and may stabilize the antibody, may also be included in the formulation. The polyol is added to the formulation in an amount which may vary with respect to the desired isotonicity of the formulation. In certain embodiments, the aqueous formulation may be isotonic. The amount of polyol added may also be altered with respect to the molecular weight of the polyol. For example, a lower amount of a monosaccharide (e.g., mannitol) may be added, compared to a disaccharide (such as trehalose). In certain embodiments, the polyol which may be used in the formulation as a tonicity agent is mannitol. In certain embodiments, the mannitol concentration may be about 5 to about 20 mg/ml. In certain embodiments, the concentration of mannitol may be about 7.5 to 15 mg/ml. In certain embodiments, the concentration of mannitol may be about 10-14 mg/ml. In certain embodiments, the concentration of mannitol may be about 12 mg/ml. In certain embodiments, the polyol sorbitol may be included in the formulation.

A detergent or surfactant may also be added to the formulation. Exemplary detergents include nonionic detergents such as polysorbates (e.g., polysorbates 20, 80 etc.) or poloxamers (e.g., poloxamer 188). The amount of detergent added is such that it reduces aggregation of the formulated antibody and/or minimizes the formation of particulates in the formulation and/or reduces adsorption. In certain embodiments, the formulation may include a surfactant which is a polysorbate. In certain embodiments, the formulation may contain the detergent polysorbate 80 or Tween 80. Tween 80 is a term used to describe polyoxyethylene (20) sorbitanmonooleate (see Fiedler, Lexikon der Hifsstoffe, Editio Cantor Verlag Aulendorf, 4th edi., 1996). In certain embodiments, the formulation may contain between about 0.1 mg/mL and about 10 mg/mL of polysorbate 80, or between about 0.5 mg/mL and about 5 mg/mL. In certain embodiments, about 0.1% polysorbate 80 may be added in the formulation.

In embodiments, the protein product of the present disclosure is formulated as a liquid formulation. The liquid formulation may be presented at a 10 mg/mL concentration in either a USP/Ph Eur type I 50R vial closed with a rubber stopper and sealed with an aluminum crimp seal closure. The stopper may be made of elastomer complying with USP and Ph Eur. In certain embodiments vials may be filled with 61.2 mL of the protein product solution in order to allow an extractable volume of 60 mL. In certain embodiments, the liquid formulation may be diluted with 0.9% saline solution.

In certain embodiments, the liquid formulation of the disclosure may be prepared as a 10 mg/mL concentration solution in combination with a sugar at stabilizing levels. In certain embodiments the liquid formulation may be prepared in an aqueous carrier. In certain embodiments, a stabilizer may be added in an amount no greater than that which may result in a viscosity undesirable or unsuitable for intravenous administration. In certain embodiments, the sugar may be disaccharides, e.g., sucrose. In certain embodiments, the liquid formulation may also include one or more of a buffering agent, a surfactant, and a preservative.

In certain embodiments, the pH of the liquid formulation may be set by addition of a pharmaceutically acceptable acid and/or base. In certain embodiments, the pharmaceutically acceptable acid may be hydrochloric acid. In certain embodiments, the base may be sodium hydroxide.

In addition to aggregation, deamidation is a common product variant of peptides and proteins that may occur during fermentation, harvest/cell clarification, purification, drug substance/drug product storage and during sample analysis. Deamidation is the loss of $NH_3$ from a protein forming a succinimide intermediate that can undergo hydrolysis. The succinimide intermediate results in a 17 dalton mass decrease of the parent peptide. The subsequent hydrolysis results in an 18 dalton mass increase. Isolation of the succinimide intermediate is difficult due to instability under aqueous conditions. As such, deamidation is typically detectable as 1 dalton mass increase. Deamidation of an asparagine results in either aspartic or isoaspartic acid. The parameters affecting the rate of deamidation include pH, temperature, solvent dielectric constant, ionic strength, primary sequence, local polypeptide conformation and tertiary structure. The amino acid residues adjacent to Asn in the peptide chain affect deamidation rates. Gly and Ser following an Asn in protein sequences results in a higher susceptibility to deamidation.

In certain embodiments, the liquid formulation of the present disclosure may be preserved under conditions of pH and humidity to prevent deamination of the protein product.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

A preservative may be optionally added to the formulations herein to reduce bacterial action. The addition of a preservative may, for example, facilitate the production of a multi-use (multiple-dose) formulation.

Intravenous (IV) formulations may be the preferred administration route in particular instances, such as when a patient is in the hospital after transplantation receiving all drugs via the IV route. In certain embodiments, the liquid formulation is diluted with 0.9% Sodium Chloride solution before administration. In certain embodiments, the diluted drug product for injection is isotonic and suitable for administration by intravenous infusion.

In certain embodiments, a salt or buffer components may be added in an amount of 10 mM-200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

A preservative may be optionally added to the formulations herein to reduce bacterial action. The addition of a preservative may, for example, facilitate the production of a multi-use (multiple-dose) formulation.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

This present disclosure could exist in a lyophilized formulation including the proteins and a lyoprotectant. The lyoprotectant may be sugar, e.g., disaccharides. In certain embodiments, the lyoprotectant may be sucrose or maltose. The lyophilized formulation may also include one or more of a buffering agent, a surfactant, a bulking agent, and/or a preservative.

The amount of sucrose or maltose useful for stabilization of the lyophilized drug product may be in a weight ratio of at least 1:2 protein to sucrose or maltose. In certain embodiments, the protein to sucrose or maltose weight ratio may be of from 1:2 to 1:5.

In certain embodiments, the pH of the formulation, prior to lyophilization, may be set by addition of a pharmaceutically acceptable acid and/or base. In certain embodiments the pharmaceutically acceptable acid may be hydrochloric acid. In certain embodiments, the pharmaceutically acceptable base may be sodium hydroxide.

Before lyophilization, the pH of the solution containing the protein of the present disclosure may be adjusted between 6 to 8. In certain embodiments, the pH range for the lyophilized drug product may be from 7 to 8.

In certain embodiments, a salt or buffer components may be added in an amount of 10 mM-200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

In certain embodiments, a "bulking agent" may be added. A "bulking agent" is a compound which adds mass to a lyophilized mixture and contributes to the physical structure of the lyophilized cake (e.g., facilitates the production of an essentially uniform lyophilized cake which maintains an open pore structure). Illustrative bulking agents include mannitol, glycine, polyethylene glycol and sorbitol. The lyophilized formulations of the present invention may contain such bulking agents.

A preservative may be optionally added to the formulations herein to reduce bacterial action. The addition of a preservative may, for example, facilitate the production of a multi-use (multiple-dose) formulation.

In certain embodiments, the lyophilized drug product may be constituted with an aqueous carrier. The aqueous carrier of interest herein is one which is pharmaceutically acceptable (e.g., safe and non-toxic for administration to a human) and is useful for the preparation of a liquid formulation, after lyophilization. Illustrative diluents include sterile water for injection (SWFI), bacteriostatic water for injection (BWFI), a pH buffered solution (e.g., phosphate-buffered saline), sterile saline solution, Ringer's solution or dextrose solution.

In certain embodiments, the lyophilized drug product of the current disclosure is reconstituted with either Sterile Water for Injection, USP (SWFI) or 0.9% Sodium Chloride Injection, USP. During reconstitution, the lyophilized powder dissolves into a solution.

In certain embodiments, the lyophilized protein product of the instant disclosure is constituted to about 4.5 mL water for injection and diluted with 0.9% saline solution (sodium chloride solution).

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The specific dose can be a uniform dose for each patient, for example, 50-5000 mg of protein. Alternatively, a patient's dose can be tailored to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., *Clinica Chimica Acta* 308: 43-53, 2001; Steimer et al., *Clinica Chimica Acta* 308: 33-41, 2001).

In general, dosages based on body weight are from about 0.01 µg to about 100 mg per kg of body weight, such as about 0.01 µg to about 100 mg/kg of body weight, about 0.01 µg to about 50 mg/kg of body weight, about 0.01 µg to about 10 mg/kg of body weight, about 0.01 µg to about 1 mg/kg of body weight, about 0.01 µg to about 100 µg/kg of body weight, about 0.01 µg to about 50 µg/kg of body weight, about 0.01 µg to about 10 µg/kg of body weight, about 0.01 µg to about 1 µg/kg of body weight, about 0.01 µg to about 0.1 µg/kg of body weight, about 0.1 µg to about 100 mg/kg of body weight, about 0.1 µg to about 50 mg/kg of body weight, about 0.1 µg to about 10 mg/kg of body weight, about 0.1 µg to about 1 mg/kg of body weight, about 0.1 µg to about 100 µg/kg of body weight, about 0.1 µg to about 10 µg/kg of body weight, about 0.1 µg to about 1 µg/kg of body weight, about 1 µg to about 100 mg/kg of body weight, about 1 µg to about 50 mg/kg of body weight, about 1 µg to about 10 mg/kg of body weight, about 1 µg to about 1 mg/kg of body weight, about 1 µg to about 100 µg/kg of body weight, about 1 µg to about 50 µg/kg of body weight, about 1 µg to about 10 µg/kg of body weight, about 10 µg to about 100 mg/kg of body weight, about 10 µg to about 50 mg/kg of body weight, about 10 µg to about 10 mg/kg of body weight, about 10 µg to about 1 mg/kg of body weight, about 10 µg to about 100 µg/kg of body weight, about 10 µg to about 50 µg/kg of body weight, about 50 µg to about 100 mg/kg of body weight, about 50 µg to about 50 mg/kg of body weight, about 50 µg to about 10 mg/kg of body weight, about 50 µg to about 1 mg/kg of body weight, about 50 µg to about 100 µg/kg of body weight, about 100 µg to about 100 mg/kg of body weight, about 100 µg to about 50 mg/kg of body weight, about 100 µg to about 10 mg/kg of body weight, about 100 µg to about 1 mg/kg of body weight, about 1 mg to about 100 mg/kg of body weight, about 1 mg to about 50 mg/kg of body weight, about 1 mg to about 10 mg/kg of body weight, about 10 mg to about 100 mg/kg of body weight, about 10 mg to about 50 mg/kg of body weight, about 50 mg to about 100 mg/kg of body weight.

Doses may be given once or more times daily, weekly, monthly or yearly, or even once every 2 to 20 years. Persons of ordinary skill in the art can easily estimate repetition rates for dosing based on measured residence times and concentrations of the targetable construct or complex in bodily fluids or tissues. Administration of the present invention could be intravenous, intraarterial, intraperitoneal, intramuscular, subcutaneous, intrapleural, intrathecal, intracavitary, by perfusion through a catheter or by direct intralesional injection. This may be administered once or more times daily, once or more times weekly, once or more times monthly, and once or more times annually.

The description above describes multiple aspects and embodiments of the invention. The patent application specifically contemplates all combinations and permutations of the aspects and embodiments.

EXAMPLES

The invention now being generally described, will be more readily understood by reference to the following examples, which are included merely for purposes of illustration of certain aspects and embodiments of the present invention, and is not intended to limit the invention.

Example 1—NKG2D-Binding Domains Bind to NKG2D

NKG2D-Binding Domains Bind to Purified Recombinant NKG2D

The nucleic acid sequences of human, mouse or cynomolgus NKG2D ectodomains were fused with nucleic acid sequences encoding human IgG1 Fc domains and introduced into mammalian cells to be expressed. After purification, NKG2D-Fc fusion proteins were adsorbed to wells of microplates. After blocking the wells with bovine serum albumin to prevent non-specific binding, NKG2D-binding domains were titrated and added to the wells pre-adsorbed with NKG2D-Fc fusion proteins. Primary antibody binding was detected using a secondary antibody which was conjugated to horseradish peroxidase and specifically recognizes a human kappa light chain to avoid Fc cross-reactivity. 3,3', 5,5'-Tetramethylbenzidine (TMB), a substrate for horseradish peroxidase, was added to the wells to visualize the binding signal, whose absorbance was measured at 450 nM and corrected at 540 nM. An NKG2D-binding domain clone, an isotype control or a positive control (selected from SEQ ID NOs:45-48, or anti-mouse NKG2D clones MI-6 and CX-5 available at eBioscience) was added to each well.

Figure 3:
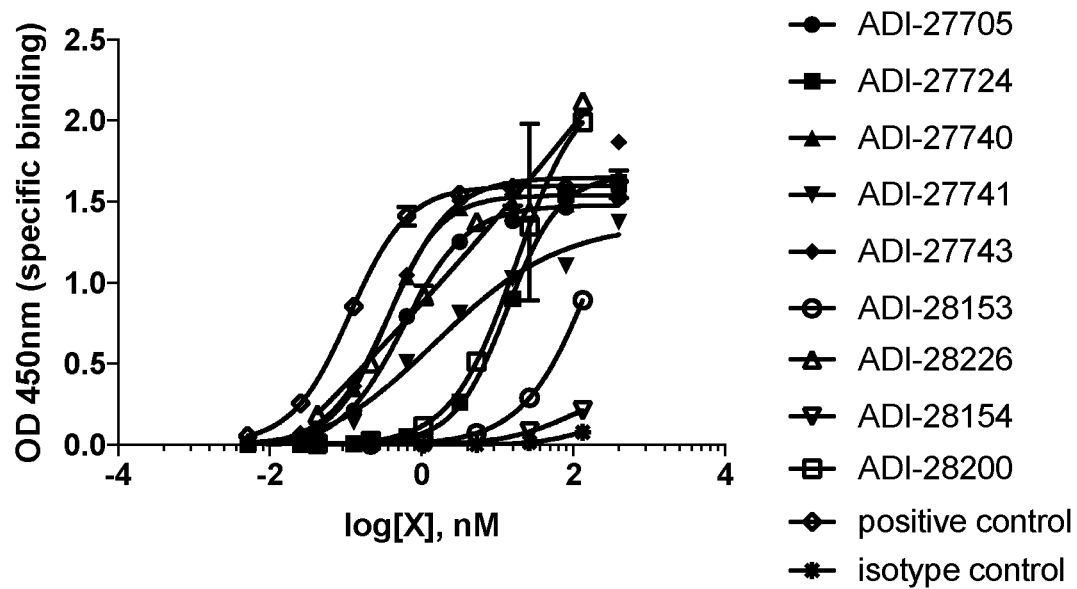
FIG. 3 are line graphs demonstrating the binding affinity of NKG2D-binding domains (listed as clones) to human recombinant NKG2D in an ELISA assay.
Figure 4:
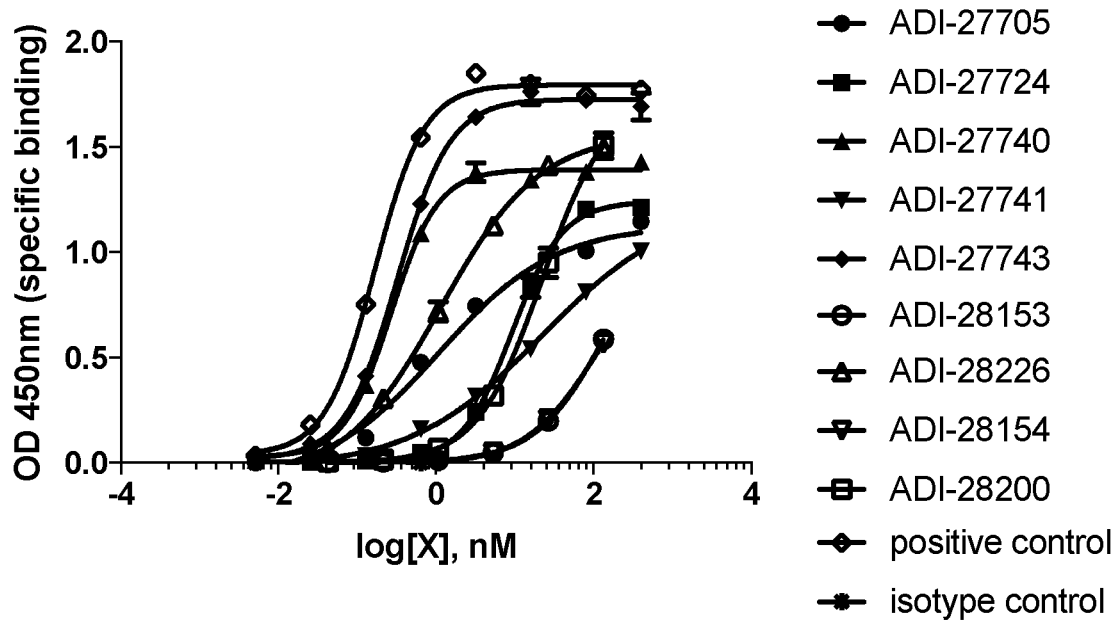
FIG. 4 are line graphs demonstrating the binding affinity of NKG2D-binding domains (listed as clones) to cynomolgus recombinant NKG2D in an ELISA assay.
Figure 5:
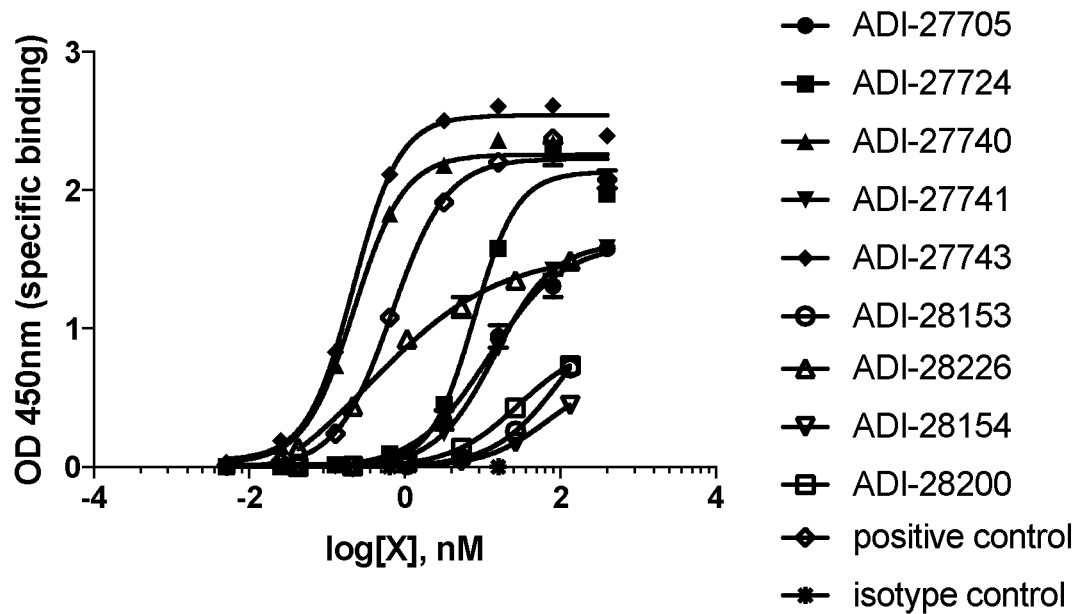
FIG. 5 are line graphs demonstrating the binding affinity of NKG2D-binding domains (listed as clones) to mouse recombinant NKG2D in an ELISA assay.

The isotype control showed minimal binding to recombinant NKG2D-Fc proteins, while the positive control bound strongest to the recombinant antigens. NKG2D-binding domains produced by all clones demonstrated binding across human, mouse, and cynomolgus recombinant NKG2D-Fc proteins, although with varying affinities from clone to clone. Generally, each anti-NKG2D clone bound to human (FIG. 3) and cynomolgus (FIG. 4) recombinant NKG2D-Fc with similar affinity, but with lower affinity to mouse (FIG. 5) recombinant NKG2D-Fc.

NKG2D-Binding Domains Bind to Cells Expressing NKG2D

EL4 mouse lymphoma cell lines were engineered to express human or mouse NKG2D-CD3 zeta signaling domain chimeric antigen receptors. An NKG2D-binding clone, an isotype control or a positive control was used at a 100 nM concentration to stain extracellular NKG2D expressed on the EL4 cells. The antibody binding was detected using fluorophore-conjugated anti-human IgG secondary antibodies. Cells were analyzed by flow cytometry, and fold-over-background (FOB) was calculated using the mean fluorescence intensity (MFI) of NKG2D-expressing cells compared to parental EL4 cells.

Figure 6:
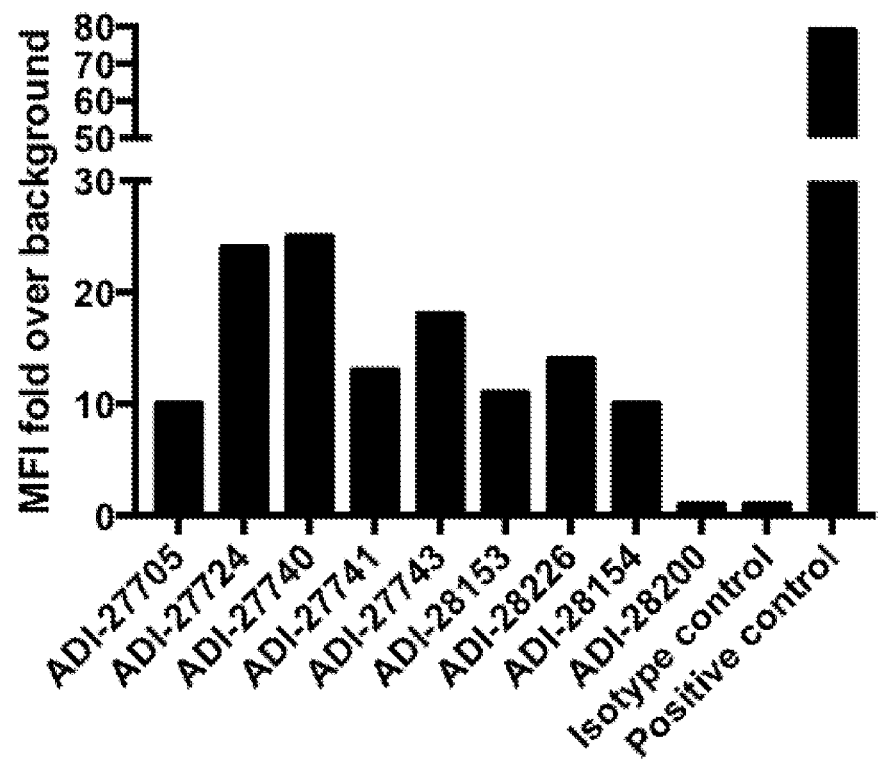
FIG. 6 are bar graphs demonstrating the binding of NKG2D-binding domains (listed as clones) to EL4 cells expressing human NKG2D by flow cytometry showing mean fluorescence intensity (MFI) fold over background.
Figure 7:
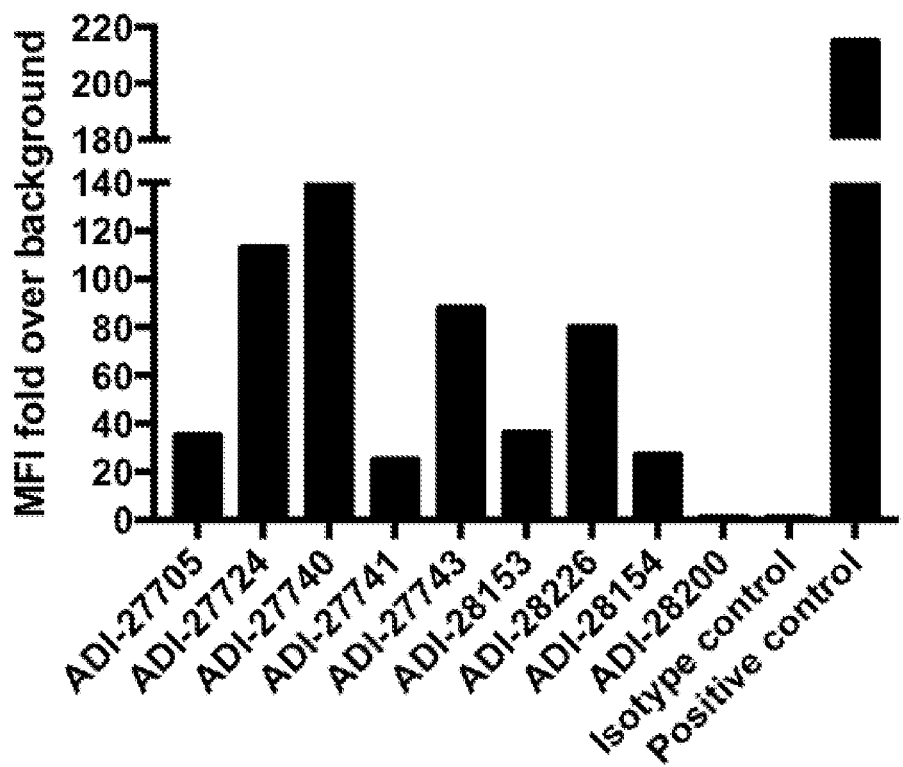
FIG. 7 are bar graphs demonstrating the binding of NKG2D-binding domains (listed as clones) to EL4 cells expressing mouse NKG2D by flow cytometry showing mean fluorescence intensity (MFI) fold over background.

NKG2D-binding domains produced by all clones bound to EL4 cells expressing human and mouse NKG2D. Positive control antibodies (selected from SEQ ID NO: 45-48, or anti-mouse NKG2D clones MI-6 and CX-5 available at eBioscience) gave the best FOB binding signal. The NKG2D-binding affinity for each clone was similar between cells expressing human NKG2D (FIG. 6) and mouse (FIG. 7) NKG2D.

Example 2—NKG2D-Binding Domains Block Natural Ligand Binding to NKG2D

Competition with ULBP-6

Figure 8:
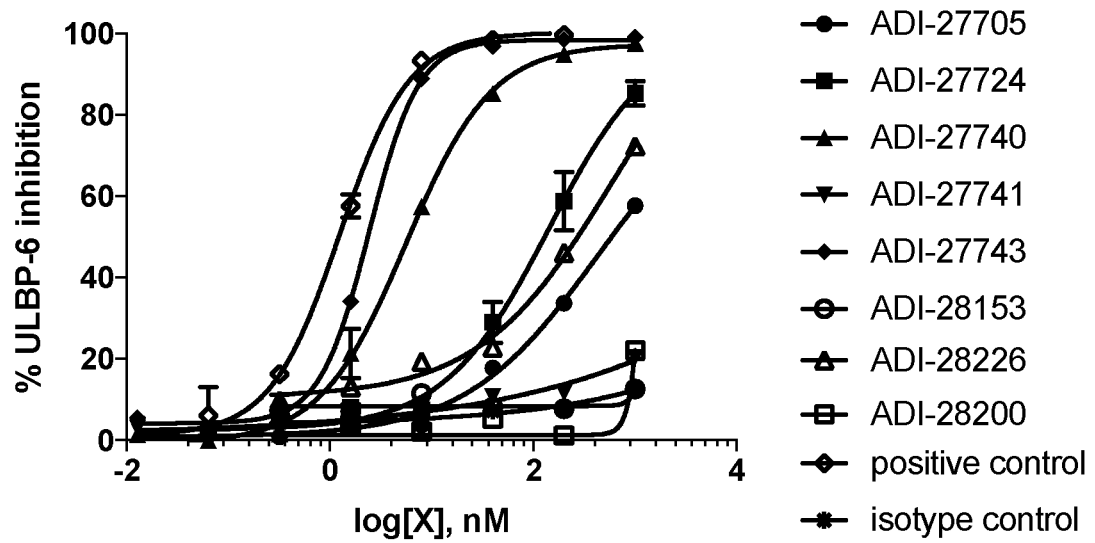
FIG. 8 are line graphs demonstrating specific binding affinity of NKG2D-binding domains (listed as clones) to recombinant human NKG2D-Fc by competing with natural ligand ULBP-6.

Recombinant human NKG2D-Fc proteins were adsorbed to wells of a microplate, and the wells were blocked with bovine serum albumin reduce non-specific binding. A saturating concentration of ULBP-6-His-biotin was added to the wells, followed by addition of the NKG2D-binding domain clones. After a 2-hour incubation, wells were washed and ULBP-6-His-biotin that remained bound to the NKG2D-Fc coated wells was detected by streptavidin-conjugated to horseradish peroxidase and TMB substrate. Absorbance was measured at 450 nM and corrected at 540 nM. After subtracting background, specific binding of NKG2D-binding domains to the NKG2D-Fc proteins was calculated from the percentage of ULBP-6-His-biotin that was blocked from binding to the NKG2D-Fc proteins in wells. The positive control antibody (selected from SEQ ID NOs:45-48) and various NKG2D-binding domains blocked ULBP-6 binding to NKG2D, while isotype control showed little competition with ULBP-6 (FIG. 8).

Competition with MICA

Figure 9:
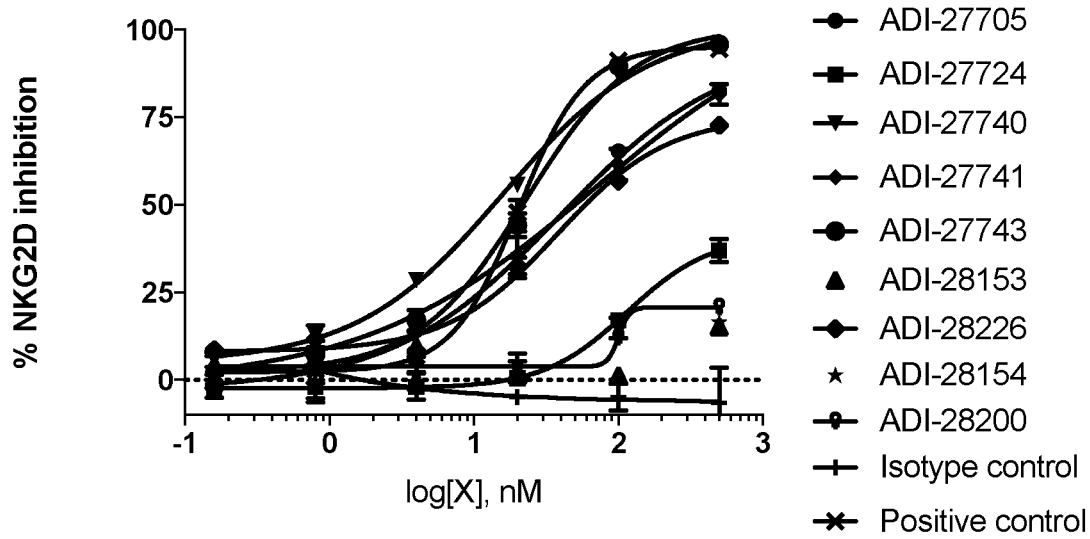
FIG. 9 are line graphs demonstrating specific binding affinity of NKG2D-binding domains (listed as clones) to recombinant human NKG2D-Fc by competing with natural ligand MICA.

Recombinant human MICA-Fc proteins were adsorbed to wells of a microplate, and the wells were blocked with bovine serum albumin to reduce non-specific binding. NKG2D-Fc-biotin was added to wells followed by NKG2D-binding domains. After incubation and washing, NKG2D-Fc-biotin that remained bound to MICA-Fc coated wells was detected using streptavidin-HRP and TMB substrate. Absorbance was measured at 450 nM and corrected at 540 nM. After subtracting background, specific binding of NKG2D-binding domains to the NKG2D-Fc proteins was calculated from the percentage of NKG2D-Fc-biotin that was blocked from binding to the MICA-Fc coated wells. The positive control antibody (selected from SEQ ID NOs:45-48) and various NKG2D-binding domains blocked MICA binding to NKG2D, while isotype control showed little competition with MICA (FIG. 9).

Competition with Rae-1 Delta

Figure 10:
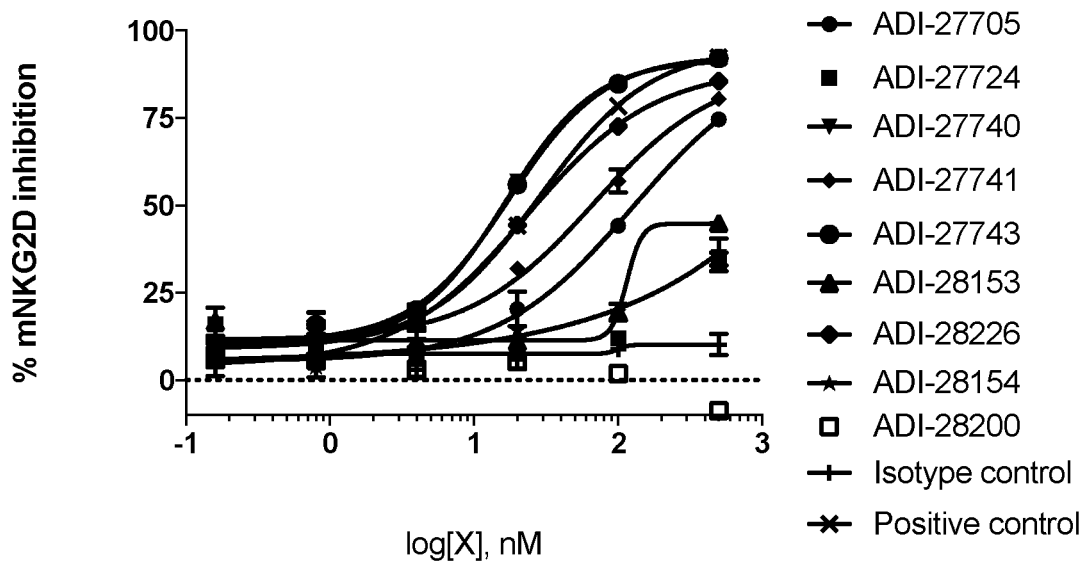
FIG. 10 are line graphs demonstrating specific binding affinity of NKG2D-binding domains (listed as clones) to recombinant mouse NKG2D-Fc by competing with natural ligand Rae-1 delta.

Recombinant mouse Rae-1delta-Fc (purchased from R&D Systems) was adsorbed to wells of a microplate, and the wells were blocked with bovine serum albumin to reduce non-specific binding. Mouse NKG2D-Fc-biotin was added to the wells followed by NKG2D-binding domains. After incubation and washing, NKG2D-Fc-biotin that remained bound to Rae-1delta-Fc coated wells was detected using streptavidin-HRP and TMB substrate. Absorbance was measured at 450 nM and corrected at 540 nM. After subtracting background, specific binding of NKG2D-binding domains to the NKG2D-Fc proteins was calculated from the percentage of NKG2D-Fc-biotin that was blocked from binding to the Rae-1delta-Fc coated wells. The positive control (selected from SEQ ID NOs:45-48, or anti-mouse NKG2D clones MI-6 and CX-5 available at eBioscience) and various NKG2D-binding domain clones blocked Rae-1delta binding to mouse NKG2D, while the isotype control antibody showed little competition with Rae-1delta (FIG. 10).

Example 3—NKG2D-Binding Domain Clones Activate NKG2D

Nucleic acid sequences of human and mouse NKG2D were fused to nucleic acid sequences encoding a CD3 zeta signaling domain to obtain chimeric antigen receptor (CAR) constructs. The NKG2D-CAR constructs were then cloned into a retrovirus vector using Gibson assembly and transfected into expi293 cells for retrovirus production. EL4 cells were infected with viruses containing NKG2D-CAR together with 8 μg/mL polybrene. 24 hours after infection, the expression levels of NKG2D-CAR in the EL4 cells were analyzed by flow cytometry, and clones which express high levels of the NKG2D-CAR on the cell surface were selected.

Figure 11:
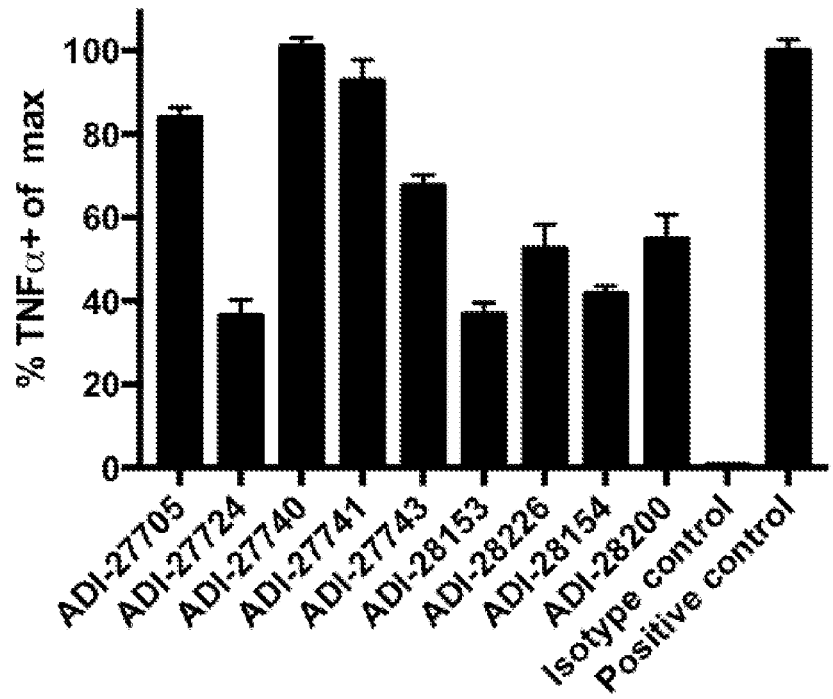
FIG. 11 are bar graphs showing activation of human NKG2D by NKG2D-binding domains (listed as clones) by quantifying the percentage of TNFα-positive cells, which express human NKG2D-CD3 zeta fusion proteins.
Figure 12:
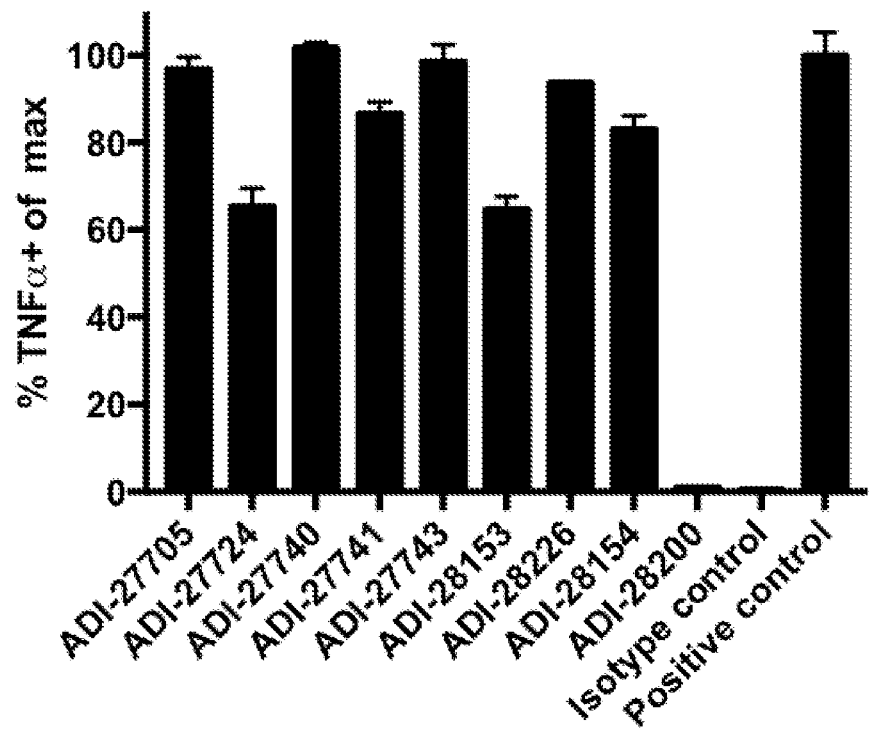
FIG. 12 are bar graphs showing activation of mouse NKG2D by NKG2D-binding domains (listed as clones) by quantifying the percentage of TNFα-positive cells, which express mouse NKG2D-CD3 zeta fusion proteins.

To determine whether NKG2D-binding domains activate NKG2D, they were adsorbed to wells of a microplate, and NKG2D-CAR EL4 cells were cultured on the antibody fragment-coated wells for 4 hours in the presence of brefeldin-A and monensin. Intracellular TNFα production, an indicator for NKG2D activation, was assayed by flow cytometry. The percentage of TNFα-positive cells was normalized to the cells treated with the positive control. All NKG2D-binding domains activated both human NKG2D (FIG. 11) and mouse NKG2D (FIG. 12).

Example 4—NKG2D-Binding Domains Activate NK Cells

Primary Human NK Cells

Figure 13:
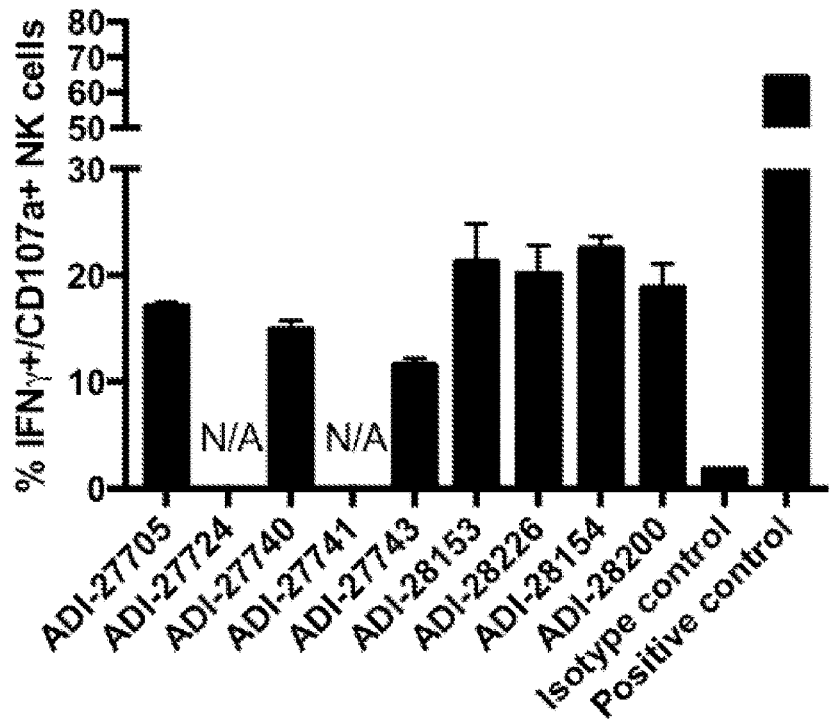
FIG. 13 are bar graphs showing activation of human NK cells by NKG2D-binding domains (listed as clones).
Figure 14:
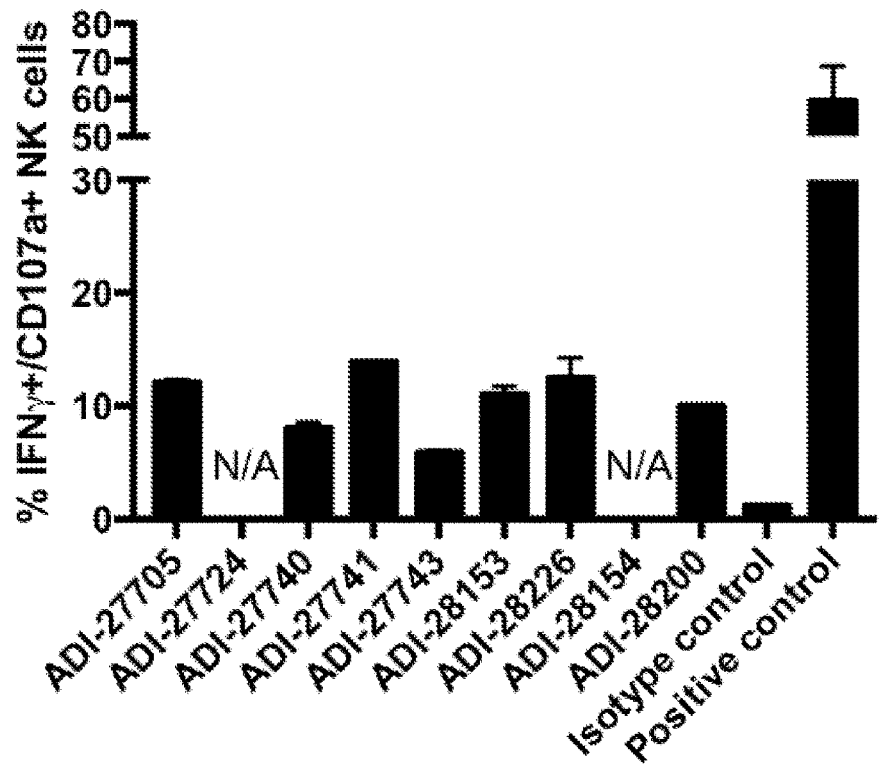
FIG. 14 are bar graphs showing activation of human NK cells by NKG2D-binding domains (listed as clones).

Peripheral blood mononuclear cells (PBMCs) were isolated from human peripheral blood buffy coats using density gradient centrifugation. NK cells (CD3$^-$ CD56$^+$) were isolated using negative selection with magnetic beads from PBMCs, and the purity of the isolated NK cells was typically >95%. Isolated NK cells were then cultured in media containing 100 ng/mL IL-2 for 24-48 hours before they were transferred to the wells of a microplate to which the NKG2D-binding domains were adsorbed, and cultured in the media containing fluorophore-conjugated anti-CD107a antibody, brefeldin-A, and monensin. Following culture, NK cells were assayed by flow cytometry using fluorophore-conjugated antibodies against CD3, CD56 and IFN-γ. CD107a and IFN-γ staining were analyzed in CD3$^-$ CD56$^+$ cells to assess NK cell activation. The increase in CD107a/IFN-γ double-positive cells is indicative of better NK cell activation through engagement of two activating receptors rather than one receptor. NKG2D-binding domains and the positive control (selected from SEQ ID NOs:45-48) showed a higher percentage of NK cells becoming CD107a$^+$ and IFN-γ$^+$ than the isotype control (FIG. 13 & FIG. 14 represent data from two independent experiments, each using a different donor's PBMC for NK cell preparation).

Primary Mouse NK Cells

Figure 15:
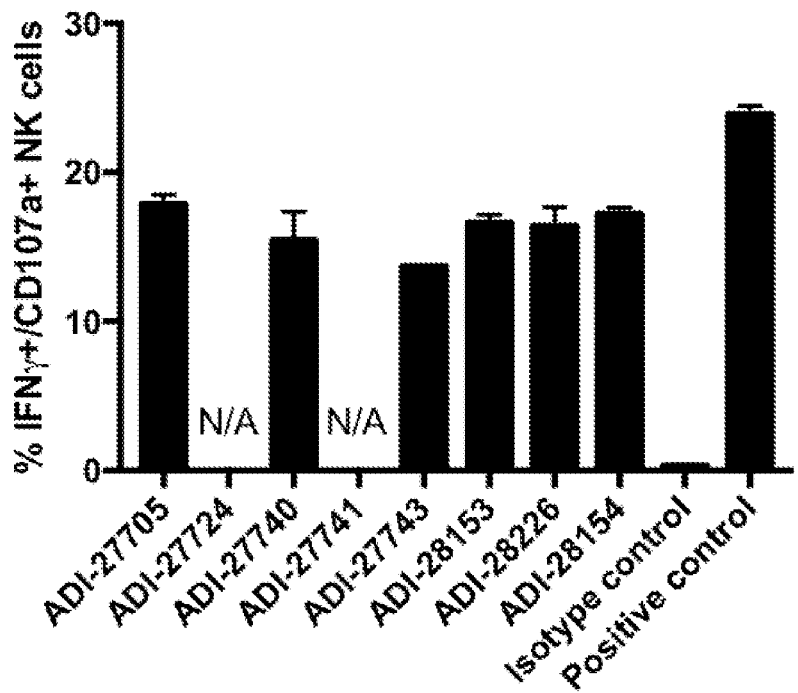
FIG. 15 are bar graphs showing activation of mouse NK cells by NKG2D-binding domains (listed as clones).
Figure 16:
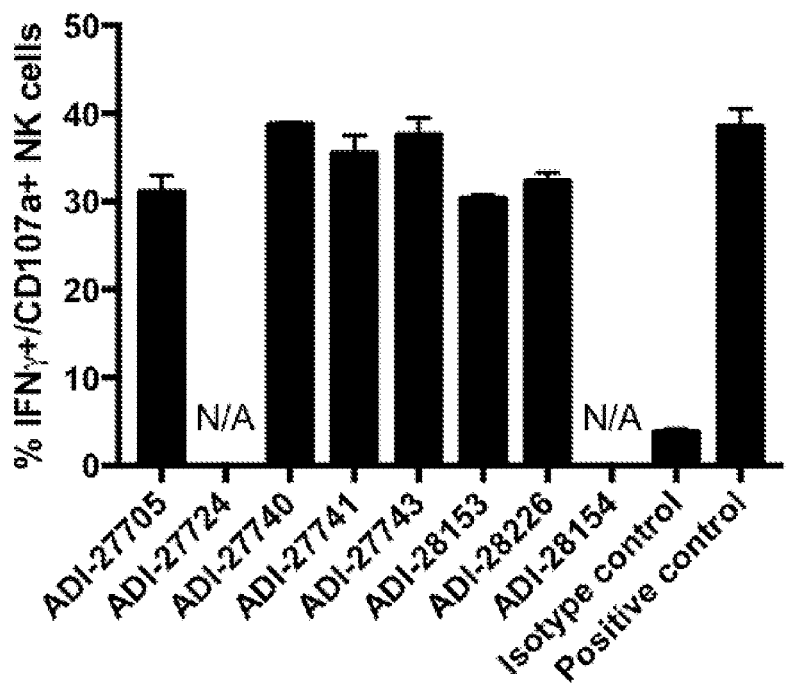
FIG. 16 are bar graphs showing activation of mouse NK cells by NKG2D-binding domains (listed as clones).

Spleens were obtained from C57Bl/6 mice and crushed through a 70 am cell strainer to obtain single cell suspension. Cells were pelleted and resuspended in ACK lysis buffer (purchased from Thermo Fisher Scientific #A1049201; 155 mM ammonium chloride, 10 mM potassium bicarbonate, 0.01 mM EDTA) to remove red blood cells. The remaining cells were cultured with 100 ng/mL hIL-2 for 72 hours before being harvested and prepared for NK cell isolation. NK cells (CD3$^-$NK1.1$^+$) were then isolated from spleen cells using a negative depletion technique with magnetic beads with typically >90% purity. Purified NK cells were cultured in media containing 100 ng/mL mIL-15 for 48 hours before they were transferred to the wells of a microplate to which the NKG2D-binding domains were adsorbed, and cultured in the media containing fluorophore-conjugated anti-CD107a antibody, brefeldin-A, and monensin. Following culture in NKG2D-binding domain-coated wells, NK cells were assayed by flow cytometry using fluorophore-conjugated antibodies against CD3, NK1.1 and IFN-γ. CD107a and IFN-γ staining were analyzed in CD3$^-$ NK1.1$^+$ cells to assess NK cell activation. The increase in CD107a/IFN-γ double-positive cells is indicative of better NK cell activation through engagement of two activating receptors rather than one receptor. NKG2D-binding domains and the positive control (selected from anti-mouse NKG2D clones MI-6 and CX-5 available at eBioscience) showed a higher percentage of NK cells becoming CD107a$^+$ and IFN-γ$^+$ than the isotype control (FIG. 15 & FIG. 16 represent data from two independent experiments, each using a different mouse for NK cell preparation).

Example 5—NKG2D-Binding Domains Enable Cytotoxicity of Target Tumor Cells

Human and mouse primary NK cell activation assays demonstrate increased cytotoxicity markers on NK cells after incubation with NKG2D-binding domains. To address whether this translates into increased tumor cell lysis, a cell-based assay was utilized where each NKG2D-binding domain was developed into a monospecific antibody. The Fc region was used as one targeting arm, while the Fab region (NKG2D-binding domain) acted as another targeting arm to activate NK cells. THP-1 cells, which are of human origin and express high levels of Fc receptors, were used as a tumor target and a Perkin Elmer DELFIA Cytotoxicity Kit was used. THP-1 cells were labeled with BATDA reagent, and resuspended at 10$^5$/mL in culture media. Labeled THP-1 cells were then combined with NKG2D antibodies and isolated mouse NK cells in wells of a microtiter plate at 37° C. for 3 hours. After incubation, 20 μl of the culture supernatant was removed, mixed with 200 μl of Europium solution and incubated with shaking for 15 minutes in the dark. Fluorescence was measured over time by a PheraStar plate reader equipped with a time-resolved fluorescence module (Excitation 337 nm, Emission 620 nm) and specific lysis was calculated according to the kit instructions.

Figure 17:
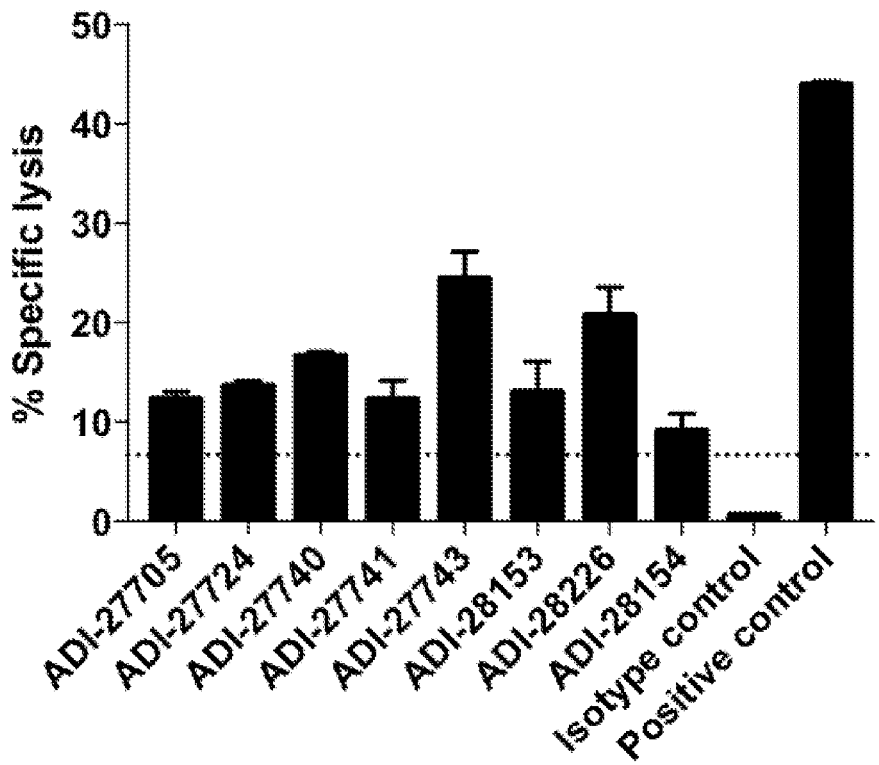
FIG. 17 are bar graphs showing the cytotoxic effect of NKG2D-binding domains (listed as clones) on tumor cells.

The positive control, ULBP-6—a natural ligand for NKG2D, showed increased specific lysis of THP-1 target cells by mouse NK cells. NKG2D antibodies also increased specific lysis of THP-1 target cells, while isotype control antibody showed reduced specific lysis. The dotted line indicates specific lysis of THP-1 cells by mouse NK cells without antibody added (FIG. 17).

Example 6—NKG2D Antibodies Show High Thermostability

Figure 18:
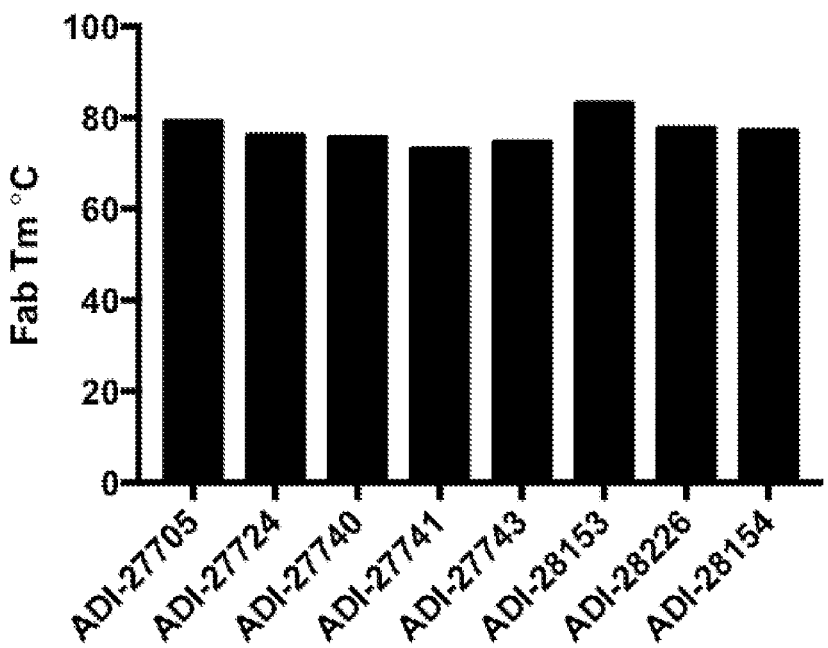
FIG. 18 are bar graphs showing the melting temperature of NKG2D-binding domains (listed as clones) measured by differential scanning fluorimetry.

Melting temperatures of NKG2D-binding domains were assayed using differential scanning fluorimetry. The extrapolated apparent melting temperatures are high relative to typical IgG1 antibodies (FIG. 18).

Example 7—Multi-Specific Binding Proteins Display Enhanced Ability to Activate NK Cells Peripheral blood mononuclear cells (PBMCs) were isolated from human peripheral blood buffy coats using density gradient centrifugation. NK cells (CD3$^-$ CD56$^+$) were isolated using negative selection with magnetic beads from PBMCs, and the purity of the isolated NK cells was typically >95%. Isolated NK cells were then cultured in media containing 100 ng/mL IL-2 for 24-48 hours before they were transferred to the wells of a microplate to which multi-specific and bispecific binding proteins were adsorbed respectively, and cultured in the media containing fluorophore-conjugated anti-CD107a antibody, brefeldin-A, and monensin. Following culture, NK cells were assayed by flow cytometry using fluorophore-conjugated antibodies against CD3, CD56 and IFN-γ. CD107a and IFN-γ staining were analyzed in CD3$^-$ CD56$^+$ cells to assess NK cell activation. The increase in CD107a/IFN-γ double-positive cells is indicative of better NK cell activation. AL2.2 is a multi-specific binding protein containing HER2-binding domain (trastuzumab), NKG2D-binding domain (ULBP-6) and a human IgG1 Fc domain. It was made through a controlled Fab-arm exchange reaction (cFAE) starting from trastuzumab homodimer and ULBP-6-Fc homodimer (see Labrijn et al., Nature Protocols 9, 2450-2463). SC2.2 is single chain protein including an scFv derived from trastuzumab, and ULBP-6 (SEQ ID NO:93).

SEQ ID NO: 93
MAAAAIPALLLCLPLLFLLFGWSRARRDDPHSLCYDITVIPKFRPGP

RWCAVQGQVDEKTFLHYDCGNKTVTPVSPLGKKLNVTMAWKAQNPVL

REVVDILTEQLLDIQLENYTPKEPLTLQARMSCEQKAEGHSSGSWQF

SIDGQTFLLFDSEKRMWTTVHPGARKMKEKWENDKDVAMSFHYISMG

DCIGWLEDFLMGMDSTLEPSAGAPLAMSSGTTQLRATATTLILCCLL

IILPCFILPGI

Figure 19:
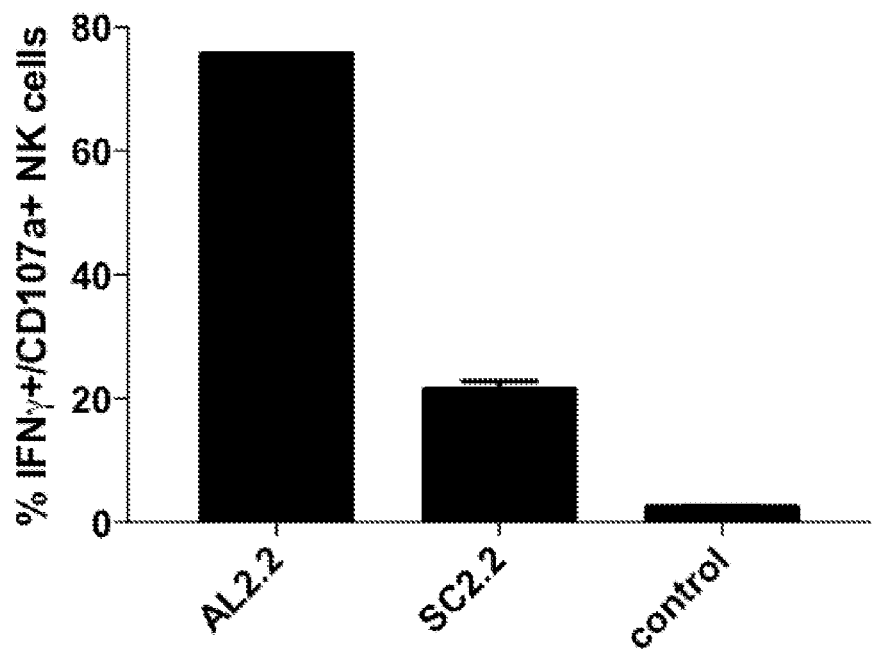
FIG. 19 is a graph showing enhanced activation of human NK cells by multi-specific binding proteins.

Analysis of CD107a and IFN-γ staining indicated that isotype control IgG showed no activation of NK cells, while a higher percentage of NK cells becoming CD107a$^+$ and IFN-γ$^+$ after stimulation with a multi-specific binding protein compared with a bispecific protein, demonstrating stronger NK cell activation through engagement of two activating receptors (NKG2D and CD16) rather than just one (NKG2D) (FIG. 19). This increase in NK cell activation is expected to translate into more potent tumor cell killing.

Example 8—Multi-Specific Binding Proteins Display Enhanced Cytotoxicity Towards Target Tumor Cells Primary Human NK Cell Cytotoxicity Assay Peripheral blood mononuclear cells (PBMCs) were isolated from human peripheral blood buffy coats using density gradient centrifugation. NK cells (CD3$^-$ CD56$^+$) were isolated using negative selection with magnetic beads from PBMCs, and the purity of the isolated NK cells was typically >95%. NK cells were then cultured overnight in media containing 100 ng/mL IL-2 before used in cytotoxicity assays. The following day NK cells were resuspended at $5 \times 10^5$/mL in fresh culture media. Human breast cancer cell SkBr-3 cells were labeled with BATDA reagent according to Perkin Elmer DELFIA Cytotoxicity Kit and resuspended at $5 \times 10^4$/mL in culture media. Various dilution of the multi-specific binding proteins were made into culture media. NK cells, the labeled SkBr-3 cells and the multi-specific binding proteins were then combined in wells of a microtiter plate and incubated at 37° C. for 3 hours. After incubation, 20 µl of the culture supernatant was removed, mixed with 200 µl of Europium solution and incubated with shaking for 15 minutes in the dark. Fluorescence was measured over time by a PheraStar plate reader equipped with a time-resolved fluorescence module (Excitation 337 nm, Emission 620 nm) and specific lysis was calculated according to the kit instructions. AL0.2 is a multi-specific binding protein containing HER2-binding domain (trastuzumab), NKG2D-binding domain (selected from SEQ ID NO: 1-44)) and a human IgG1 Fc domain. It was made through a controlled Fab-arm exchange reaction (cFAE) starting from trastuzumab homodimer and anti-NKG2D homodimer. AL0.2si is based on AL0.2 and contains an additional D265A mutation in Fc domain which abrogates CD16 binding. Trastuzumab-si is based on Trastuzumab and contains an additional D265A mutation in Fc domain which abrogates CD16 binding. AL2.2 is a multi-specific binding protein containing HER2-binding domain (trastuzumab), NKG2D-binding domain (ULBP-6) and a human IgG1 Fc domain. SC2.2 is single chain protein including an scFv derived from trastuzumab, and ULBP-6.

Figure 20:
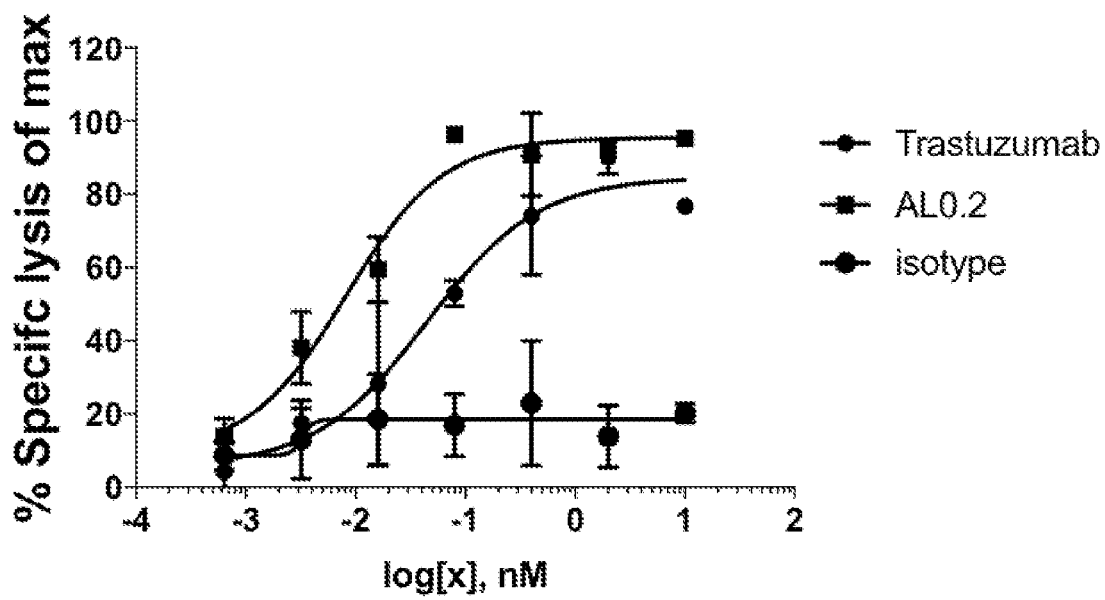
FIG. 20 is a graph showing multi-specific binding proteins induced higher levels of cytotoxicity towards tumor target cells by human NK cells.
Figure 21:
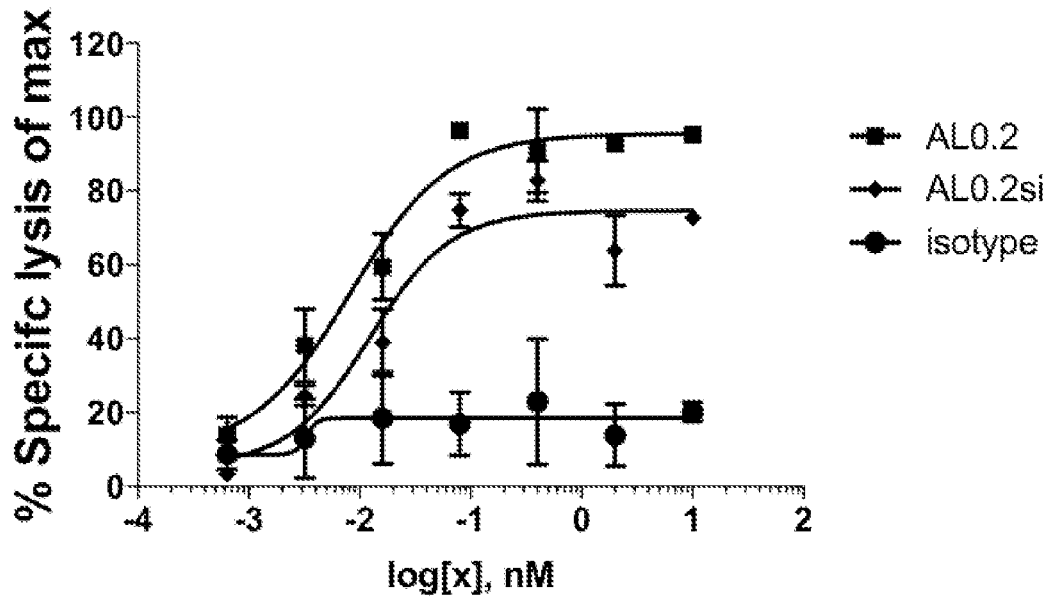
FIG. 21 is a graph showing multi-specific binding proteins induced higher levels of cytotoxicity towards tumor target cells by human NK cells.
Figure 22:
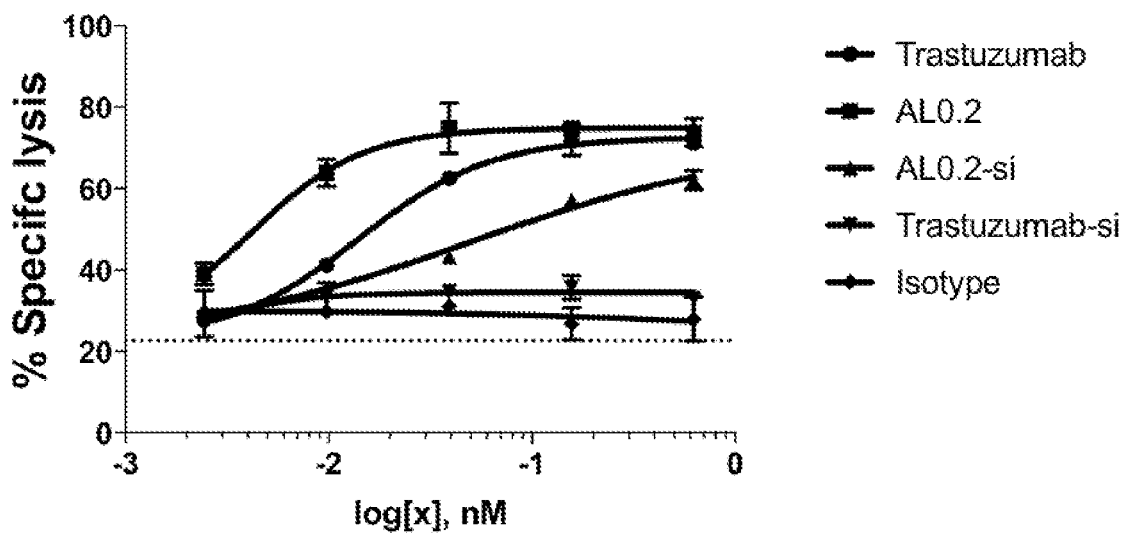
FIG. 22 is a graph showing multi-specific binding proteins induced higher levels of cytotoxicity towards tumor target cells by human NK cells.
Figure 23:
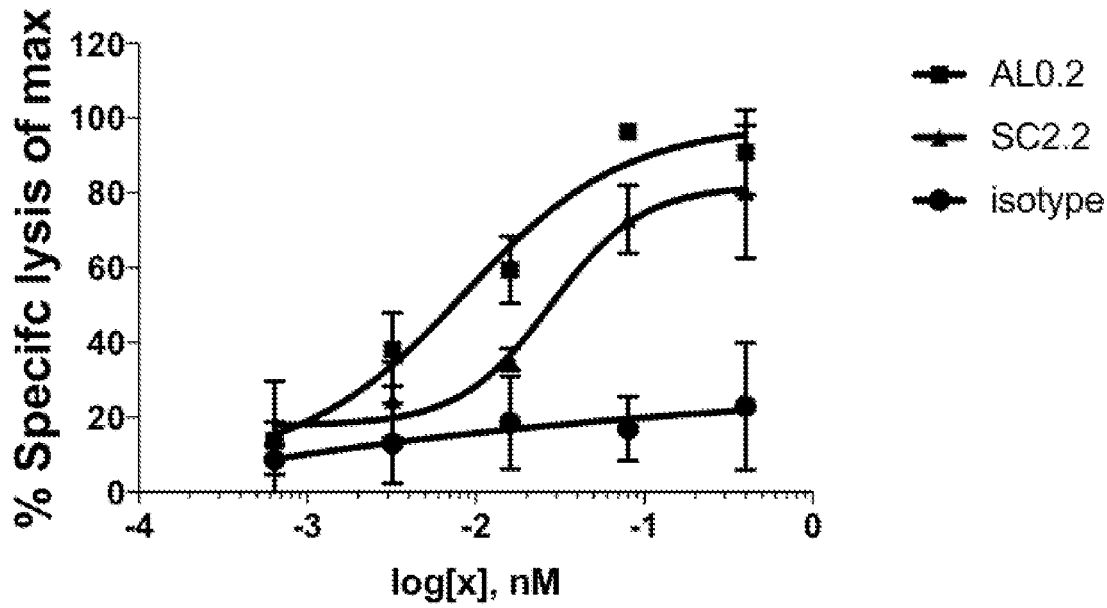
FIG. 23 is a graph showing multi-specific binding proteins induced higher levels of cytotoxicity towards tumor target cells by human NK cells.

AL0.2 showed enhanced lysis of SkBr-3 target cells by human NK cells than trastuzumab in a does dependent manner, with a p value of 0.0311 in EC50 (FIG. 20). AL0.2si (FIG. 21) and trastuzumab-si (FIG. 22) showed reduction in both potency and maximum specific lysis of SkBr-3 cells compared to AL0.2, with a p-value of 0.0002, and 0.0001 in EC50, respectively (FIGS. 21-22). In addition, AL0.2 showed enhanced lysis of SkBr-3 cells than AL2.2 in a dose-dependent manner (FIG. 23). Isotype control IgG showed no increase in specific lysis at any of the concentrations tested. Together the data have demonstrated that multi-specific binding proteins engaging 2 activating receptors on NK cells and one tumor antigen, induce more potent killing of tumor cells by human NK cells compared to bispecific proteins engaging one activating receptor on NK cells and one tumor antigen.

Primary Mouse NK Cell Cytotoxicity Assay

Spleens were obtained from C57Bl/6 mice and crushed through a 70 µm cell strainer to obtain single cell suspension. Cells were pelleted and resuspended in ACK lysis buffer (purchased from Thermo Fisher Scientific #A1049201; 155 mM ammonium chloride, 10 mM potassium bicarbonate, 0.01 mM EDTA) to remove red blood cells. The remaining cells were cultured with 100 ng/mL hIL-2 for 72 hours before being harvested and prepared for NK cell isolation. NK cells (CD3$^-$NK1.1$^+$) were then isolated from spleen cells using a negative depletion technique with magnetic beads with typically >90% purity. Purified NK cells were cultured in media containing 100 ng/mL mIL-15 for 48 hours before resuspended in culture media at $10^6$/mL for cytotoxic assays. RMA-HER2-dTomato, a mouse tumor cell line engineered to express HER2 and dTomato, and its control counterpart, RMA cells expressing zsGreen were used as targets. They were resuspended at $2 \times 10^5$/mL in culture media and seeded into wells of a micro plate at 1:1 ratio. Dilutions of multi-specific protein were made into culture media, and added to the RMA cells together with the NK cells. After incubation overnight at 37° C. with 5% $CO_2$, the percentage of RMA-HER2-dTomato and RMA-zsGreen cells were determined by flow cytometry using the fluorescent reporter to identify the two cells types. Specific target cell death=(1−((% RMA-Ca2T-dTomato cells in treatment group*% RMA-zsGreen cells in control group)/(% RMA-Ca2T-dTomato cells in control group*% RMA-zsGreen cells in treatment group)))*100%.

Figure 24:
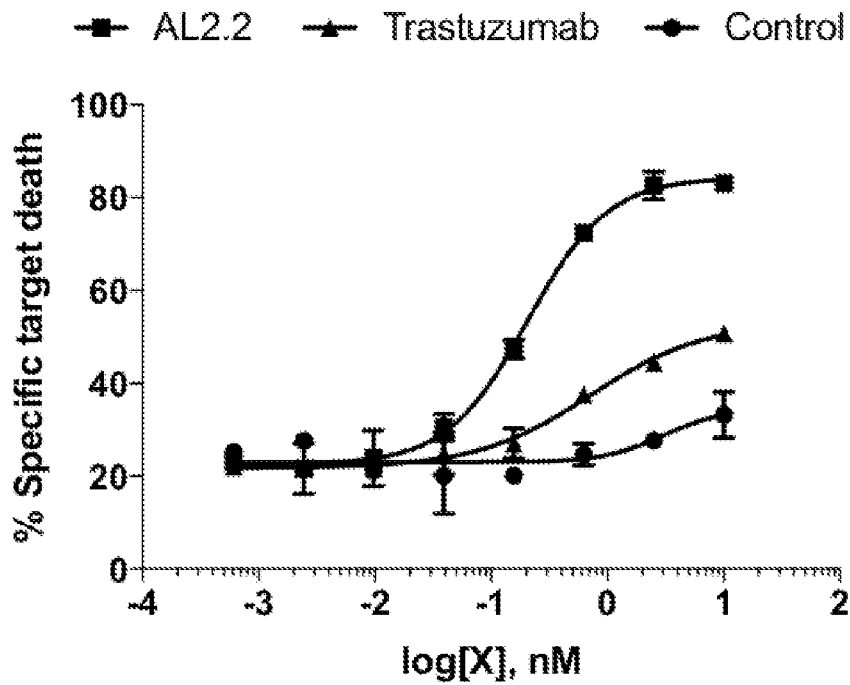
FIG. 24 is a graph showing multi-specific binding proteins induced higher levels of cytotoxicity towards tumor target cells by mouse NK cells.
Figure 25:
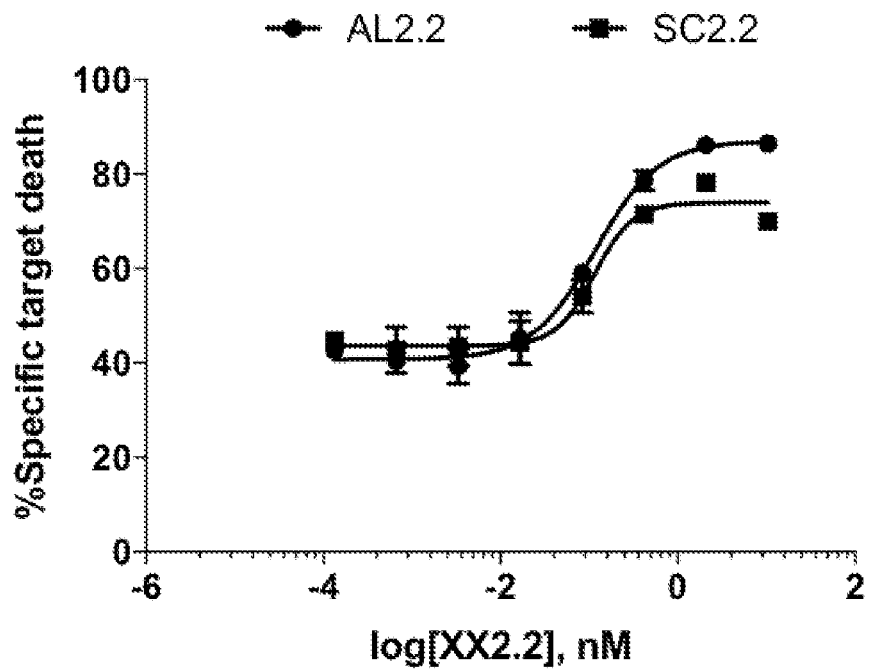
FIG. 25 is a graph showing multi-specific binding proteins induced higher levels of cytotoxicity towards tumor target cells by mouse NK cells.

AL2.2 is more potent in redirecting NK cell responses to tumor targets than SC2.2 (FIG. 25) and Trastuzumab (FIG. 24). Control protein showed little impact on specific target death. These data demonstrate the multi-specific binding proteins engaging 2 activating receptors on NK cells and one tumor antigen, induce more potent killing of tumor cells by mouse NK cells compared to bispecific proteins engaging one activating receptor on NK cells and one tumor antigen.

Example 9—Multi-Specific Binding Proteins Bind to NKG2D

EL4 mouse lymphoma cell lines were engineered to express human NKG2D trispecific binding proteins (TriNKETs) that each contain an NKG2D-binding domain, a HER2-binding domain, and an Fc domain that binds to CD16 as shown in FIG. 1, were tested for their affinity to extracellular NKG2D expressed on EL4 cells. The binding of the multi-specific binding proteins to NKG2D was detected using fluorophore-conjugated anti-human IgG secondary antibodies. Cells were analyzed by flow cytometry, and fold-over-background (FOB) was calculated using the mean fluorescence intensity (MFI) of NKG2D-expressing cells compared to parental EL4 cells.

TriNKETs tested include HER2-TriNKET-C26 (ADI-28226 and a HER2-binding domain), and HER2-TriNKET-F04 (ADI-29404 and a HER2-binding domain). The HER2-binding domain used in the tested molecules was composed of a heavy chain variable domain and a light chain variable domain of Trastuzumab.

Figure 26:
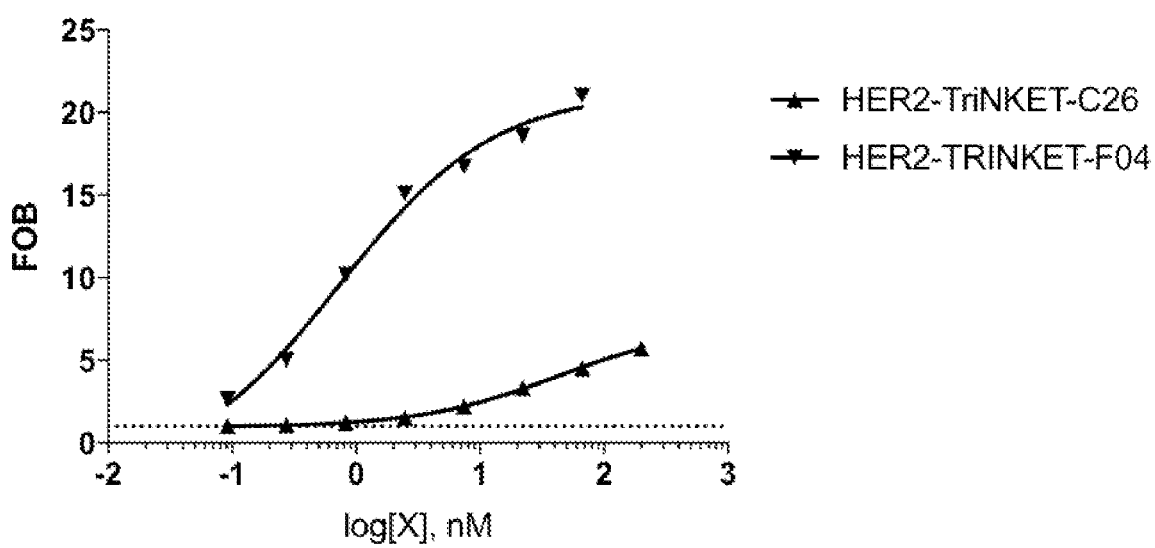
FIG. 26 is a binding profile of HER2-targeting TriNKETs to NKG2D expressed on EL4 cells.

The data show that a HER2 targeting TriNKETs of the present disclosure bind to NKG2D (FIG. 26).

Example 10—Multi-Specific Binding Proteins Bind to Human Tumor Antigen

Trispecific-Binding Proteins Bind to HER2

Figure 27A:
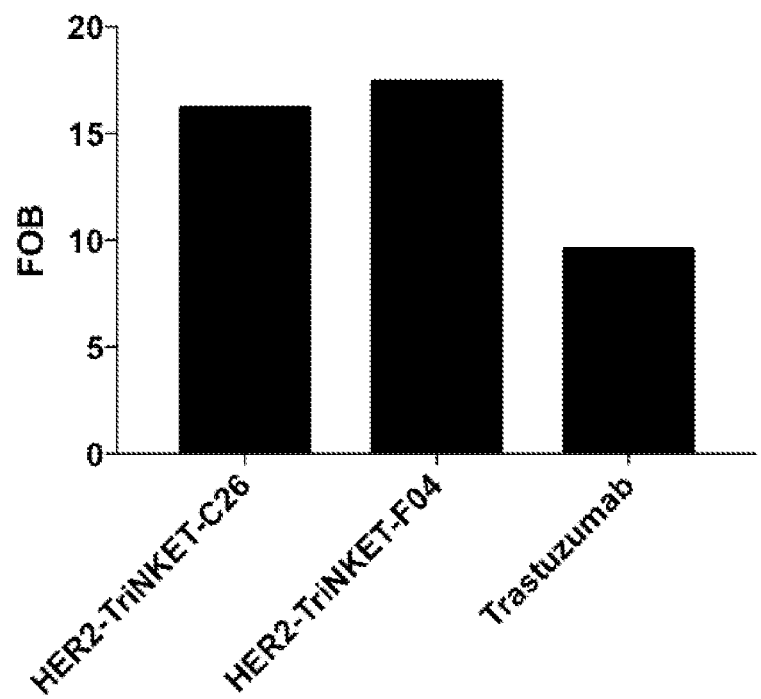
FIG. 27A is a binding profile of HER2-targeting TriNKETs to HER2 expressed on human 786-0 renal cell carcinoma cells.

Human cancer cell lines expressing HER2 were used to assay the binding of HER2 targeting TriNKETs to the tumor associated antigen. Renal cell carcinoma cell line 786-0 expresses low levels of HER2. TriNKETs and optionally the parental anti-HER2 monoclonal antibody (Trastuzumab) were incubated with the cells, and the binding was detected using fluorophore-conjugated anti-human IgG secondary antibodies. Cells were analyzed by flow cytometry, and fold-over-background (FOB) was calculated using the mean fluorescence intensity (MFI) from TriNKETs and Trastuzumab normalized to secondary antibody controls. HER2-TriNKET-C26, and HER2-TriNKET-F04 show comparable levels of binding to HER2 expressed on 786-0 cells as compared with Trastuzumab (FIG. 27A).

Figure 27B:
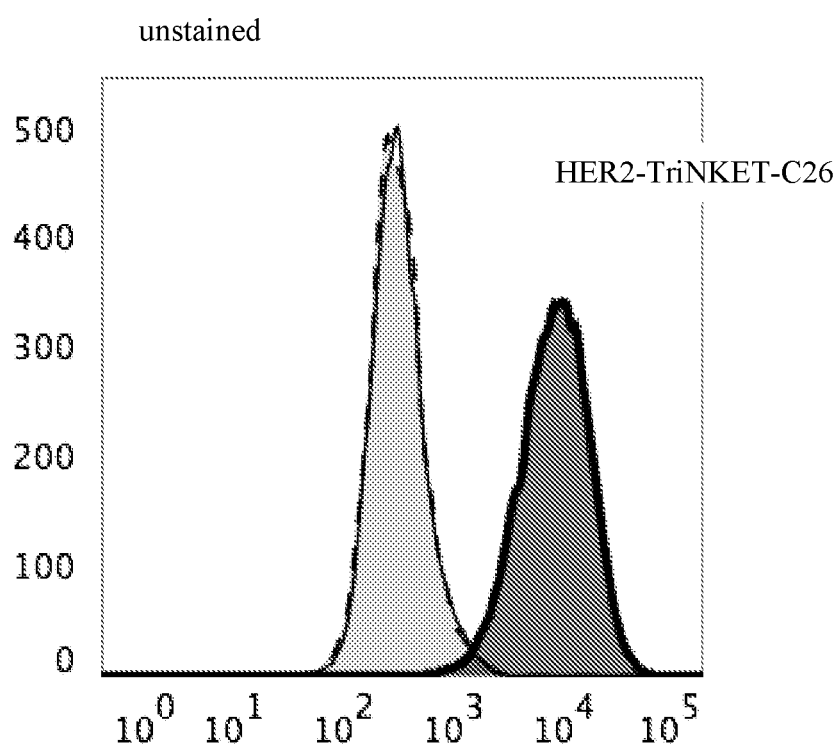
FIG. 27B shows that NKG2D binding clone C26 containing TriNKET binds to RMA cells transduced with human HER2.
Figure 27C:
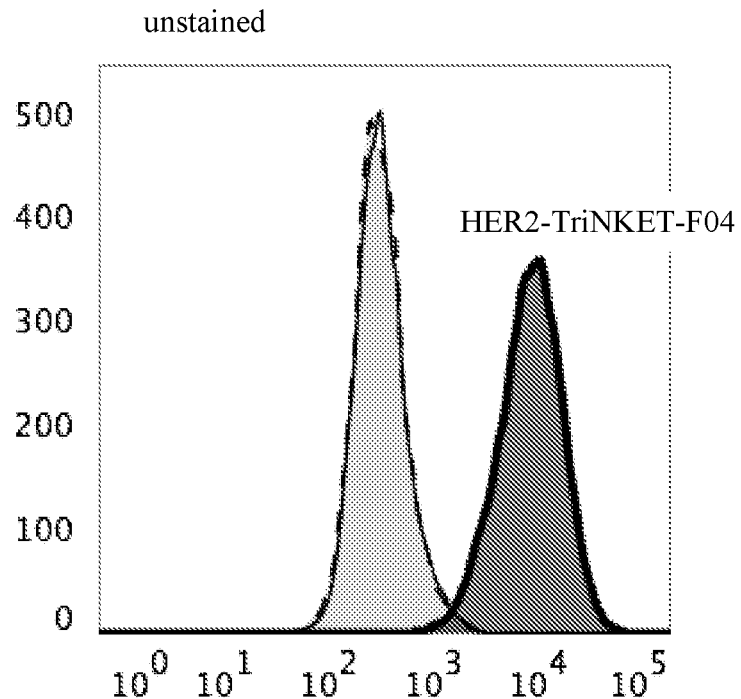
FIG. 27C shows NKG2D binding clone F04 containing TriNKET binds to RMA cells transduced with human HER2.

RMA cells transduced with human HER2 were used to test binding to cell expressed human HER2 by HER2 targeting TriNKETs. TriNKETs were diluted to 20 µg/mL, and binding was detected using a fluorophore conjugated anti-human IgG secondary antibody. Cells were analyzed by flow cytometry, binding to cell expressed HER2 was compared to isotype stained and unstained cell populations. FIG. 27B and FIG. 27C show binding profiles of TriNKETs containing two distinct NKG2D binding domains (the binding profile of C26.2 TriNKET with HER2-binding site shown in FIG. 27B; the binding profile of F04.2 TriNKET with HER2-binding site shown in FIG. 27C), but with the same HER-binding domain. Both TriNKETs show similar level of binding to cell surface HER2 on RMA cells.

Example 11—Multi-Specific Binding Proteins Activate NK Cells

Peripheral blood mononuclear cells (PBMCs) were isolated from human peripheral blood buffy coats using density gradient centrifugation. NK cells (CD3⁻ CD56⁺) were isolated using negative selection with magnetic beads from PBMCs, and the purity of the isolated NK cells was typically >90%. Isolated NK cells were cultured in media containing 100 ng/mL IL-2 for activation or rested overnight without cytokine. IL-2-activated NK cells were used within 24-48 hours after activation.

Human cancer cells expressing a tumor antigen were harvested and resuspended in culture media at $2\times10^6$/mL. Monoclonal antibodies or TriNKETs targeting the tumor antigen were diluted in culture media. Activated NK cells were harvested, washed, and resuspended at $2\times10^6$/mL in culture media. Cancer cells were then mixed with monoclonal antibodies/TriNKETs and activated NK cells in the presence of IL-2. Brefeldin-A and monensin were also added to the mixed culture to block protein transport out of the cell for intracellular cytokine staining. Fluorophore-conjugated anti-CD107a was added to the mixed culture and the culture was incubated for 4 hours before samples were prepared for FACS analysis using fluorophore-conjugated antibodies against CD3, CD56 and IFN-γ. CD107a and IFN-γ staining was analyzed in CD3⁻ CD56⁺ cells to assess NK cell activation. The increase in CD107a/IFN-γ double-positive cells is indicative of better NK cell activation through engagement of two activating receptors rather than one receptor.

TriNKETs mediate activation of human NK cells co-cultured with HER2-expressing SkBr-3 cells (FIG. 28A), Colo201 cells (FIG. 28B), and HCC1954 cells (FIG. 28C) respectively as indicated by an increase of CD107a degranulation and IFN-γ production. SkBr-3 cells and HCC1954 cells have high levels of surface HER2 expression, and Colo201 has medium HER2 expression. Compared to the monoclonal antibody trastuzumab, TriNKETs show superior activation of human NK cells in the presence of human cancer cells. NK cells alone, NK cells plus SkBr-3 cells are used as negative controls.

Figure 28A:
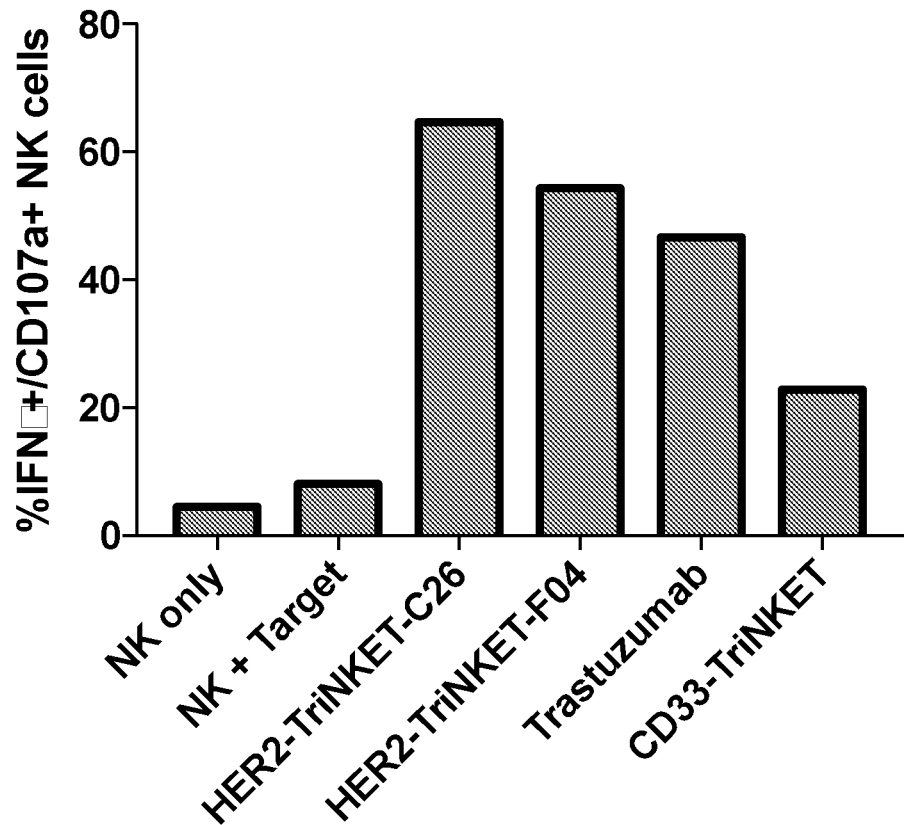
FIGS. 28A-28C are bar graphs demonstrating that TriNKETs and trastuzumab were able to activate primary human NK cells in co-culture with HER2-positive human tumor cells, indicated by an increase in CD107a degranulation and IFNγ cytokine production. Compared to the monoclonal antibody trastuzumab, both TriNKETs showed superior activation of human NK cells with a variety of human HER2 cancer cells.
Figure 28B:
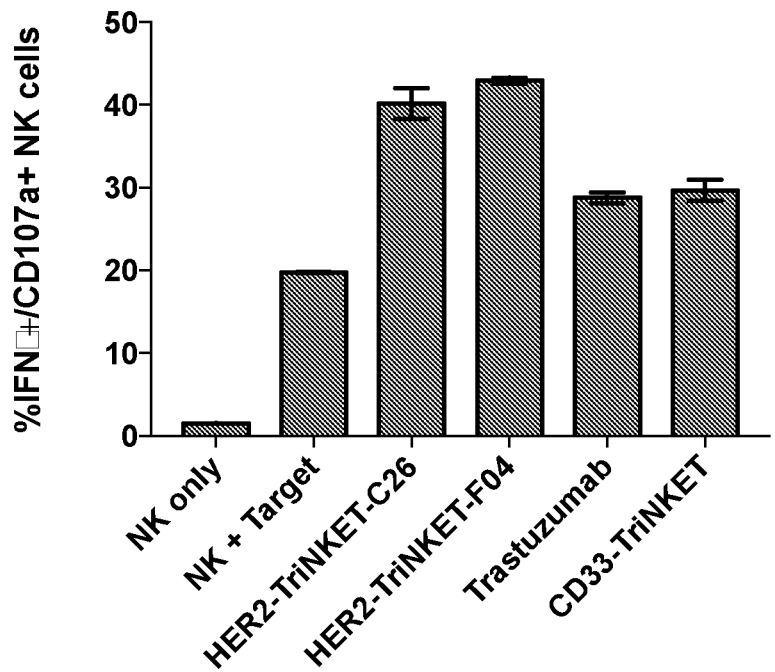
Figure 28C:
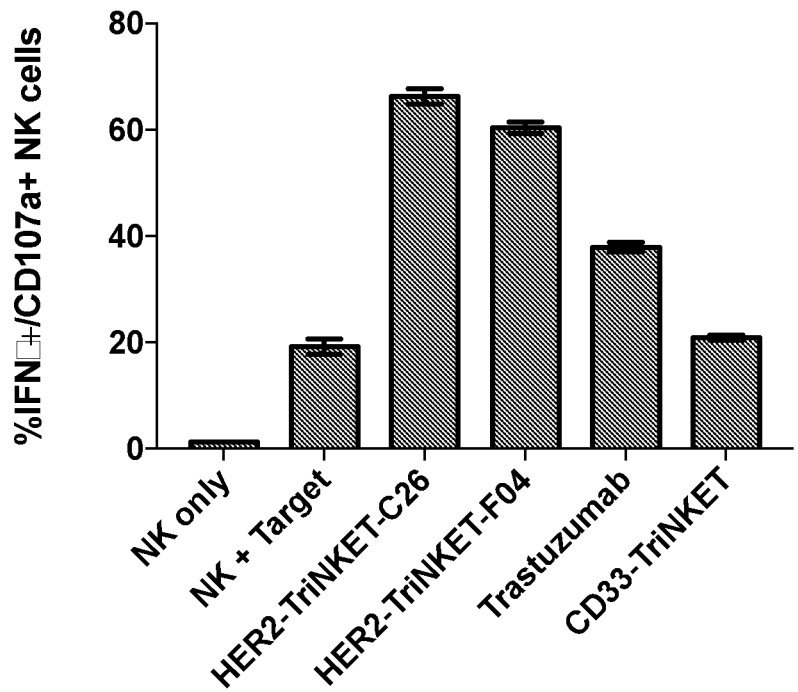

TriNKETs (C26-TriNKET-HER2 and F04-TriNKET-HER2) mediate activation of human NK cells co-cultured with CD33-expressing human AML Mv4-11 cells showed an increase of CD107a degranulation and IFN-γ production. Compared to the monoclonal anti-CD33 antibody, TriNKETs (C26-TriNKET-HER2 and F04-TriNKET-HER2) showed superior activation of human NK cells in the presence of human cancer cells expressing HER2 (FIGS. 28A-28C).

Example 12—Trispecific-Binding Proteins Enable Cytotoxicity of Target Cancer Cells Peripheral blood mononuclear cells (PBMCs) were isolated from human peripheral blood buffy coats using density gradient centrifugation. NK cells (CD3⁻ CD56⁺) were isolated using negative selection with magnetic beads from PBMCs, and the purity of the isolated NK cells was typically >90%. Isolated NK cells were cultured in media containing 100 ng/mL IL-2 for activation or rested overnight without cytokine. IL-2-activated or rested NK cells were used the following day in cytotoxicity assays.

In order to test the ability of human NK cells to lyse cancer cells in the presence of TriNKETs, a cyto Tox 96 non-radioactive cytotoxicity assay from Promega (G1780) was used according to the manufacturer's instructions. Briefly, human cancer cells expressing a tumor antigen were harvested, washed, and resuspended in culture media at $1\text{-}2\times10^5$/mL. Rested and/or activated NK cells were harvested, washed, and resuspended at $10^5\text{-}2.0\times10^6$/mL in the same culture media as that of the cancer cells. In each well of a 96 well plate, 50 µl of the cancer cell suspension was mixed with 50 µl of NK cell suspension with or without TriNKETs targeting the tumor antigen expressed on the cancer cells. After incubation at 37° C. with 5% $CO_2$ for 3 hours and 15 minutes, 10× lysis buffer was added to wells containing only cancer cells, and to wells containing only media for the maximum lysis and negative reagent controls, respectively. The plate was then placed back into the incubator for an additional 45 minutes to reach a total of 4 hours incubation. Cells were then pelleted, and the culture supernatant was transferred to a new 96 well plate and mixed with a substrate for development. The new plate was incubated for 30 minutes at room temperature, and the absorbance was read at 492 nm on a SpectraMax i3x. Percentage of specific lysis of the cancer cells was calculated as follows: % Specific lysis=((experimental lysis−spontaneous lysis from NK cells alone−spontaneous lysis from cancer cells alone)/(Maximum lysis−negative reagent control))×100%.

Figure 29A:
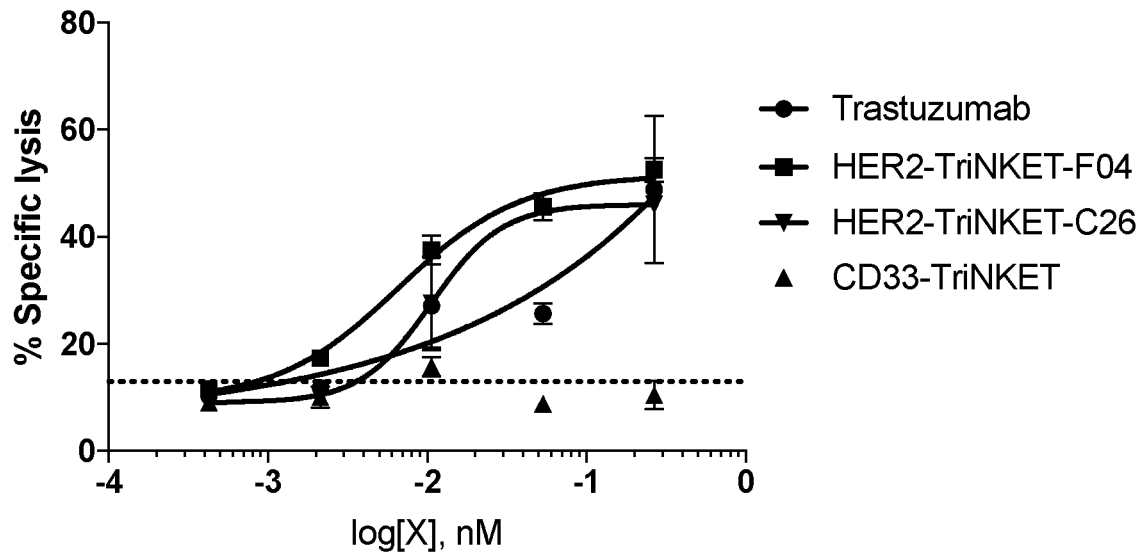
FIGS. 29A-29B are graphs demonstrating TriNKETs provide the greater advantage against HER2 medium and low cancers compared to trastuzumab.
Figure 29B:
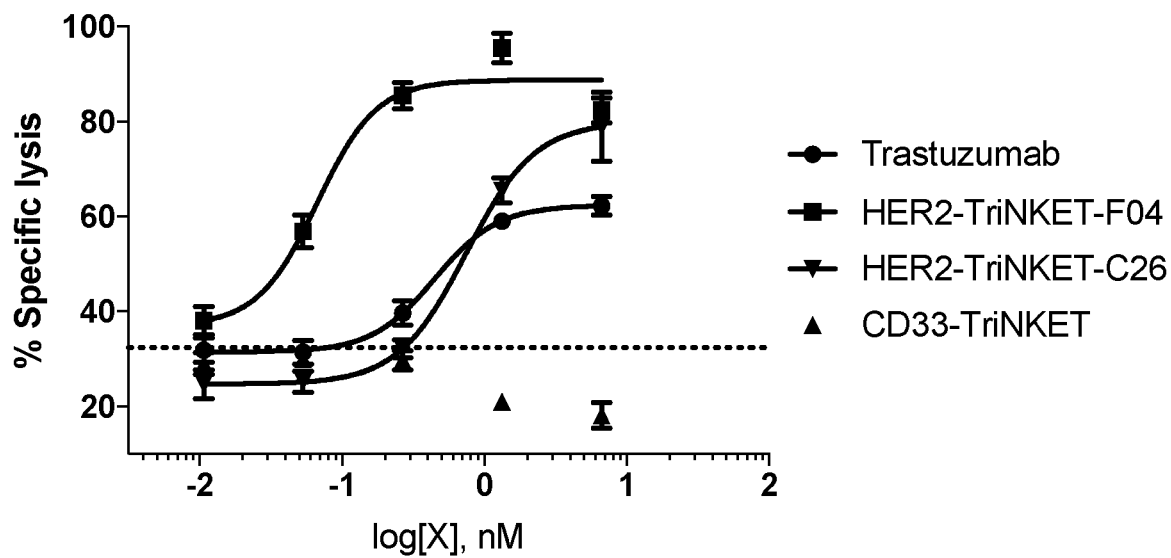

TriNKETs enhance NK cell cytotoxicity against targets with low surface expression compared to the cytotoxic activity of trastuzumab, an anti-HER2 monoclonal antibody. Rested human NK cells were mixed with high HER2-expressing SkBr tumor cells and low HER2-expressing 786-0 cancer cells, and TriNKETs' ability to enhance the cytotoxic activity of rested human NK cells against the high and low HER2-expressing cancer cells in a dose-responsive manner was assayed. Dotted lines in FIG. 29A and FIG. 29B indicate the cytotoxic activity of rested NK cells against the cancer cells in the absence of TriNKETs. As shown in FIG. 29B, upon mixing activated human NK cells with low HER2-expressing 786-0 cells and TriNKET (e.g., CD26-TriNKET and F04-TriNKET, which includes a binding domain for HER2), dose-responsive cytotoxic activity of activated human NK cells against the cancer cells was observed.

Example 13—Synergistic Activation of Human NK Cells by Cross-Linking NKG2D and CD16

Primary Human NK Cell Activation Assay

Peripheral blood mononuclear cells (PBMCs) were isolated from peripheral human blood buffy coats using density gradient centrifugation. NK cells were purified from PBMCs using negative magnetic beads (StemCell #17955). NK cells were >90% CD3⁻ CD56⁺ as determined by flow cytometry. Cells were then expanded 48 hours in media containing 100 ng/mL hIL-2 (Peprotech #200-02) before use in activation assays. Antibodies were coated onto a 96-well flat-bottom plate at a concentration of 2 µg/ml (anti-CD16, Biolegend #302013) and 5 jag/mL (anti-NKG2D, R&D #MAB139) in 100 µl sterile PBS overnight at 4° C. followed by washing the wells thoroughly to remove excess antibody. For the assessment of degranulation IL-2-activated NK cells were resuspended at $5\times10^5$ cells/ml in culture media supplemented with 100 ng/mL hIL2 and 1 µg/mL APC-conjugated anti-CD107a mAb (Biolegend #328619). $1\times10^5$ cells/well were then added onto antibody coated plates. The protein transport inhibitors Brefeldin A (BFA, Biolegend #420601) and Monensin (Biolegend #420701) were added at a final dilution of 1:1000 and 1:270 respectively. Plated cells were incubated for 4 hours at 37° C. in 5% $CO_2$. For intracellular staining of IFN-γ NK cells were labeled with anti-CD3 (Biolegend #300452) and anti-CD56 mAb (Biolegend #318328) and subsequently fixed and permeabilized and labeled with anti-IFN-γ mAb (Biolegend #506507). NK cells were analyzed for expression of CD107a and IFN-γ by flow cytometry after gating on live CD56⁺CD3⁻ cells.

Figure 30C:
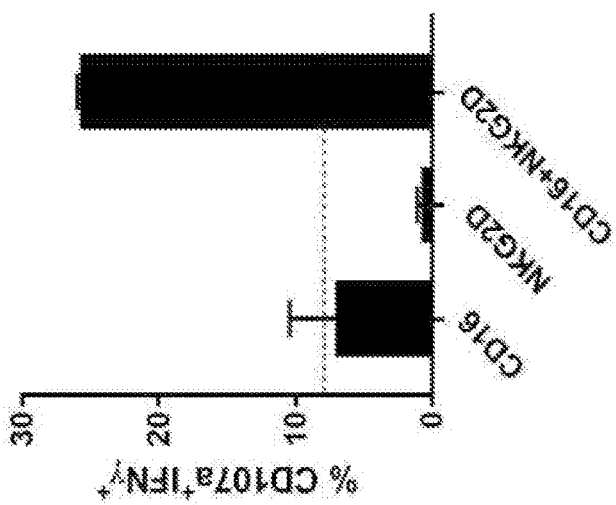
FIGS. 30A-30C are bar graphs of synergistic activation of NK cells using CD16 and NKG2D.
Figure 30B:
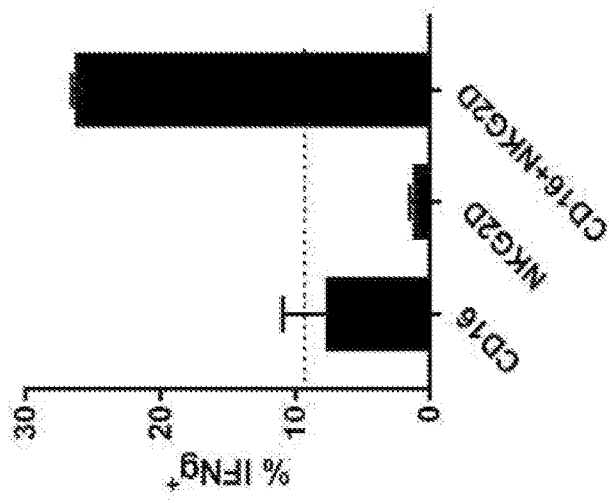
Figure 30A:
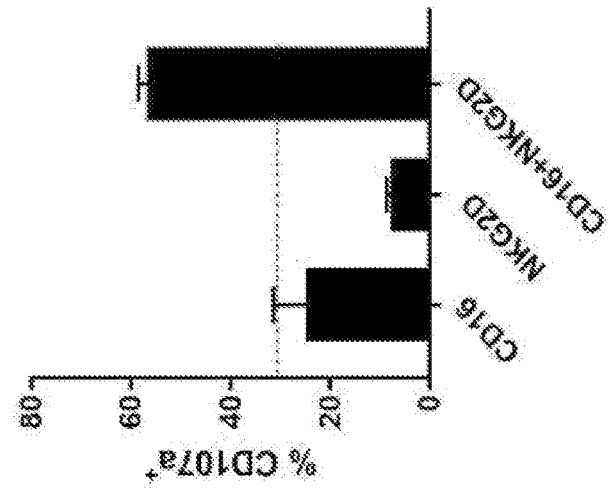

To investigate the relative potency of receptor combination, crosslinking of NKG2D or CD16 and co-crosslinking of both receptors by plate-bound stimulation was performed. As shown in FIG. 30 (FIGS. 30A-30C), combined stimulation of CD16 and NKG2D resulted in highly elevated levels of CD107a (degranulation) (FIG. 30A) and/or IFN-γ production (FIG. 30B). Dotted lines represent an additive effect of individual stimulations of each receptor.

CD107a levels and intracellular IFN-γ production of IL-2-activated NK cells were analyzed after 4 hours of plate-bound stimulation with anti-CD16, anti-NKG2D or a combination of both monoclonal antibodies. Graphs indicate the mean (n=2)±SD. FIG. 19A demonstrates levels of CD107a; FIG. 30B demonstrates levels of IFNγ; FIG. 30C demonstrates levels of CD107a and IFNγ. Data shown in FIGS. 30A-30C are representative of five independent experiments using five different healthy donors.

Figure 31:
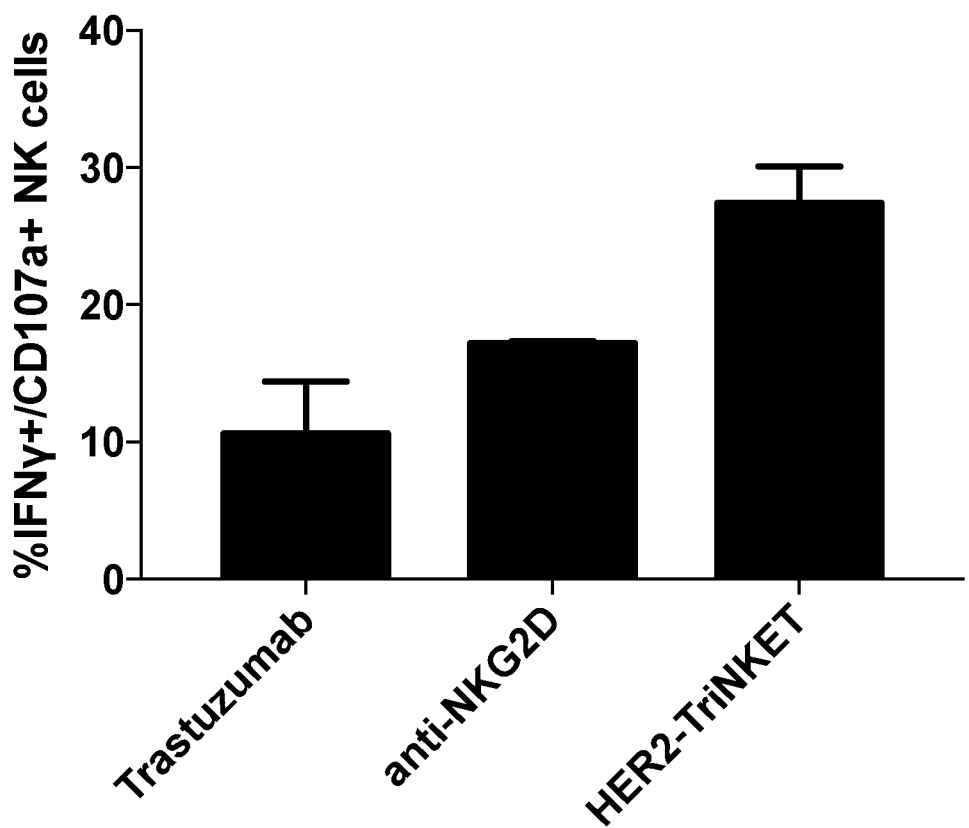
FIG. 31 is a bar graph showing activation of NK cells using TriNKETs targeting NKG2D and CD16. Antibodies tested were of human IgG1 isotypes. Graphs indicate the mean (n=2)±SD.

CD107a degranulation and intracellular IFN-γ production of IL-2-activated NK cells were analyzed after 4 hours of plate-bound stimulation with trastuzumab, anti-NKG2D, or a TriNKET derived from the binding domains of trastuzumab and the anti-NKG2D antibody (FIG. 31). In all cases antibodies tested were of the human IgG1 isotype. Graphs indicate the mean (n=2)±SD.

Example 14—Properties of the TriNKETs

Assessment of TriNKET Binding to Cell-Expressed Human NKG2D

EL4 cells transduced with human NKG2D were used to test binding to cell-expressed human NKG2D. TriNKETs were diluted to 20 µg/mL, and then diluted serially. The mAb or TriNKET dilutions were used to stain cells, and binding of the TriNKET or mAb was detected using a fluorophore-conjugated anti-human IgG secondary antibody. Cells were analyzed by flow cytometry, binding MFI was normalized to secondary antibody controls to obtain fold over background values.

Assessment of TriNKET Binding to Cell-Expressed Human Cancer Antigens

Human cancer cell lines expressing HER2 were used to assess tumor antigen binding of TriNKETs derived from different NKG2D targeting clones. The human renal cell carcinoma cell line 786-0 expresses low levels of HER2 and was used to assess TriNKET binding to cell-expressed HER2. TriNKETs were diluted to 20 µg/mL, and were incubated with the respective cells. Binding of the TriNKET was detected using a fluorophore-conjugated anti-human IgG secondary antibody. Cells were analyzed by flow cytometry, binding MFI to cell expressing HER2 was normalized to secondary antibody controls to obtain fold over background values.

Determination of Antibody Binding Capacity of Human HER2-Positive Cancer Cell Lines Antibody binding capacity (ABC) of HER2-positive human cancer cell lines was measured. The Quantum Simply Cellular kit from Bangs Lab was used (#815), and the manufacturer instructions were followed for the preparation of antibody labeled beads. Briefly, each of the four populations of beads were stained with a saturating amount of anti-HER2 antibody, and the cell populations were also stained with a saturating amount of the same antibody. Sample data was acquired for each bead population, as well as the cell populations. The QuickCal worksheet, provided with the kit, was used for the generation of a standard curve and extrapolation of ABC values for each of the cell lines.

Activation of Primary NK Cells by TriNKETs

PBMCs were isolated from human peripheral blood buffy coats using density gradient centrifugation. Isolated PBMCs were washed and prepared for NK cell isolation. NK cells were isolated using a negative selection technique with magnetic beads; the purity of isolated NK cells was typically >90% CD3−CD56+. Isolated NK cells were cultured in media containing 100 ng/mL IL-2 for activation or rested overnight without cytokine. IL-2-activated NK cells were used 24-48 hours later; rested NK cells were always used the day after purification.

Human cancer cell lines expressing a cancer target of interest were harvested from culture, and cells were adjusted to $2\times10^6$/mL. Monoclonal antibodies or TriNKETs targeting the cancer target of interest were diluted in culture media. Rested and/or activated NK cells were harvested from culture, cells were washed, and were resuspended at $2\times10^6$/mL in culture media. IL-2, and fluorophore-conjugated anti-CD107a were added to the NK cells for the activation culture. Brefeldin-A and monensin were diluted into culture media to block protein transport out of the cell for intracellular cytokine staining. Into a 96-well plate 50 µl of tumor targets, mAbs/TriNKETs, BFA/monensin, and NK cells were added for a total culture volume of 200 µl. The plate was cultured for 4 hours before samples were prepared for FACS analysis.

Following the 4 hour activation culture, cells were prepared for analysis by flow cytometry using fluorophore-conjugated antibodies against CD3, CD56 and IFNγ. CD107a and IFNγ staining was analyzed in CD3−CD56+ populations to assess NK cell activation.

Primary Human NK Cell Cytotoxicity Assay

PBMCs were isolated from human peripheral blood buffy coats using density gradient centrifugation. Isolated PBMCs were washed and prepared for NK cell isolation. NK cells were isolated using a negative selection technique with magnetic beads, purity of isolated NK cells was typically >90% CD3−CD56+. Isolated NK cells were cultured in media containing 100 ng/mL IL-2 or were rested overnight without cytokine. IL-2-activated or rested NK cells were used the following day in cytotoxicity assays.

Cyto Tox 96 LHD Release Assay:

The ability of human NK cells to lyse tumor cells was measured with or without the addition of TriNKETs using the cyto Tox 96 non-radioactive cytotoxicity assay from Promega (G1780). Human cancer cell lines expressing a cancer target of interest were harvested from culture, cells were washed with PBS, and were resuspended in growth media at $1-2\times10^5$/mL for use as target cells. 50 µl of the target cell suspension were added to each well. Monoclonal antibodies or TriNKETs targeting a cancer antigen of interest were diluted in culture media, 50 µl of diluted mAb or TriNKET were added to each well. Rested and/or activated NK cells were harvested from culture, cells were washed, and were resuspended at $10^5-2.0\times10^6$/mL in culture media depending on the desired E:T ratio. 50 µl of NK cells were added to each well of the plate to make a total of 150 µl culture volume. The plate was incubated at 37° C. with 5% $CO_2$ for 3 hours and 15 minutes. After the incubation, 10× lysis buffer was added to wells of target cells alone, and to wells containing media alone, for maximum lysis and volume controls. The plate was then placed back into the incubator for an additional 45 minutes, to make to total of 4 hours of incubation before development.

After incubation, the plate was removed from the incubator and the cells were pelleted by centrifugation at 200 g for 5 minutes. 50 µl of culture supernatant were transferred to a clean microplate and 50 µl of substrate solution were added to each well. The plate was protected from the light and incubated for 30 minutes at room temperature. 50 µl of stop solution were added to each well, and absorbance was read at 492 nm on a SpectraMax i3x. % Specific lysis was calculated as follows: % Specific lysis=((Experimental release−Spontaneous release from effector−Spontaneous release from target)/(Maximum release−Spontaneous release))*100%.

DELFIA Cytotoxicity Assay:

Human cancer cell lines expressing a target of interest were harvested from culture, cells were washed with PBS, and were resuspended in growth media at $10^6$/mL for labeling with BATDA reagent (Perkin Elmer AD0116). Manufacturer instructions were followed for labeling of the target cells. After labeling cells were washed 3× with PBS, and were resuspended at $0.5-1.0\times10^5$/mL in culture media. To prepare the background wells an aliquot of the labeled cells was put aside, and the cells were spun out of the media. 100 µl of the media were carefully added to wells in triplicate to avoid disturbing the pelleted cells. 100 µl of BATDA labeled cells were added to each well of the 96-well plate. Wells were saved for spontaneous release from target cells, and wells were prepared for max lysis of target cells by addition of 1% Triton-X. Monoclonal antibodies or TriNKETs against the tumor target of interest were diluted in culture media and 50 µl of diluted mAb or TriNKET were added to each well. Rested and/or activated NK cells were harvested from culture, cells were washed, and were resuspended at $10^5-2.0\times10^6$/mL in culture media depending on the desired E:T ratio. 50 µl of NK cells were added to each well of the plate to make a total of 200 µl culture volume. The plate was incubated at 37° C. with 5% CO2 for 2-3 hours before developing the assay.

After culturing for 2-3 hours, the plate was removed from the incubator and the cells were pelleted by centrifugation at 200 g for 5 minutes. 20 µl of culture supernatant was transferred to a clean microplate provided from the manufacturer, 200 µl of room temperature europium solution were added to each well. The plate was protected from the light and incubated on a plate shaker at 250 rpm for 15 minutes. Plate was read using either Victor 3 or SpectraMax i3X instruments. % Specific lysis was calculated as follows: % Specific lysis=((Experimental release−Spontaneous release)/(Maximum release−Spontaneous release))*100%.

Long Term Human PBMC Cytotoxicity Assay

SkBr-3 target cells were labeled with BacMam 3.0 NucLight Green (#4622) to allow for tracking of the target cells. The manufacturer's protocol was followed for labeling of SkBr-3 target cells. Annexin V Red (Essen Bioscience #4641) was diluted and prepared according to the manufacturer's instructions. Monoclonal antibodies or TriNKETs were diluted into culture media. 50 µl of mAbs or TriNKETs, Annexin V, and rested NK cells were added to wells of a 96 well plate already containing labeled SkBr-3 cells; 50 µl of complete culture media was added for a total of 200 µl culture volume.

Image collection was setup on the IncuCyte S3. Images for the phase, green, and red channels were collected every hour, with 2 images per well. Image analysis was done using the IncuCyte S3 software. Masks for the green and red channels were created to count the number of tumor cells, and annexin V-positive cells respectively. To calculate the % annexin V-positive Mv4-11 target cells the following formula was used. % Annexin V-positive SkBr-3 cells=((overlap object count)/(green object count))*100%.

Comparing a TriNKET that Targets HER+ Cancer Cells with SC2.2

A TriNKET targeting HER2 is more effective than Trastuzumab at reducing SkBr-3 cell number, and only 60% of the cells from time zero were left after 60 hours. A TriNKET of the present disclosure that targets HER2 expressing tumor/cancer cells is more effective than SC2.2—a single chain bispecific molecule built from an scFv derived from trastuzumab linked to ULBP-6, a ligand for NKG2D. SC2.2 binds HER2+ cancer cells and NKG2D+ NK cells simultaneously. Therefore, effectiveness of SC2.2 in reducing HER2+ cancer cell number was investigated. In vitro activation and cytotoxicity assays demonstrated that SC2.2 was effective in activating and killing NK cells. However, SC2.2 failed to demonstrate efficacy in the RMA/

S-HER2 subcutaneous tumor model. The efficacy of SC2.2 was also tested in vivo using an RMA/S-HER2 overexpressing syngeneic mouse model. In this mouse model, SC2.2 failed to demonstrate control of tumor growth compared to vehicle control. Thus, although SC2.2 was able to activate and kill NK cells, and binds to HER2+ cancer cells, these properties were insufficient to effectively control HER2+ tumor growth.

Assessment of SC2.2 Serum Half-Life in C57Bl/6 Mice

To determine the serum half-life of SC2.2 in C57Bl/6 mice, SC2.2 was labeled with a fluorescent tag to track its concentration in vivo. SC2.2 was labeled with IRDye 800CW (Licor #929-70020). The labeled protein was injected intravenously into 3 C57Bl/6 mice, blood was taken from each mouse at the indicated time points. After collection blood was centrifuged at 1000 g for 15 minutes and serum was collected from each sample and stored at 4 C until all time points were collected.

Serum was imaged using an Odyssey CLx infrared imaging system, the fluorescent signal from the 800 channel was quantified using Image J software. Image intensities were normalized to the first time point, and the data was fit to a biphasic decay equation. In this experimental system the beta half-life of SC2.2 was calculated to be around 7 hours.

In Vivo Testing of SC2.2 Against RMA/S-HER2 Subcutaneous Tumors

An in vivo study was designed according to FIG. 37 to test the efficacy of SC2.2 against subcutaneous RMA/S-HER2 tumors. $10^6$ RMA/S cells transduced with human HER2 were injected subcutaneously into the flank of 20 C57Bl/6 mice. Starting day 2 after tumor inoculation SC2.2 was dosed daily via IP injection. SC2.2 was dosed at a high and a low concentrations along with a vehicle control. Starting day 4 after tumor inoculation tumors were measured Monday, Wednesday, and Friday for the duration of the study. Tumor volume was calculated using the following formula: Tumor volume=Length×width×height.

Antibody Binding Capacity of Human HER2-Positive Cancer Cell Lines

Table 10 shows the results of HER2 surface quantification. SkBr-3 and HCC1954 cells were identified to have high (+++) levels of surface HER2. ZR-75-1 and Colo201 showed medium levels (++) of surface HER2, and 786-0 showed the lowest level of HER2 (+).

TABLE 10

ABC of HER2-positive cancer cell lines

| Cell Line | HER2 expression | ABC |
|---|---|---|
| 786-0 | Low | 28,162 |
| Colo201 | Medium | 273,568 |
| ZR-75-1 | Medium | 281,026 |
| SkBr-3 | High | 6,820,532 |
| HCC1954 | High | 10,569,869 |

Primary Human NK Cells are Activated by TriNKETs in Co-Culture with Human Cancer Lines Expressing Varying Levels of HER2

FIGS. 28A-28C show that TriNKETs and trastuzumab were able to activate primary human NK cells in co-culture with HER2-positive human tumor cells, indicated by an increase in CD107a degranulation and IFNγ cytokine production. Compared to the monoclonal antibody trastuzumab, both TriNKETs (HER2-TriNKET-C26 and HER2-TriNKET-F04) showed superior activation of human NK cells with a variety of human HER2 cancer cells.

FIG. 28A shows that human NK cells are activated by TriNKETs when cultured with SkBr-3 cells. FIG. 28B shows that human NK cells are activated by TriNKETs when cultured with Colo201 cells. FIG. 28C shows that human NK cell are activated by TriNKETs when cultured with HCC1954 cells.

TriNKETs Enhance Cytotoxicity of Rested and IL-2-Activated Human NK Cells

Figure 32A:
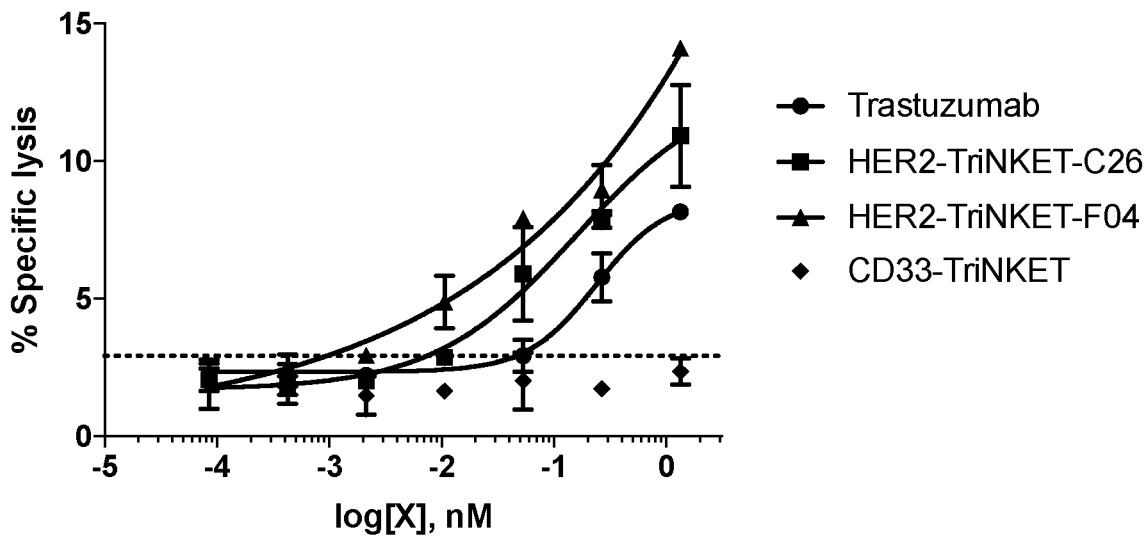
FIGS. 32A-32C are graphs demonstrating TriNKET enhancement of cytotoxic activity using IL-2-activated and rested human NK cells.
Figure 32B:
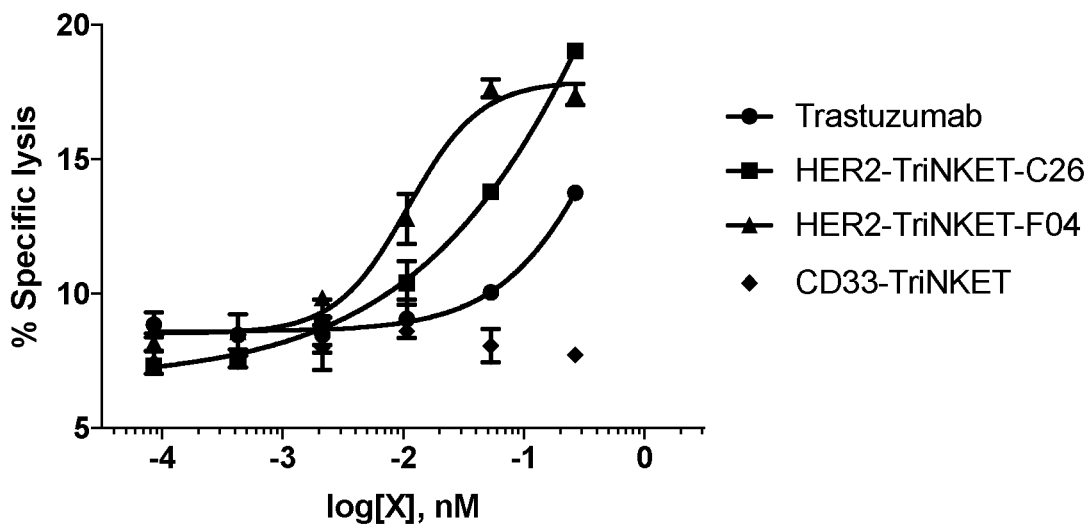
Figure 32C:
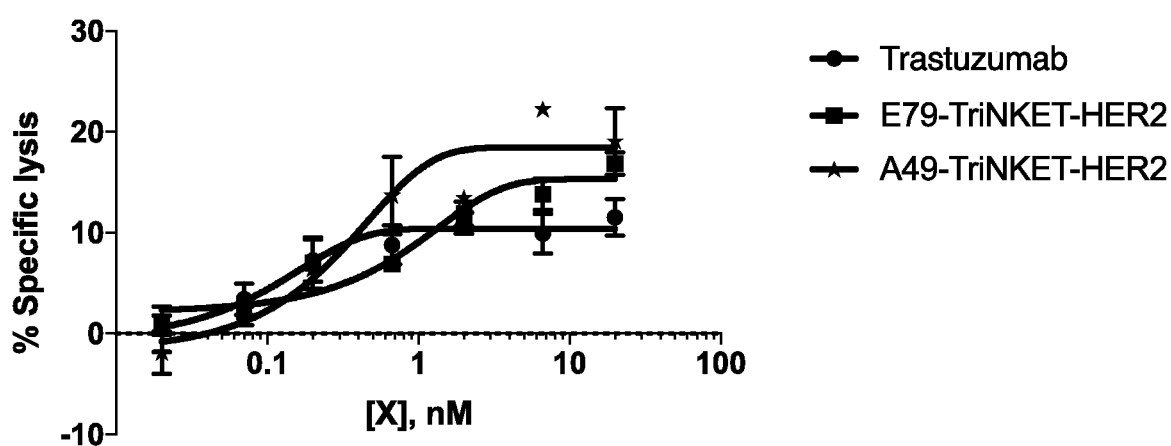

FIGS. 32A-32C show TriNKET enhancement of cytotoxic activity using IL-2-activated and rested human NK cells. FIG. 32A shows percent specific lysis of SkBr-3 tumor cells by rested human NK cells. FIG. 32B shows percent specific lysis of SkBr-3 tumor cells by IL-2-activated human NK cells. IL-2-activated and rested NK cell populations came from the same donor. Compared to trastuzumab, TriNKETs more potently direct responses against SkBr-3 cells by either activated or rested NK cell populations. FIG. 32C shows percent specific lysis of HER2-expressing NCI-H661 lung cancer cells by rested human NK cells. Two TriNKETs with different NKG2D-binding domains are able to induce higher maximal lysis of NCI-H661 HER2+ cancer cells compared to the monoclonal antibody Trastuzumab.

TriNKETs Enhance NK Cell Cytotoxicity Against Targets with Low Surface Expression Effects of TriNKETs against targets cells with low HER2 surface expression was investigated. FIGS. 29A-29B show TriNKETs provide a greater advantage against HER2-medium and low cancers compared to trastuzumab. FIG. 29A shows activated human NK cell killing of HER2-high SkBr-3 tumor cells. FIG. 29B shows human NK cell killing of HER2-low 786-0 tumor cells. TriNKETs provide a greater advantage compared to trastuzumab against cancer cells with low HER2 expression.

The Advantage of TriNKETs in Treating Cancers with High Expression of FcR, or in Tumor Microenvironments with High Levels of FcR Monoclonal antibody therapy has been approved for the treatment of many cancer types, including both hematological and solid tumors. While the use of monoclonal antibodies in cancer treatment has improved patient outcomes, there are still limitations. Mechanistic studies have demonstrated monoclonal antibodies exert their effects on tumor growth through multiple mechanisms including ADCC, CDC, phagocytosis, and signal blockade amongst others.

Most notably, ADCC is thought to be a major mechanism through which monoclonal antibodies exert their effect. ADCC relies on antibody Fc engagement of the low-affinity FcγRIII (CD16) on the surface of natural killer cells, which mediate direct lysis of the tumor cell. Amongst FcγR, CD16 has the lowest affinity for IgG Fc, FcγRI (CD64) is the high-affinity FcR, and binds about 1000 times stronger to IgG Fc than CD16.

CD64 is normally expressed on many hematopoietic lineages such as the myeloid lineage, and can be expressed on tumors derived from these cell types, such as acute myeloid leukemia (AML). Immune cells infiltrating into the tumor, such as MDSCs and monocytes, also express CD64 and are known to infiltrate the tumor microenvironment. Expression of CD64 by the tumor or in the tumor microenvironment can have a detrimental effect on monoclonal antibody therapy. Expression of CD64 in the tumor microenvironment makes it difficult for these antibodies to engage CD16 on the surface of NK cells, as the antibodies prefer to bind the high-affinity receptor. Through targeting two activating receptors on the surface of NK cells, TriNKETs may be able to overcome the detrimental effect of CD64 expression on monoclonal antibody therapy.

Killing of Normal Myeloid and Normal B Cells in PBMC Cultures: TriNKETs Provide Better Safety Profile Through Less On-Target Off-Tumor Side Effects Natural killer cells and CD8 T cells are both able to directly lyse tumor cells, although the mechanisms through which NK cells and CD8 T cell recognize normal self from tumor cells differ. The activity of NK cells is regulated by the balance of signals from activating (NCRs, NKG2D, CD16, etc.) and inhibitory (KIRs, NKG2A, etc.) receptors. The balance of these activating and inhibitory signals allow NK cells to determine healthy self-cells from stressed, virally infected, or transformed self-cells. This "built-in" mechanism of self-tolerance, will help protect normal healthy tissue from NK cell responses. To extend this principle, the self-tolerance of NK cells will allow TriNKETs to target antigens expressed both on self and tumor without off tumor side effects, or with an increased therapeutic window.

Unlike natural killer cells, T cells require recognition of a specific peptide presented by MHC molecules for activation and effector functions. T cells have been the primary target of immunotherapy, and many strategies have been developed to redirect T cell responses against the tumor. T cell bispecifics, checkpoint inhibitors, and CAR-T cells have all been approved by the FDA, but often suffer from dose-limiting toxicities. T cell bispecifics and CAR-T cells work around the TCR-MHC recognition system by using binding domains to target antigens on the surface of tumor cells, and using engineered signaling domains to transduce the activation signals into the effector cell. Although effective at eliciting an anti-tumor immune response these therapies are often coupled with cytokine release syndrome (CRS), and on-target off-tumor side effects. TriNKETs are unique in this context as they will not "override" the natural systems of NK cell activation and inhibition. Instead, TriNKETs are designed to sway the balance, and provide additional activation signals to the NK cells, while maintaining NK tolerance to healthy self.

PBMCs were isolated from whole blood by density gradient centrifugation. Any contaminating red blood cells were lysed by incubation in ACK lysis buffer. PBMCs were washed 3× in PBS, and total PBMCs were counted. PBMCs were adjusted to $10^6$/mL in primary cell culture media. 1 mL of PBMCs were seeded into wells of a 24 well plate, the indicated TriNKETs or mAbs were added to the PBMC cultures at 10 μg/mL. Cells were cultured overnight at 37° C. with 5% $CO_2$. The following day (24 hours later) PBMCs were harvested from culture and prepared for FACS analysis. The percentage of CD45+; CD19+B cells and CD45+; CD33+; CD11b+ myeloid cells was analyzed over the different treatment groups.

Figure 33B:
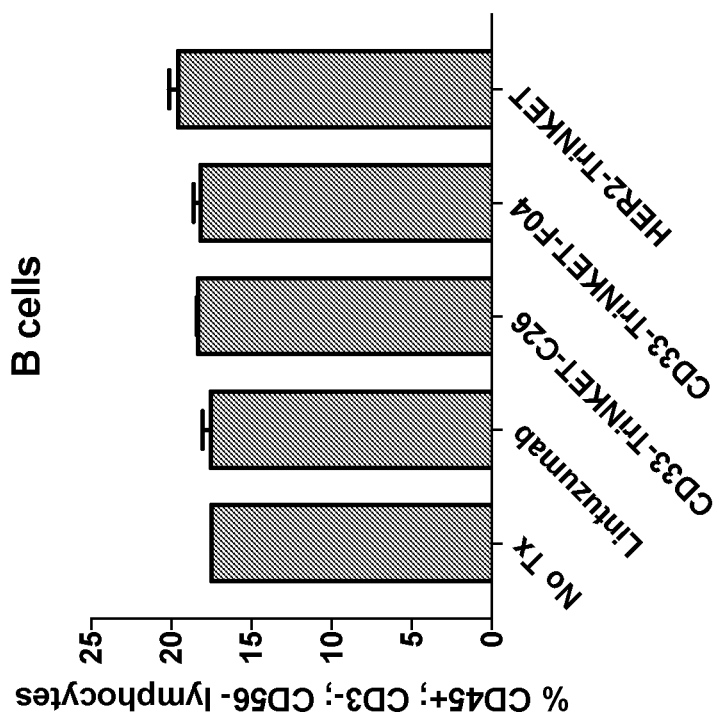
FIGS. 33A & 33B are bar graphs showing B cells from a health donor are sensitive to TriNKET-mediated lysis.
Figure 33A:
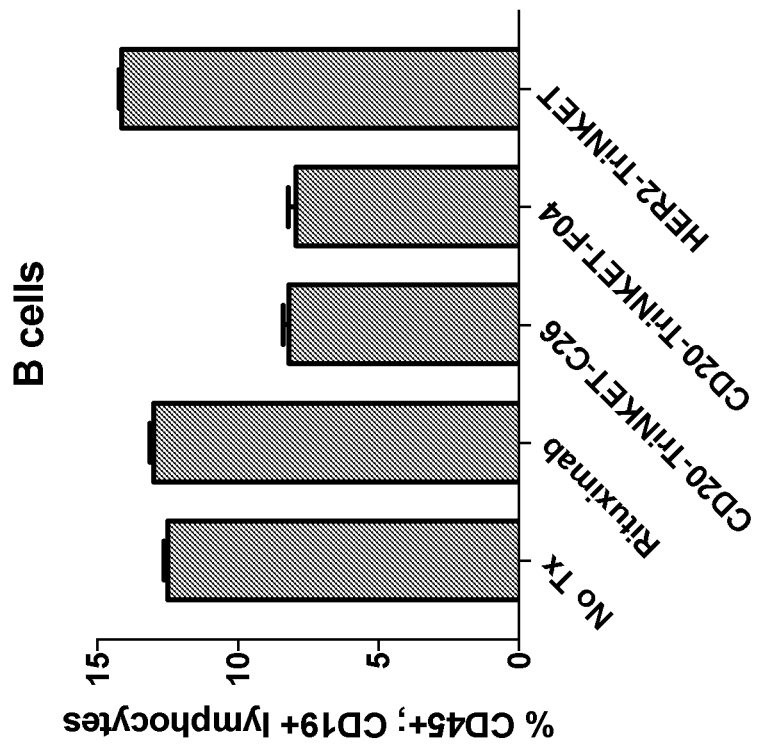
Figure 33D:
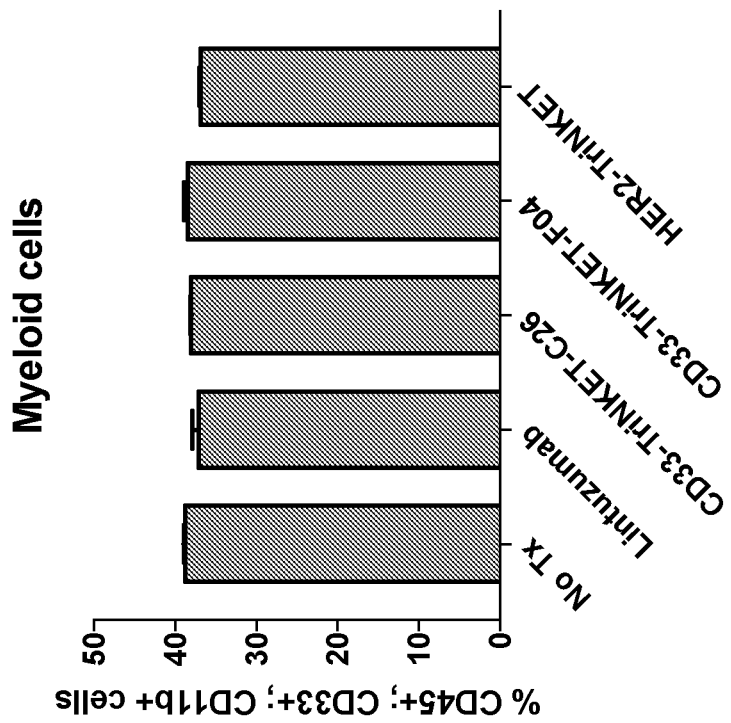
FIGS. 33C & 33D are bar graphs showing myeloid cells are resistant to TriNKET-mediated lysis.
Figure 33C:
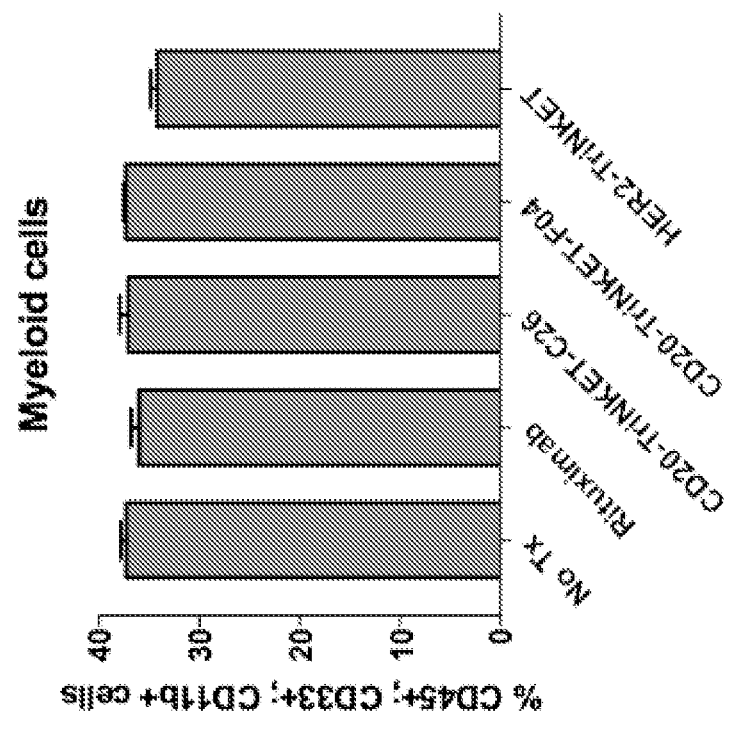

FIGS. 33A & 33B shows B cells from a health donor are sensitive to TriNKET mediated lysis, FIGS. 33C & 33D show that autologous myeloid cells are protected from TriNKET mediated NK cell responses, and, therefore, are resistant to TriNKET lysis. PBMCs treated with TriNKETs targeting CD20 showed reduced frequency of CD19+ B cells with the CD45+ lymphocyte population (FIG. 33A), but no effect in CD45+, CD3−, CD56− lymphocyte population (FIG. 33B). In these cultures the frequency of CD45+, CD33+, CD11b+ myeloid cells (FIG. 33C), or the frequency of CD45+, CD33+, CD11b+ myeloid cells (FIG. 33D) were unchanged.

Figure 34:
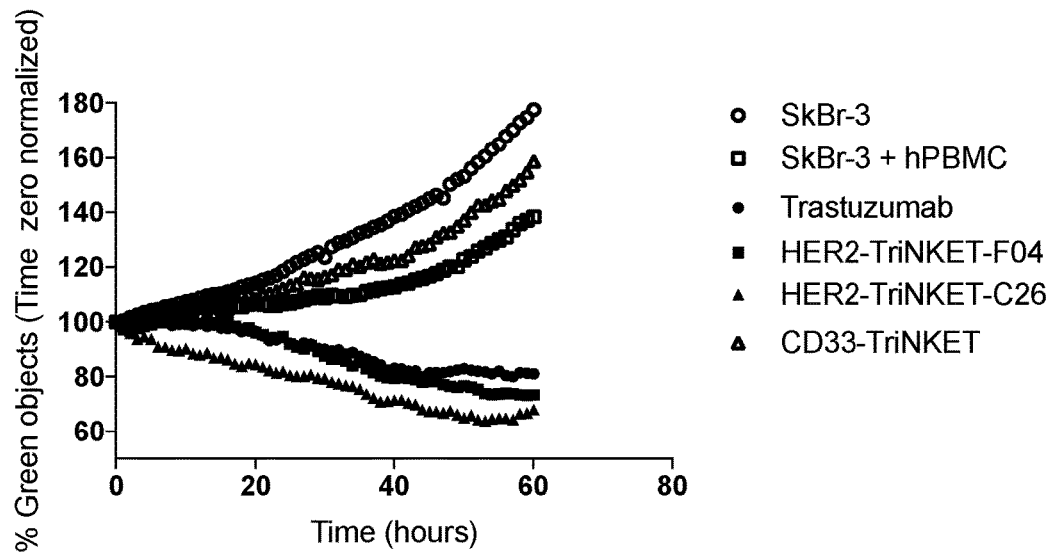
FIG. 34 are line graphs of TriNKETs-mediated hPBMC killing of SkBr-3 tumor cells in long-term co-cultures.

TriNKETs Mediate hPBMC Killing of SkBr-3 Tumor Cells in Long-Term Co-Cultures Primary Human PBMC Cytotoxicity Assay FIG. 34 shows long term killing of SkBr-3 cells in culture with human PBMCs. When cultured alone SkBr-3 cells proliferate and almost double in 60 hours. When human PBMCs are added to SkBr-3 cells in culture the rate of proliferation is slowed, and when an isotype control TriNKET targeting CD33 is added proliferation is also slowed, but to a lesser extent. When cultures are treated with Trastuzumab, SkBr-3 no longer proliferate and, after 60 hours, only 80% of the cells from time zero are left. As SkBr-3 cells are sensitive to HER2 signal blockade, the effect on SkBr-3 cell growth could be mediated by HER2 signal blockade or through Fc effector functions such as ADCC.

Example 15—Cytotoxic Activity of Rested Human NK Cells Mediated by TriNKETs, Monoclonal Antibodies, or Bispecific Antibodies Against HER2-Positive Cells PBMCs were isolated from human peripheral blood buffy coats using density gradient centrifugation. Isolated PBMCs were washed and prepared for NK cell isolation. NK cells were isolated using a negative selection technique with magnetic beads; the purity of the isolated NK cells was typically >90% CD3−CD56+. Isolated NK cells were cultured in media containing 100 ng/mL IL-2 or were rested overnight without cytokine. IL-2-activated or rested NK cells were used the following day in cytotoxicity assays.
DELFIA Cytotoxicity Assay:

Human cancer cell lines expressing a target of interest were harvested from culture, cells were washed with HBS, and were resuspended in growth media at $10^6$/mL for labeling with BATDA reagent (Perkin Elmer AD0116). Manufacturer instructions were followed for labeling of the target cells. After labeling, cells were washed 3× with HBS, and were resuspended at $0.5-1.0\times10^5$/mL in culture media. To prepare the background wells an aliquot of the labeled cells was put aside, and the cells were spun out of the media. 100 μl of the media was carefully added to wells in triplicate to avoid disturbing the pelleted cells. 100 μl of BATDA labeled cells were added to each well of the 96-well plate. Wells were saved for spontaneous release from target cells, and wells were prepared for maximal lysis of target cells by addition of 1% Triton-X. Monoclonal antibodies or TriNKETs against the tumor target of interest were diluted in culture media and 50 μl of diluted mAb or TriNKET was added to each well. Rested and/or activated NK cells were harvested from culture, the cells were washed and were resuspended at $10^5$-$2.0\times10^6$/mL in culture media depending on the desired E:T ratio. 50 μl of NK cells were added to each well of the plate to make a total 200 μl culture volume. The plate was incubated at 37° C. with 5% $CO_2$ for 2-3 hours before developing the assay.

After culturing for 2-3 hours, the plate was removed from the incubator and the cells were pelleted by centrifugation at 200 g for 5 minutes. 20 μl of culture supernatant was transferred to a clean microplate provided from the manufacturer and 200 μl of room temperature europium solution was added to each well. The plate was protected from the light and incubated on a plate shaker at 250 rpm for 15 minutes. The plate was read using either Victor 3 or SpectraMax i3X instruments. % Specific lysis was calculated as follows: % Specific lysis=((Experimental release−Spontaneous release)/(Maximum release−Spontaneous release))*100%.

Figure 35:
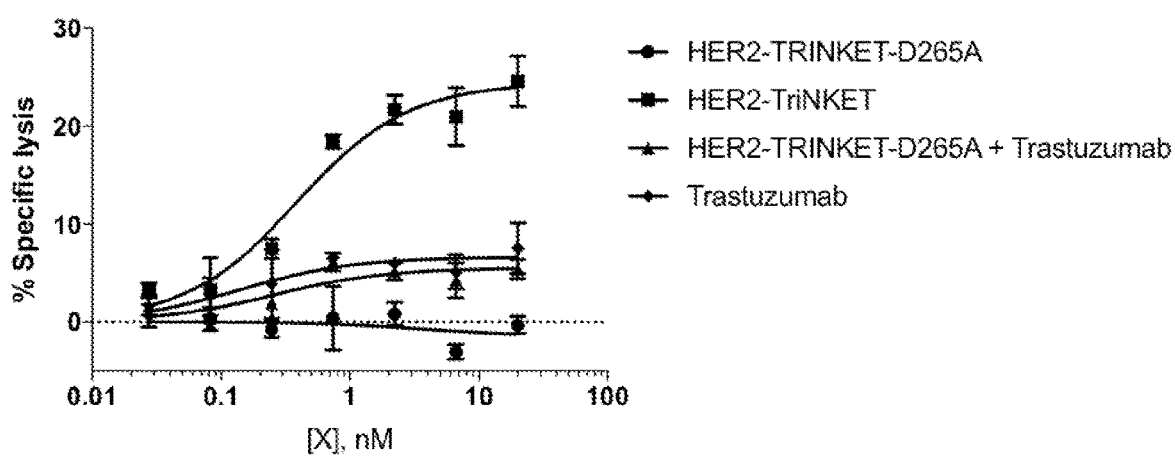
FIG. 35 is a line graph showing tri-specific binding in one molecule is important for maximal NK cell activity.

Combination of Monoclonal Antibody and Bispecifc NK Cell Engager does not Recapitulate TriNKET Activity FIG. 35 shows the cytotoxic activity of rested human NK cells mediated by TriNKETs, monoclonal antibodies, or bispecific antibodies against the HER2-positive Colo-201 cell line. A TriNKET (ADI-29404 (F04)) targeting HER2-induced maximum lysis of Colo-201 cells by rested human NK cells. The D265A mutation was introduced into the CH2 domain of the TriNKET to abrogate FcR binding. The HER2-TriNKET (ADI-29404 (F04))-D265A failed to mediate lysis of Colo-201 cells, demonstrating the importance of dual targeting of CD16 and NKG2D on NK cells. To further demonstrate the importance of dual targeting on NK cells, the monoclonal antibody Trastuzumab was used to target HER2 and mediate ADCC by NK cells, Trastuzumab alone was able to increase NK cell lysis of Colo-201 cells, but maximum lysis achieved by Trastuzumab alone was about 4× lower compared to the TriNKET. To understand the importance of having CD16 and NKG2D targeting on the same molecule, TriNKET (ADI-29404 (F04)) activity was compared to the activity of a bispecific antibody targeting HER2 and NKG2D, combined with Trastuzumab. When used at equimolar concentrations the combination of bispecific and Trastuzumab was not able to mediate maximal lysis of Colo-201 cells by rested human NK cells. The failure of Trastuzumab+bispecific combination demonstrates the importance of containing the trispecific-binding of TriNKETs in one molecule.

Example 16—Bridging Assay

Figure 38A:
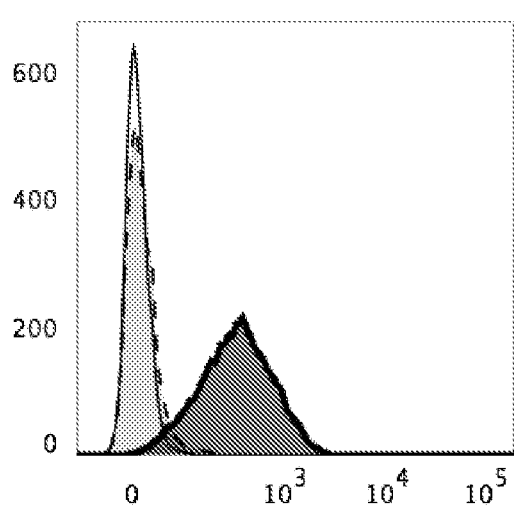
FIG. 38A shows that HER2-TriNKET-C26 bridges hNKG2D-Fc to RMA-HER2 cells.
Figure 38B:
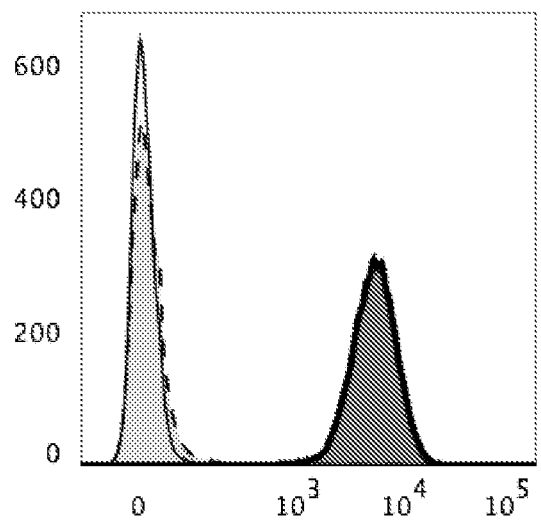
FIG. 38B shows HER2-TriNKET-F04 bridges hNKG2D-Fc to RMA-HER2 cells. Dotted line represents isotype control. Solid line without fill represents unstained control. Solid line with fill represents the TriNKETs.
Figure 39:
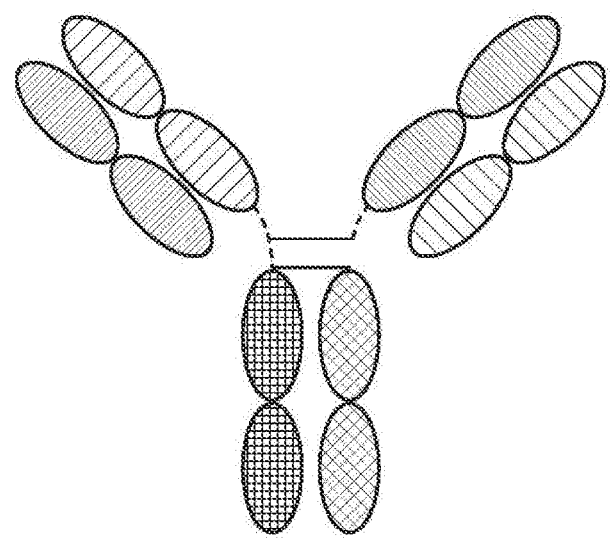
FIG. 39 is a representation of a TriNKET in the Triomab form, which is a trifunctional, bispecific antibody that maintains an IgG-like shape. This chimera consists of two half antibodies, each with one light and one heavy chain, that originate from two parental antibodies. Triomab form may be an heterodimeric construct containing 2 of rat antibody and ½ of mouse antibody.
Figure 40:
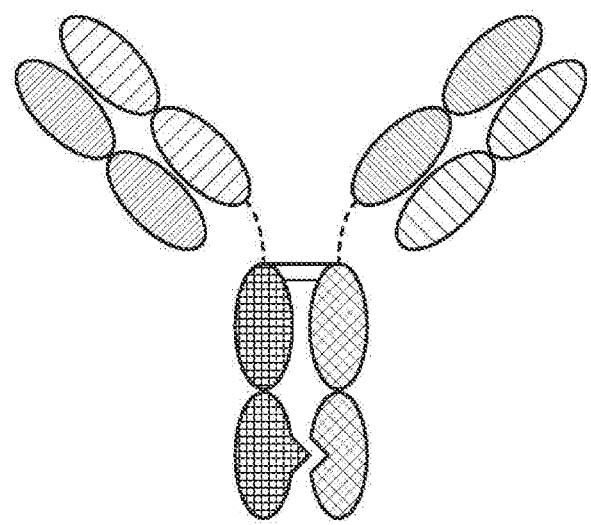
FIG. 40 is a representation of a TriNKET in the KiH Common Light Chain (LC) form, which involves the knobs-into-holes (KIHs) technology. KiH is a heterodimer containing 2 Fabs binding to target 1 and 2, and an Fc stabilized by heterodimerization mutations. TriNKET in the KiH format may be an heterodimeric construct with 2 fabs binding to target 1 and target 2, containing two different heavy chains and a common light chain that pairs with both heavy chains.
Figure 41:
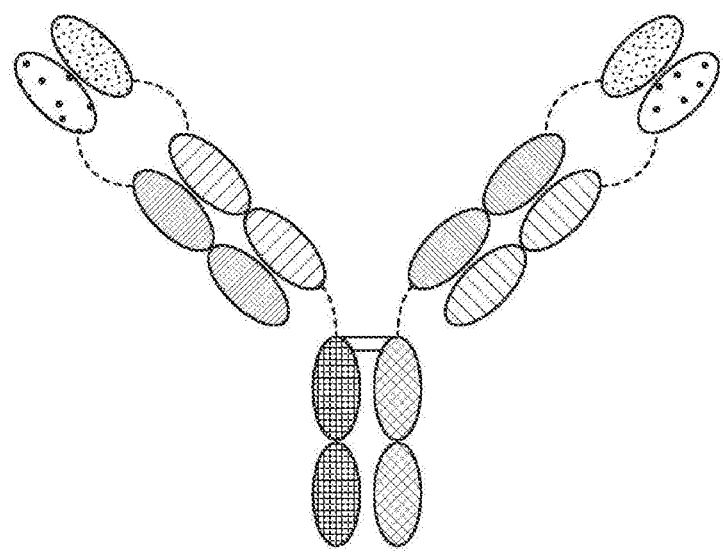
FIG. 41 is a representation of a TriNKET in the dual-variable domain immunoglobulin (DVD-Ig™) form, which combines the target binding domains of two monoclonal antibodies via flexible naturally occurring linkers, and yields a tetravalent IgG-like molecule. DVD-Ig™ is an homodimeric construct where variable domain targeting antigen 2 is fused to the N terminus of variable domain of Fab targeting antigen 1 Construct contains normal Fc.
Figure 42:
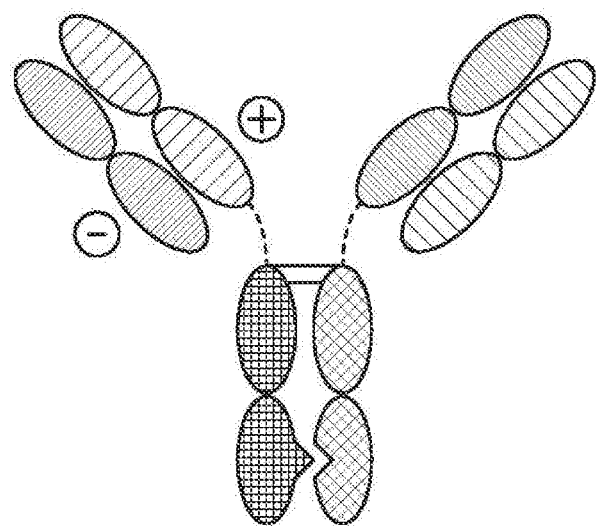
FIG. 42 is a representation of a TriNKET in the Orthogonal Fab interface (Ortho-Fab) form, which is an heterodimeric construct that contains 2 Fabs binding to target1 and target 2 fused to Fc. LC-HC pairing is ensured by orthogonal interface. Heterodimerization is ensured by mutations in the Fc.
Figure 43:
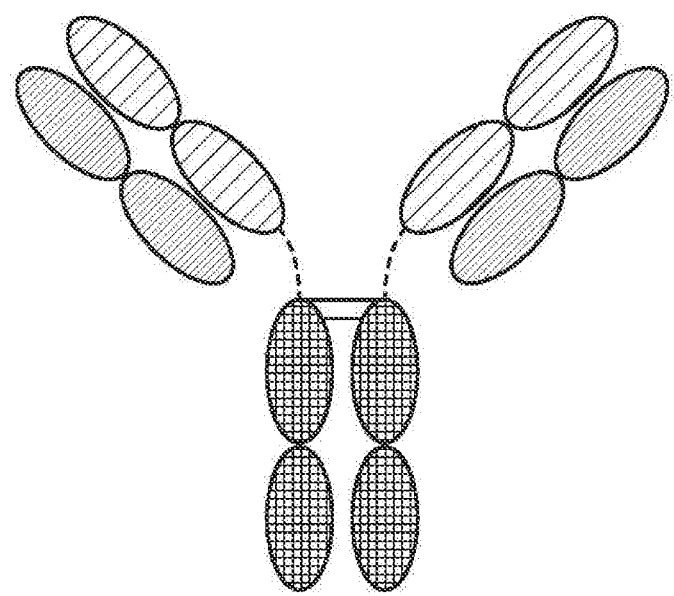
FIG. 43 is a representation of a TrinKET in the 2-in-1 Ig format.
Figure 44:
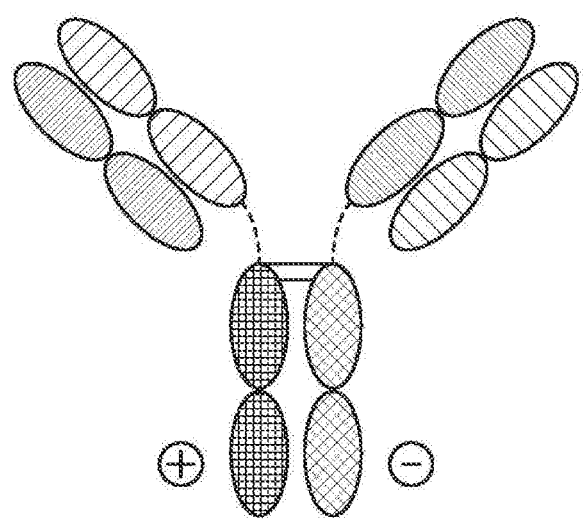
FIG. 44 is a representation of a TriNKET in the ES form, which is an heterodimeric construct containing two different Fabs binding to target 1 and target 2 fused to the Fc. Heterodimerization is ensured by electrostatic steering mutations in the Fc.
Figure 45:
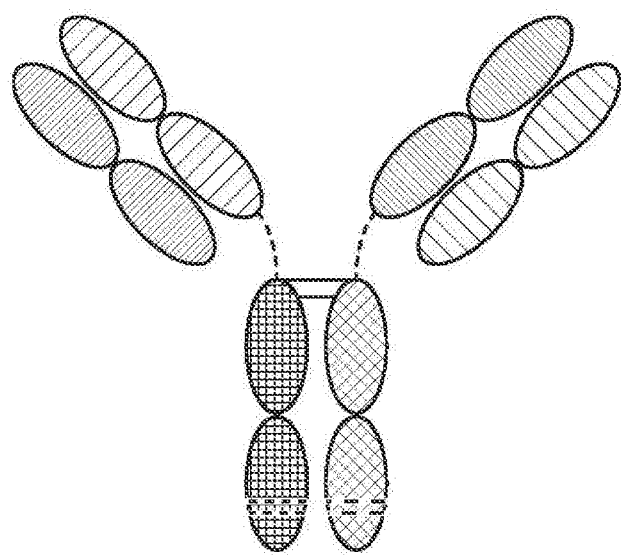
FIG. 45 is a representation of a TriNKET in the Fab Arm Exchange form: antibodies that exchange Fab arms by swapping a heavy chain and attached light chain (half-molecule) with a heavy-light chain pair from another molecule, resulting in bispecific antibodies. Fab Arm Exchange form (cFae) is a heterodimer containing 2 Fabs binding to target 1 and 2, and an Fc stabilized by heterodimerization mutations.
Figure 46:
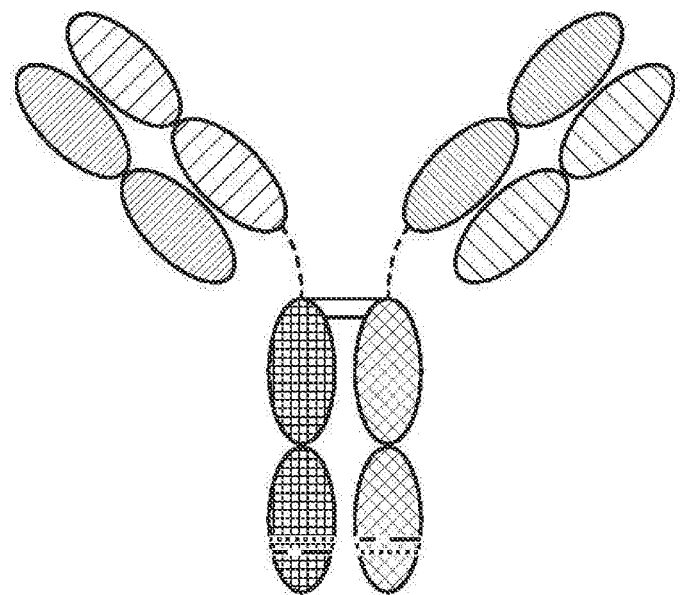
FIG. 46 is a representation of a TriNKET in the SEED Body form, which is an heterodimer containing 2 Fabs binding to target 1 and 2, and an Fc stabilized by heterodimerization mutations.
Figure 47:
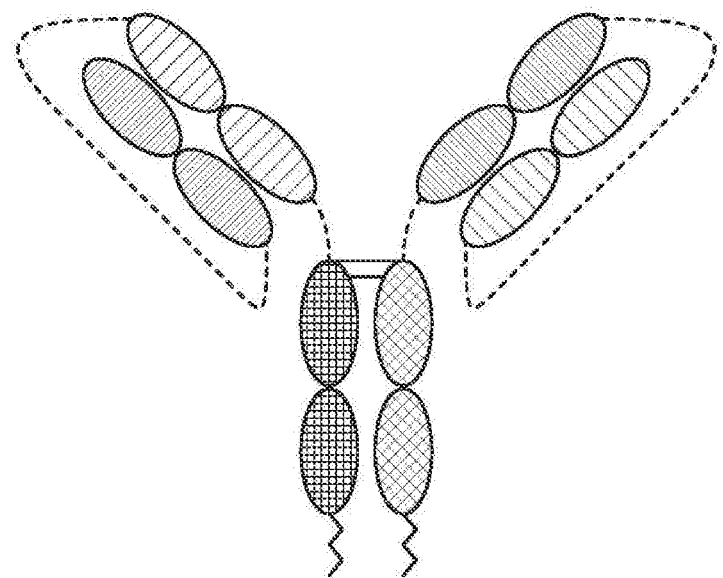
FIG. 47 is a representation of a TriNKET in the LuZ-Y form, in which leucine zipper is used to induce heterodimerization of two different HCs. LuZ-Y form is a heterodimer containing two different scFabs binding to target 1 and 2, fused to Fc. Heterodimerization is ensured through leucine zipper motifs fused to C-terminus of Fc.
Figure 48:
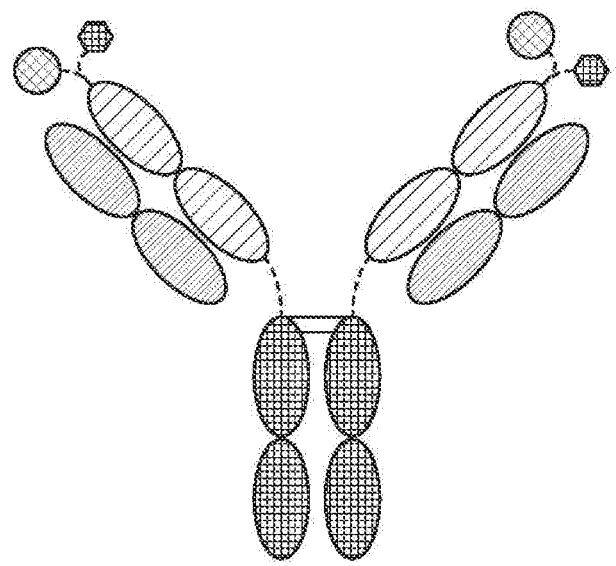
FIG. 48 is a representation of a TriNKET in the Cov-X-Body form.

RMA cells transduced with human HER2 were used to test simultaneous binding to HER2 and NKG2D by HER2 targeting TriNKETs. The TriNKETs were used to stain surface HER2 at 20 µg/mL. Binding of the TriNKET was then detected using biotinylated recombinant human NKG2D-Fc. Bound NKG2D-Fc was then detected using streptavidin-APC. Cells were analyzed by flow cytometry, and TriNKET-bridging was compared to isotype stained and unstained cell populations. FIG. 38A shows that TriNKET-C26 that includes a binding domain for HER2, bridges hNKG2D-Fc to RMA-HER2 cells, and FIG. 38B shows TriNKET-F04 that includes a binding domain for HER2, bridges hNKG2D-Fc to RMA-HER2 cells.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A protein comprising:
   (a) a first antigen-binding site that binds NKG2D;
   (b) a second antigen-binding site that binds HER2; and
   (c) a first antibody Fc domain of human IgG1 or a portion thereof and a second antibody Fc domain of human IgG1 or a portion thereof that together are sufficient to bind CD16, wherein the first antibody Fc domain or the portion thereof and the second antibody Fc domain or the portion thereof comprise different amino acid mutations to promote heterodimerization,
   wherein the first antigen-binding site comprises a heavy chain variable domain comprising the amino acid sequence of SEQ ID NO:1 and a light chain variable domain comprising the amino acid sequence of SEQ ID NO:2.

2. The protein of claim 1, wherein the first antigen-binding site binds to NKG2D in humans and non-human primates.

3. The protein according to claim 1, wherein the second antigen-binding site comprises a heavy chain variable domain and a light chain variable domain.

4. The protein according to claim 3, wherein the heavy chain variable domain and the light chain variable domain of the second antigen-binding site are present on the same polypeptide.

5. The protein according to claim 1, wherein the second antigen-binding site comprises:
   a heavy chain CDR1 sequence identical to the amino acid sequence of SEQ ID NO:50;
   a heavy chain CDR2 sequence identical to the amino acid sequence of SEQ ID NO:51;

a heavy chain CDR3 sequence identical to the amino acid sequence of SEQ ID NO:52;
a light chain CDR1 sequence identical to the amino acid sequence of SEQ ID NO:54;
a light chain CDR2 sequence identical to the amino acid sequence of SEQ ID NO:55; and
a light chain CDR3 sequence identical to the amino acid sequence of SEQ ID NO:56.

6. The protein according to claim 5, wherein the second antigen-binding site comprises a heavy chain variable domain comprising an amino acid sequence at least 90% identical to SEQ ID NO:49 and a light chain variable domain comprising an amino acid sequence at least 90% identical to SEQ ID NO:53.

7. The protein according to claim 1, wherein the second antigen-binding site comprises:
a heavy chain CDR1 sequence identical to the amino acid sequence of SEQ ID NO:77;
a heavy chain CDR2 sequence identical to the amino acid sequence of SEQ ID NO:78;
a heavy chain CDR3 sequence identical to the amino acid sequence of SEQ ID NO:79;
a light chain CDR1 sequence identical to the amino acid sequence of SEQ ID NO:80;
a light chain CDR2 sequence identical to the amino acid sequence of SEQ ID NO:81; and
a light chain CDR3 sequence identical to the amino acid sequence of SEQ ID NO:82.

8. The protein according to claim 7, wherein the second antigen-binding site comprises a heavy chain variable domain comprising an amino acid sequence at least 90% identical to SEQ ID NO:57 and a light chain variable domain comprising an amino acid sequence at least 90% identical to SEQ ID NO:58.

9. The protein according to claim 1, wherein the first and second antibody Fc domains or the portions thereof each comprise hinge and CH2 domains.

10. The protein according to claim 9, wherein the first and second antibody Fc domains or the portions thereof each comprise an amino acid sequence at least 90% identical to amino acids 234-332 of a human IgG1 antibody.

11. The protein according to claim 9, wherein the first and second antibody Fc domains each comprise an amino acid sequence at least 90% identical to the Fc domain of human IgG1, and the amino acid mutations to promote heterodimerization comprise one or more mutations at Q347, Y349, T350, L351, S354, E356, E357, K360, Q362, S364, T366, L368, K370, N390, K392, T394, D399, S400, D401, F405, Y407, K409, T411, and/or K439, numbered according to the EU index as in Kabat.

12. A formulation comprising a protein according to claim 1 and a pharmaceutically acceptable carrier.

13. A cell comprising one or more nucleic acids encoding a protein according to claim 1.

14. The protein according to claim 1, wherein the second antigen-binding site comprises:
a heavy chain CDR1 sequence identical to the amino acid sequence of SEQ ID NO:83;
a heavy chain CDR2 sequence identical to the amino acid sequence of SEQ ID NO:84;
a heavy chain CDR3 sequence identical to the amino acid sequence of SEQ ID NO:85;
a light chain CDR1 sequence identical to the amino acid sequence of SEQ ID NO:86;
a light chain CDR2 sequence identical to the amino acid sequence of SEQ ID NO:87; and
a light chain CDR3 sequence identical to the amino acid sequence of SEQ ID NO:88.

15. The protein according to claim 14, wherein the second antigen-binding site comprises a heavy chain variable domain comprising an amino acid sequence at least 90% identical to SEQ ID NO:59 and a light chain variable domain comprising an amino acid sequence at least 90% identical to SEQ ID NO:60.

* * * * *

SEQUENCE LISTING

```
<160> NUMBER OF SEQ ID NOS: 109

<210> SEQ ID NO 1
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 2
```

<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Ile
                85                  90                  95

Thr Phe Gly Gly Gly Thr Lys Val Glu Ile Lys
            100                 105

<210> SEQ ID NO 3
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 4
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gly Gly Thr Lys Val Glu Ile Lys
            100                 105

<210> SEQ ID NO 5
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 6
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Ser Phe Tyr Thr
                85                  90                  95

Phe Gly Gly Gly Thr Lys Val Glu Ile Lys
            100                 105

<210> SEQ ID NO 7
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 8
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Asn Ser Tyr Tyr Thr
                85                  90                  95

Phe Gly Gly Gly Thr Lys Val Glu Ile Lys
            100                 105

<210> SEQ ID NO 9
<211> LENGTH: 117
<212> TYPE: PRT
<213> ORGANISM: Artificial Sequence
<220> FEATURE:

<223> OTHER INFORMATION: Description of Artificial Sequence: Synthetic
     polypeptide

<400> SEQUENCE: 9

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 10
<211> LENGTH: 106
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 10

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Thr
                85                  90                  95

Phe Gly Gly Gly Thr Lys Val Glu Ile Lys
            100                 105

<210> SEQ ID NO 11
<211> LENGTH: 117
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 11

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile

```
                35                  40                  45
Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Gly Phe Asp Pro Trp Gly Gln Gly Thr Leu
            100                 105                 110

Val Thr Val Ser Ser
            115

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Leu Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Ser Tyr
            20                  25                  30

Leu Asn Trp Tyr Gln Gln Lys Pro Gly Gln Pro Pro Lys Leu Leu Ile
        35                  40                  45

Tyr Trp Ala Ser Thr Arg Glu Ser Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ser Tyr Asp Ile Pro Tyr
                85                  90                  95

Thr Phe Gly Gln Gly Thr Lys Leu Glu Ile Lys
            100                 105

<210> SEQ ID NO 13
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
```

Val Thr Val Ser Ser
        115

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Ser Phe Pro Ile
                85                  90                  95

Thr Phe Gly Gly Gly Thr Lys Val Glu Ile Lys
            100                 105

<210> SEQ ID NO 15
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 16

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Ser Lys Glu Val Pro Trp
                85                  90                  95

Thr Phe Gly Gln Gly Thr Lys Val Glu Ile Lys
            100                 105

<210> SEQ ID NO 17
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 18
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
            50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Phe Pro Thr
                85                  90                  95

Phe Gly Gly Gly Thr Lys Val Glu Ile Lys
            100                 105

<210> SEQ ID NO 19
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 20
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asp Ile Tyr Pro Thr
                85                  90                  95

Phe Gly Gly Gly Thr Lys Val Glu Ile Lys
            100                 105

<210> SEQ ID NO 21
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
            115

<210> SEQ ID NO 22
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Tyr Pro Thr
                85                  90                  95

Phe Gly Gly Gly Thr Lys Val Glu Ile Lys
            100                 105

<210> SEQ ID NO 23
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
            115
```

<210> SEQ ID NO 24
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Ser Phe Pro Thr
                85                  90                  95

Phe Gly Gly Gly Thr Lys Val Glu Ile Lys
            100                 105
```

<210> SEQ ID NO 25
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60
```

```
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Arg Gly Pro Trp Ser Phe Asp Pro Trp Gly Gln Gly Thr Leu
            100                 105                 110

Val Thr Val Ser Ser
        115
```

<210> SEQ ID NO 26
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Gln Ser Phe Pro Thr
                 85                  90                  95

Phe Gly Gly Gly Thr Lys Val Glu Ile Lys
            100                 105
```

<210> SEQ ID NO 27
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Arg Gly Pro Trp Ser Phe Asp Pro Trp Gly Gln Gly Thr Leu
            100                 105                 110

Val Thr Val Ser Ser
        115
```

<210> SEQ ID NO 28
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Phe Ser Thr
                85                  90                  95

Phe Gly Gly Gly Thr Lys Val Glu Ile Lys
            100                 105

<210> SEQ ID NO 29
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 30
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Pro Ser Thr Leu Ser Ala Ser Val Gly

```
                1               5                  10                 15
Asp Arg Val Thr Ile Thr Cys Arg Ala Ser Gln Ser Ile Ser Ser Trp
                    20                  25                 30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Ser Tyr Ser Thr
                85                  90                  95

Phe Gly Gly Gly Thr Lys Val Glu Ile Lys
            100                 105

<210> SEQ ID NO 31
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 32
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
```

```
                 65                  70                  75                  80

Asp Asp Phe Ala Thr Tyr Tyr Cys Gln Gln Tyr Asp Ser Phe Ile Thr
                 85                  90                  95

Phe Gly Gly Gly Thr Lys Val Glu Ile Lys
                100                 105

<210> SEQ ID NO 33
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
                100                 105                 110

Val Thr Val Ser Ser
        115

<210> SEQ ID NO 34
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ser Tyr Pro Thr
                85                  90                  95

Phe Gly Gly Gly Thr Lys Val Glu Ile Lys
                100                 105

<210> SEQ ID NO 35
<211> LENGTH: 117
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
            115

<210> SEQ ID NO 36
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Ser Phe Pro Thr
                85                  90                  95

Phe Gly Gly Gly Thr Lys Val Glu Ile Lys
            100                 105

<210> SEQ ID NO 37
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
            115

<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Leu Tyr Ser Tyr
                85                  90                  95

Thr Phe Gly Gly Gly Thr Lys Val Glu Ile Lys
            100                 105

<210> SEQ ID NO 39
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

```
Arg Ala Arg Gly Pro Trp Ser Phe Asp Pro Trp Gly Gln Gly Thr Leu
            100                 105                 110

Val Thr Val Ser Ser
        115

<210> SEQ ID NO 40
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Phe Ile Thr
                85                  90                  95

Phe Gly Gly Gly Thr Lys Val Glu Ile Lys
            100                 105

<210> SEQ ID NO 41
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Ser Ser Ile Arg His Ala Tyr Tyr Tyr Gly Met
            100                 105                 110

Asp Val Trp Gly Gln Gly Thr Thr Val Thr Val Ser Ser
        115                 120                 125

<210> SEQ ID NO 42
<211> LENGTH: 113
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 42

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Ile Thr Phe Gly Gly Gly Thr Lys Val Glu Ile
            100                 105                 110

Lys

<210> SEQ ID NO 43
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ser Asp Arg Phe His Pro Tyr Phe Asp Tyr Trp Gly
            100                 105                 110

Gln Gly Thr Leu Val Thr Val Ser Ser
        115                 120

<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
```

```
            20                  25                  30
Leu Ala Trp Tyr Gln Gln Lys Pro Gly Gln Ala Pro Arg Leu Leu Ile
                35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Phe Asp Thr Trp Pro Pro
                 85                  90                  95

Thr Phe Gly Gly Gly Thr Lys Val Glu Ile Lys
               100                 105
```

<210> SEQ ID NO 45
<211> LENGTH: 121
<212> TYPE: PRT
<213> ORGANISM: Homo sapiens

<400> SEQUENCE: 45

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
                35                  40                  45

Ala Phe Ile Arg Tyr Asp Gly Ser Asn Lys Tyr Tyr Ala Asp Ser Val
         50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Arg Gly Leu Gly Asp Gly Thr Tyr Phe Asp Tyr Trp Gly
                100                 105                 110

Gln Gly Thr Thr Val Thr Val Ser Ser
            115                 120
```

<210> SEQ ID NO 46
<211> LENGTH: 110
<212> TYPE: PRT
<213> ORGANISM: Homo sapiens

<400> SEQUENCE: 46

```
Gln Ser Ala Leu Thr Gln Pro Ala Ser Val Ser Gly Ser Pro Gly Gln
 1               5                  10                  15

Ser Ile Thr Ile Ser Cys Ser Gly Ser Ser Ser Asn Ile Gly Asn Asn
                20                  25                  30

Ala Val Asn Trp Tyr Gln Gln Leu Pro Gly Lys Ala Pro Lys Leu Leu
                35                  40                  45

Ile Tyr Tyr Asp Asp Leu Leu Pro Ser Gly Val Ser Asp Arg Phe Ser
         50                  55                  60

Gly Ser Lys Ser Gly Thr Ser Ala Phe Leu Ala Ile Ser Gly Leu Gln
 65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
                100                 105                 110
```

<210> SEQ ID NO 47
<211> LENGTH: 115
<212> TYPE: PRT
<213> ORGANISM: Homo sapiens

<400> SEQUENCE: 47

Gln Val His Leu Gln Glu Ser Gly Pro Gly Leu Val Lys Pro Ser Glu
1               5                   10                  15

Thr Leu Ser Leu Thr Cys Thr Val Ser Asp Ser Ile Ser Ser Tyr
            20                  25                  30

Tyr Trp Ser Trp Ile Arg Gln Pro Pro Gly Lys Gly Leu Glu Trp Ile
        35                  40                  45

Gly His Ile Ser Tyr Ser Gly Ser Ala Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Asn Trp Asp Asp Ala Phe Asn Ile Trp Gly Gln Gly Thr Met Val Thr
            100                 105                 110

Val Ser Ser
        115

<210> SEQ ID NO 48
<211> LENGTH: 108
<212> TYPE: PRT
<213> ORGANISM: Homo sapiens

<400> SEQUENCE: 48

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 49
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

```
Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Phe Asn Ile Lys Asp Thr
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Tyr Pro Thr Asn Gly Tyr
1               5

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Trp Gly Gly Asp Gly Phe Tyr Ala Met Asp Tyr
1               5                   10

<210> SEQ ID NO 53
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
```

```
            50                  55                  60
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys
            100                 105

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Asp Val Asn Thr Ala Val Ala
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Ala Ser Phe Leu Tyr Ser
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Gln His Tyr Thr Thr Pro Pro Thr
1               5

<210> SEQ ID NO 57
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
 65                 70                  75                  80
```

```
Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala
        115                 120

<210> SEQ ID NO 58
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg
            100                 105

<210> SEQ ID NO 59
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Tyr Pro Thr Asn Gly Tyr Thr Arg Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Ala Ser Val Thr Val Ser Ser Ala
        115                 120

<210> SEQ ID NO 60
<211> LENGTH: 108
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
    50                  55                  60

Ser Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Gly Gly Thr Lys Val Glu Ile Lys Arg
            100                 105

<210> SEQ ID NO 61
<211> LENGTH: 1255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205
```

-continued

```
Ser Glu Asp Cys Gln Ser Leu Thr Arg Thr Val Cys Ala Gly Gly Cys
    210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
            260                 265                 270
Thr Tyr Asn Thr Asp Thr Phe Glu Ser Met Pro Asn Pro Glu Gly Arg
        275                 280                 285
Tyr Thr Phe Gly Ala Ser Cys Val Thr Ala Cys Pro Tyr Asn Tyr Leu
    290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
            340                 345                 350
Val Arg Ala Val Thr Ser Ala Asn Ile Gln Glu Phe Ala Gly Cys Lys
        355                 360                 365
Lys Ile Phe Gly Ser Leu Ala Phe Leu Pro Glu Ser Phe Asp Gly Asp
    370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
            420                 425                 430
Gly Arg Ile Leu His Asn Gly Ala Tyr Ser Leu Thr Leu Gln Gly Leu
        435                 440                 445
Gly Ile Ser Trp Leu Gly Leu Arg Ser Leu Arg Glu Leu Gly Ser Gly
    450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
        515                 520                 525
Val Asn Cys Ser Gln Phe Leu Arg Gly Gln Glu Cys Val Glu Glu Cys
    530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
        595                 600                 605
Ser Tyr Met Pro Ile Trp Lys Phe Pro Asp Glu Glu Gly Ala Cys Gln
    610                 615                 620
Pro Cys Pro Ile Asn Cys Thr His Ser Cys Val Asp Leu Asp Asp Lys
```

-continued

```
            625                 630                 635                 640
Gly Cys Pro Ala Glu Gln Arg Ala Ser Pro Leu Thr Ser Ile Ile Ser
                    645                 650                 655
Ala Val Val Gly Ile Leu Leu Val Val Val Leu Gly Val Val Phe Gly
                    660                 665                 670
Ile Leu Ile Lys Arg Arg Gln Gln Lys Ile Arg Lys Tyr Thr Met Arg
                    675                 680                 685
Arg Leu Leu Gln Glu Thr Glu Leu Val Glu Pro Leu Thr Pro Ser Gly
                    690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                    725                 730                 735
Gly Ile Trp Ile Pro Asp Gly Glu Asn Val Lys Ile Pro Val Ala Ile
                    740                 745                 750
Lys Val Leu Arg Glu Asn Thr Ser Pro Lys Ala Asn Lys Glu Ile Leu
                    755                 760                 765
Asp Glu Ala Tyr Val Met Ala Gly Val Gly Ser Pro Tyr Val Ser Arg
                    770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                    805                 810                 815
Leu Gly Ser Gln Asp Leu Leu Asn Trp Cys Met Gln Ile Ala Lys Gly
                    820                 825                 830
Met Ser Tyr Leu Glu Asp Val Arg Leu Val His Arg Asp Leu Ala Ala
                    835                 840                 845
Arg Asn Val Leu Val Lys Ser Pro Asn His Val Lys Ile Thr Asp Phe
                    850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                    885                 890                 895
Arg Arg Phe Thr His Gln Ser Asp Val Trp Ser Tyr Gly Val Thr Val
                    900                 905                 910
Trp Glu Leu Met Thr Phe Gly Ala Lys Pro Tyr Asp Gly Ile Pro Ala
                    915                 920                 925
Arg Glu Ile Pro Asp Leu Leu Glu Lys Gly Glu Arg Leu Pro Gln Pro
                    930                 935                 940
Pro Ile Cys Thr Ile Asp Val Tyr Met Ile Met Val Lys Cys Trp Met
945                 950                 955                 960
Ile Asp Ser Glu Cys Arg Pro Arg Phe Arg Glu Leu Val Ser Glu Phe
                    965                 970                 975
Ser Arg Met Ala Arg Asp Pro Gln Arg Phe Val Val Ile Gln Asn Glu
                    980                 985                 990
Asp Leu Gly Pro Ala Ser Pro Leu Asp Ser Thr Phe Tyr Arg Ser Leu
                    995                 1000                1005
Leu Glu Asp Asp Asp Met Gly Asp Leu Val Asp Ala Glu Glu Tyr
                    1010                1015                1020
Leu Val Pro Gln Gln Gly Phe Phe Cys Pro Asp Pro Ala Pro Gly
                    1025                1030                1035
Ala Gly Gly Met Val His His Arg His Arg Ser Ser Ser Thr Arg
                    1040                1045                1050
```

```
Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Ser Phe Ser Gly Tyr Tyr Trp Ser
1               5

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Glu Ile Asp His Ser Gly Ser Thr Asn Tyr Asn Pro Ser Leu Lys Ser
1               5                   10                  15

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 64

Ala Arg Ala Arg Gly Pro Trp Ser Phe Asp Pro
1               5                   10

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Thr Phe Ser Ser Tyr Ala Ile Ser
1               5

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Ile Ile Pro Ile Phe Gly Thr Ala Asn Tyr Ala Gln Lys Phe Gln
1               5                   10                  15

Gly

<210> SEQ ID NO 67
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Arg Gly Asp Ser Ser Ile Arg His Ala Tyr Tyr Tyr Tyr Gly Met
1               5                   10                  15

Asp Val

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Ser Ser Gln Ser Val Leu Tyr Ser Ser Asn Asn Lys Asn Tyr Leu
1               5                   10                  15

Ala

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

```
Trp Ala Ser Thr Arg Glu Ser
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Gln Tyr Tyr Ser Thr Pro Ile Thr
1               5

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Ser Ile Ser Ser Ser Ser Tyr Tyr Trp Gly
1               5                   10

<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ser Ile Tyr Tyr Ser Gly Ser Thr Tyr Tyr Asn Pro Ser Leu Lys Ser
1               5                   10                  15

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Arg Gly Ser Asp Arg Phe His Pro Tyr Phe Asp Tyr
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Ala Ser Gln Ser Val Ser Arg Tyr Leu Ala
1               5                   10

<210> SEQ ID NO 75
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 75

Asp Ala Ser Asn Arg Ala Thr
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Gln Phe Asp Thr Trp Pro Pro Thr
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Phe Thr Phe Thr Asp Tyr
1               5

<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asn Pro Asn Ser Gly Gly
1               5

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asn Leu Gly Pro Ser Phe Tyr Phe Asp Tyr
1               5                   10

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Asp Val Ser Ile Gly Val Ala
1               5

```
<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ser Ala Ser Tyr Arg Tyr Thr
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Gln Tyr Tyr Ile Tyr Pro Tyr Thr
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Phe Asn Ile Lys Asp Thr
1               5

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Tyr Pro Thr Asn Gly Tyr
1               5

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Trp Gly Gly Asp Gly Phe Tyr Ala Met Asp Tyr
1               5                   10

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86
```

```
Gln Asp Val Asn Thr Ala Val Ala
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Ala Ser Phe Arg Tyr Thr
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gln Gln His Tyr Thr Thr Pro Pro Thr
1               5

<210> SEQ ID NO 89
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 90
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Ile Gln Met Thr Gln Ser Pro Ser Thr Leu Ser Ala Ser Val Gly
```

```
                1               5                  10                 15
Asp Arg Val Thr Ile Thr Cys Arg Ala Ser Gln Ser Ile Ser Ser Trp
                20                 25                 30

Leu Ala Trp Tyr Gln Gln Lys Pro Gly Lys Ala Pro Lys Leu Leu Ile
        35                 40                 45

Tyr Lys Ala Ser Ser Leu Glu Ser Gly Val Pro Ser Arg Phe Ser Gly
    50                 55                 60

Ser Gly Ser Gly Thr Glu Phe Thr Leu Thr Ile Ser Ser Leu Gln Pro
65                 70                 75                 80

Asp Asp Phe Ala Thr Tyr Tyr Cys Gln Gln Tyr Asp Ser Tyr Pro Thr
                85                 90                 95

Phe Gly Gly Gly Thr Lys Val Glu Ile Lys
                100                105
```

<210> SEQ ID NO 91
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

```
Gln Val Gln Leu Val Gln Ser Gly Ala Glu Val Lys Lys Pro Gly Ser
1               5                  10                 15

Ser Val Lys Val Ser Cys Lys Ala Ser Gly Gly Thr Phe Ser Ser Tyr
                20                 25                 30

Ala Ile Ser Trp Val Arg Gln Ala Pro Gly Gln Gly Leu Glu Trp Met
        35                 40                 45

Gly Gly Ile Ile Pro Ile Phe Gly Thr Ala Asn Tyr Ala Gln Lys Phe
    50                 55                 60

Gln Gly Arg Val Thr Ile Thr Ala Asp Glu Ser Thr Ser Thr Ala Tyr
65                 70                 75                 80

Met Glu Leu Ser Ser Leu Arg Ser Glu Asp Thr Ala Val Tyr Tyr Cys
                85                 90                 95

Ala Arg Arg Gly Arg Lys Ala Ser Gly Ser Phe Tyr Tyr Tyr Tyr Gly
                100                105                110

Met Asp Val Trp Gly Gln Gly Thr Thr Val Thr Val Ser Ser
        115                120                125
```

<210> SEQ ID NO 92
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

```
Asp Ile Val Met Thr Gln Ser Pro Asp Ser Leu Ala Val Ser Leu Gly
1               5                  10                 15

Glu Arg Ala Thr Ile Asn Cys Glu Ser Ser Gln Ser Leu Leu Asn Ser
                20                 25                 30

Gly Asn Gln Lys Asn Tyr Leu Thr Trp Tyr Gln Gln Lys Pro Gly Gln
        35                 40                 45

Pro Pro Lys Pro Leu Ile Tyr Trp Ala Ser Thr Arg Glu Ser Gly Val
    50                 55                 60

Pro Asp Arg Phe Ser Gly Ser Gly Ser Gly Thr Asp Phe Thr Leu Thr
```

```
                    65                  70                  75                  80
Ile Ser Ser Leu Gln Ala Glu Asp Val Ala Val Tyr Tyr Cys Gln Asn
                    85                  90                  95

Asp Tyr Ser Tyr Pro Tyr Thr Phe Gly Gln Gly Thr Lys Leu Glu Ile
                    100                 105                 110

Lys

<210> SEQ ID NO 93
<211> LENGTH: 246
<212> TYPE: PRT
<213> ORGANISM: Homo sapiens

<400> SEQUENCE: 93

Met Ala Ala Ala Ile Pro Ala Leu Leu Cys Leu Pro Leu Leu
1               5                   10                  15

Phe Leu Leu Phe Gly Trp Ser Arg Ala Arg Arg Asp Asp Pro His Ser
                    20                  25                  30

Leu Cys Tyr Asp Ile Thr Val Ile Pro Lys Phe Arg Pro Gly Pro Arg
                35                  40                  45

Trp Cys Ala Val Gln Gly Gln Val Asp Glu Lys Thr Phe Leu His Tyr
            50                  55                  60

Asp Cys Gly Asn Lys Thr Val Thr Pro Val Ser Pro Leu Gly Lys Lys
65                  70                  75                  80

Leu Asn Val Thr Met Ala Trp Lys Ala Gln Asn Pro Val Leu Arg Glu
                    85                  90                  95

Val Val Asp Ile Leu Thr Glu Gln Leu Leu Asp Ile Gln Leu Glu Asn
                    100                 105                 110

Tyr Thr Pro Lys Glu Pro Leu Thr Leu Gln Ala Arg Met Ser Cys Glu
                115                 120                 125

Gln Lys Ala Glu Gly His Ser Ser Gly Ser Trp Gln Phe Ser Ile Asp
            130                 135                 140

Gly Gln Thr Phe Leu Leu Phe Asp Ser Glu Lys Arg Met Trp Thr Thr
145                 150                 155                 160

Val His Pro Gly Ala Arg Lys Met Lys Glu Lys Trp Glu Asn Asp Lys
                    165                 170                 175

Asp Val Ala Met Ser Phe His Tyr Ile Ser Met Gly Asp Cys Ile Gly
                    180                 185                 190

Trp Leu Glu Asp Phe Leu Met Gly Met Asp Ser Thr Leu Glu Pro Ser
                195                 200                 205

Ala Gly Ala Pro Leu Ala Met Ser Ser Gly Thr Thr Gln Leu Arg Ala
            210                 215                 220

Thr Ala Thr Thr Leu Ile Leu Cys Cys Leu Leu Ile Ile Leu Pro Cys
225                 230                 235                 240

Phe Ile Leu Pro Gly Ile
                245

<210> SEQ ID NO 94
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Gly Ala Pro Asn Tyr Gly Asp Thr Thr His Asp Tyr Tyr Tyr
            100                 105                 110

Met Asp Val Trp Gly Lys Gly Thr Thr Val Thr Val Ser Ser
        115                 120                 125

<210> SEQ ID NO 95
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asp Asp Trp Pro Phe
                85                  90                  95

Thr Phe Gly Gly Gly Thr Lys Val Glu Ile Lys
            100                 105

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Tyr Thr Phe Thr Ser Tyr Tyr Met His
 1               5

<210> SEQ ID NO 97
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ile Ile Asn Pro Ser Gly Gly Ser Thr Ser Tyr Ala Gln Lys Phe Gln
1               5                   10                  15

Gly

<210> SEQ ID NO 98
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Arg Gly Ala Pro Asn Tyr Gly Asp Thr Thr His Asp Tyr Tyr Tyr
1               5                   10                  15

Met Asp Val

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Ala Ser Gln Ser Val Ser Ser Asn Leu Ala
1               5                   10

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Ala Ser Thr Arg Ala Thr
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln Gln Tyr Asp Asp Trp Pro Phe Thr
1               5

<210> SEQ ID NO 102
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

```
Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ala Pro Met Gly Ala Ala Gly Trp Phe Asp Pro Trp
                100                 105                 110

Gly Gln Gly Thr Leu Val Thr Val Ser Ser
                115                 120

<210> SEQ ID NO 103
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Ser Phe Pro Arg
                 85                  90                  95

Thr Phe Gly Gly Gly Thr Lys Val Glu Ile Lys
                100                 105

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Phe Thr Phe Ser Ser Tyr Ser Met Asn
 1               5

<210> SEQ ID NO 105
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ser Ile Ser Ser Ser Ser Ser Tyr Ile Tyr Tyr Ala Asp Ser Val Lys
 1               5                  10                  15
```

```
Gly

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ala Arg Gly Ala Pro Met Gly Ala Ala Ala Gly Trp Phe Asp Pro
1               5                   10                  15

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Arg Ala Ser Gln Gly Ile Ser Ser Trp Leu Ala
1               5                   10

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ala Ala Ser Ser Leu Gln Ser
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gln Gln Gly Val Ser Phe Pro Arg Thr
1               5
```